US010100316B2

(12) United States Patent
Epstein et al.

(10) Patent No.: US 10,100,316 B2
(45) Date of Patent: Oct. 16, 2018

(54) APTAMERS COMPRISING CPG MOTIFS

(75) Inventors: David Epstein, Huntington, NY (US);
Dilara Grate, Waltham, MA (US);
Martin Stanton, Stow, MA (US); John L. Diener, Cambridge, MA (US);
Charles Wilson, Concord, MA (US);
Thomas Greene McCauley,
Somerville, MA (US); Errol Desouza,
Cambridge, MA (US)

(73) Assignee: Archemix LLC, Cambridge, MA (US)

( * ) Notice: Subject to any disclaimer, the term of this patent is extended or adjusted under 35 U.S.C. 154(b) by 613 days.

(21) Appl. No.: 10/829,504

(22) Filed: Apr. 21, 2004

(65) Prior Publication Data

US 2004/0253679 A1 Dec. 16, 2004

Related U.S. Application Data

(63) Continuation-in-part of application No. 10/718,833, filed on Nov. 21, 2003, now abandoned, and a continuation-in-part of application No. 10/826,077, filed on Apr. 15, 2004, now abandoned.

(60) Provisional application No. 60/428,102, filed on Nov. 21, 2002, provisional application No. 60/469,628, filed on May 8, 2003, provisional application No. 60/464,239, filed on Apr. 21, 2003, provisional application No. 60/465,053, filed on Apr. 23, 2003, provisional application No. 60/474,133, filed on May 29, 2003, provisional application No. 60/486,580, filed on Jul. 11, 2003, provisional application No. 60/489,810, filed on Jul. 23, 2003, provisional application No. 60/503,596, filed on Sep. 16, 2003, provisional application No. 60/523,935, filed on Nov. 21, 2003.

(51) Int. Cl.
*C12N 15/115* (2010.01)
*C12N 15/117* (2010.01)

(52) U.S. Cl.
CPC .......... *C12N 15/115* (2013.01); *C12N 15/117* (2013.01); *C12N 2310/16* (2013.01); *C12N 2310/17* (2013.01); *C12N 2310/315* (2013.01); *C12N 2310/3519* (2013.01)

(58) Field of Classification Search
None
See application file for complete search history.

(56) References Cited

U.S. PATENT DOCUMENTS

| | | |
|---|---|---|
| 3,710,795 A | 1/1973 | Higuchi et al. ............... 128/260 |
| 4,683,195 A | 7/1987 | Mullis |
| 4,935,363 A | 6/1990 | Brown et al. |
| 5,070,010 A | 12/1991 | Hsu |
| 5,262,564 A | 11/1993 | Kun et al. ...................... 562/430 |
| 5,270,163 A | 12/1993 | Gold et al. ........................ 435/6 |
| 5,459,015 A | 10/1995 | Janjic et al. |
| 5,475,096 A | 12/1995 | Gold et al. .................... 536/23.1 |
| 5,496,938 A | 3/1996 | Gold et al. .................... 536/22.1 |
| 5,567,588 A | 10/1996 | Gold et al. ......................... 435/6 |
| 5,580,737 A | 12/1996 | Polisky et al. ..................... 435/6 |
| 5,589,332 A | 12/1996 | Shih et al. ......................... 435/6 |
| 5,635,615 A | 6/1997 | Allen et al. |
| 5,637,459 A | 6/1997 | Burke et al. ....................... 435/6 |
| 5,648,214 A | 7/1997 | Nieuwlandt et al. ............. 435/6 |
| 5,654,151 A | 8/1997 | Allen et al. |
| 5,660,985 A | 8/1997 | Pieken et al. ..................... 435/6 |
| 5,668,264 A | 9/1997 | Janjic et al. .................. 536/23.1 |
| 5,672,695 A | 9/1997 | Eckstein et al. ............. 536/24.5 |
| 5,674,685 A | 10/1997 | Janjic et al. ...................... 435/6 |
| 5,674,980 A | 10/1997 | Frankel et al. ................ 530/350 |
| 5,683,867 A | 11/1997 | Biesecker et al. ................ 435/6 |
| 5,698,687 A | 12/1997 | Eckstein et al. ............. 536/25.3 |
| 5,705,337 A | 1/1998 | Gold et al. ......................... 435/6 |
| 5,707,796 A | 1/1998 | Gold et al. ......................... 435/6 |
| 5,723,323 A | 3/1998 | Kauffman et al. |
| 5,723,594 A | 3/1998 | Janjic et al. |
| 5,763,173 A | 6/1998 | Gold et al. |
| 5,763,177 A | 6/1998 | Gold et al. ......................... 435/6 |
| 5,804,604 A | 9/1998 | Frankel et al. ................ 530/324 |
| 5,811,533 A | 9/1998 | Gold et al. |
| 5,817,635 A | 10/1998 | Eckstein et al. ................. 514/44 |
| 5,834,186 A | 11/1998 | George et al. .................... 435/6 |
| 5,849,479 A | 12/1998 | Janjic et al. |
| 5,859,228 A | 1/1999 | Janjic et al. .................. 536/24.3 |

(Continued)

FOREIGN PATENT DOCUMENTS

| | | |
|---|---|---|
| GB | 2183661 A | 6/1987 |
| WO | WO89/06694 | 7/1989 |

(Continued)

OTHER PUBLICATIONS

Que-Gewirth et al (Gene Therapy, (Feb. 2007) vol. 14, No. 4, pp. 283-291).*

(Continued)

*Primary Examiner* — Richard A Schnizer
(74) *Attorney, Agent, or Firm* — Cooley LLP; Ivor R. Elrifi; Christina K. Stock

(57) ABSTRACT

Materials and methods are provided for producing and using aptamers useful as oncology therapeutics capable of binding to PDGF, PDGF isoforms, PDGF receptor, VEGF, and VEGF receptor or any combination thereof with great affinity and specificity. The compositions of the present invention are particularly useful in solid tumor therapy and can be used alone or in combination with known cytotoxic agents for the treatment of solid tumors. Also disclosed are aptamers having one or more CpG motifs embedded therein or appended thereto.

14 Claims, 24 Drawing Sheets

Specification includes a Sequence Listing.

(56) References Cited

U.S. PATENT DOCUMENTS

| | | | |
|---|---|---|---|
| 5,958,691 A | 9/1999 | Pieken et al. | 435/6 |
| 5,972,599 A * | 10/1999 | Tasset et al. | 435/6 |
| 6,011,020 A | 1/2000 | Gold et al. | 514/44 |
| 6,013,443 A | 1/2000 | Heilig et al. | |
| 6,020,130 A | 2/2000 | Gold et al. | |
| 6,051,698 A | 4/2000 | Janjic et al. | 536/24.31 |
| 6,083,696 A | 7/2000 | Biesecker et al. | 435/6 |
| 6,168,778 B1 | 1/2001 | Janjic et al. | |
| 6,207,646 B1 | 3/2001 | Krieg et al. | 514/44 |
| 6,207,816 B1 | 3/2001 | Gold et al. | 536/24.1 |
| 6,214,806 B1 | 4/2001 | Krieg et al. | 514/44 |
| 6,218,371 B1 * | 4/2001 | Krieg et al. | 514/44 R |
| 6,224,866 B1 * | 5/2001 | Barbera-Guillem | 424/130.1 |
| 6,229,002 B1 * | 5/2001 | Janjic et al. | 536/23.1 |
| 6,232,071 B1 | 5/2001 | Hicke et al. | 435/6 |
| 6,239,116 B1 | 5/2001 | Krieg et al. | 514/44 |
| 6,346,611 B1 | 2/2002 | Pagratis et al. | 536/23.1 |
| 6,426,335 B1 | 7/2002 | Janjic et al. | |
| 6,426,434 B1 | 7/2002 | Yoshida et al. | 564/71 |
| 6,429,199 B1 | 8/2002 | Krieg et al. | 514/44 |
| 6,441,158 B1 * | 8/2002 | Dynan et al. | 536/24.5 |
| 6,465,188 B1 | 10/2002 | Gold et al. | |
| 6,498,148 B1 | 12/2002 | Raz | 514/44 |
| 6,514,948 B1 * | 2/2003 | Raz et al. | 514/44 |
| 6,562,798 B1 * | 5/2003 | Schwartz | 514/44 |
| 6,582,918 B2 | 6/2003 | Janjic et al. | |
| 6,610,661 B1 * | 8/2003 | Carson et al. | 514/44 |
| 6,653,292 B1 | 11/2003 | Krieg et al. | 514/44 |
| 6,689,757 B1 * | 2/2004 | Craig | 514/44 R |
| 6,696,252 B2 | 2/2004 | Gold et al. | |
| 6,699,843 B2 | 3/2004 | Pietras et al. | |
| 6,833,373 B1 * | 12/2004 | McKearn et al. | 514/272 |
| 7,569,554 B2 * | 8/2009 | Kandimalla et al. | 514/44 R |
| 2002/0025941 A1 | 2/2002 | Meyer | 514/44 |
| 2002/0034506 A1 * | 3/2002 | Pietras | A61K 47/48053 424/94.63 |
| 2002/0034757 A1 | 3/2002 | Cubicciotti | 435/6 |
| 2002/0119473 A1 * | 8/2002 | Lupold et al. | 435/6 |
| 2002/0192184 A1 * | 12/2002 | Carpentier | 424/93.2 |
| 2003/0036642 A1 | 2/2003 | Janjic et al. | |
| 2003/0114404 A1 | 6/2003 | Janjic et al. | |
| 2003/0176680 A1 | 9/2003 | Gold et al. | |
| 2003/0180744 A1 | 9/2003 | Gold et al. | |
| 2004/0208850 A1 * | 10/2004 | Ellenhorn | C07K 14/4746 424/93.2 |
| 2004/0265912 A1 * | 12/2004 | Gorenstein et al. | 435/7.1 |

FOREIGN PATENT DOCUMENTS

| | | |
|---|---|---|
| WO | WO91/14436 | 10/1991 |
| WO | WO 91/19813 | 12/1991 |
| WO | WO92/05285 | 4/1992 |
| WO | WO 92/07065 | 4/1992 |
| WO | WO92/14842 | 9/1992 |
| WO | WO92/14843 | 9/1992 |
| WO | WO 98/08974 | 3/1998 |
| WO | WO 98/18480 | 5/1998 |
| WO | WO 98/27104 | 6/1998 |
| WO | WO 99/31276 | 6/1999 |
| WO | WO 00/70329 | 11/2000 |
| WO | WO 01/66721 A2 | 9/2001 |
| WO | WO0187351 A1 | 11/2001 |
| WO | WO 02/22882 A2 | 3/2002 |
| WO | WO 03/014375 A2 | 2/2003 |
| WO | WO 04/050899 | 6/2004 |
| WO | WO 04/064760 | 8/2004 |

OTHER PUBLICATIONS

Pestourie et al (Biochimie, (Sep.-Oct. 2005) vol. 87, No. 9-10, pp. 921-230).*
Joshi et al (Current Drug Targets. Infectious disorders, (Dec. 2003) vol. 3, No. 4, pp. 383-400).*
van der Velden et al (Blood 97(10): 3197-3204, 2001).*
Wang et al (Proc. Nat. Acad. Sci. USA 96(2): 847-852, 2000).*
Keefe (Nature Reviews Drug Discovery 9, 537-550 (Jul. 2010)).*
Ahrens et al (Magnetic Resonance in Medicine 49:1006-1013 (2003)).*
Agrawal et al. *Ciba Found. Symp.*, 209:60-75 (1997).
Akhtar et al. *Trends Pharmacol. Sci.*, 18:12-18 (1997).
Antopolsky et al. *Bioconjug. Chem.*, 10(4):598-606 (1999).
Astriab-Fisher et al. *Biochem. Pharmacol.*, 60(1):83-90 (2000).
Bell et al. *In Vitro Anim. Cell. Dev. Biol.*, 35(9):533-542 (1999).
Breaker R.R. *Curr. Opin. Biotech.*, 7:442-448 (1996).
Breaker R.R. *Chem. Rev.*, 97:371-390 (1997).
Breaker R.R. *Curr. Opin. Chem. Biol.*, 1:26-31 (1997).
Breaker R.R. *Nat. Biotech.*, 15:427-431 (1997).
Breaker R.R. Intracellular Ribozyme Applications in Principles and Protocols, pp. 1-19; Horizon Scientific Press, Wymondham UK, Rossi and Couture, eds., (1999).
Breaker R.R. *Curr. Opin. Biotech.*, 13:31-39 (2002).
Carmi et al. *Chem.& Biol.*, 3:1039-1046 (1996).
Carrasquillo et al. *Invest. Ophthalmol. Vis. Sci.*, 44(1):290-299 (2003).
Chen et al. *Proc. Natl. Acad. Sci. USA*, 100(16):9226-9231 (2003).
Cotten et al. *Nucl. Acids Res.*, 19(10):2629-2635 (1991).
Crooke S.T. *Adv. Pharmacol.*, 40:1-49 (1997).
Daniels et al. *Anal. Biochem.*, 305(2):214-226 (2002).
De Rijk et al. *Nucl. Acids Res.*, 25(22):4679-4684 (1997).
Ellington et al. *Nature*, 346(6287):818-822 (1990).
Froehler et al. *Nucl. Acids Res.*, 14(13):5399-5407 (1986).
Froehler et al. *Tet. Lett.*, 27(46):5575-5578 (1986).
Gold L. *Nat. Biotech.*, 20: 671-672 (2002).
Golub et al. *Cell*, 77(2):307-316 (1994).
Green et al. *Chem. Biol.*, 2:683-695 (1995).
Greenwald et al. *J. Org. Chem.*, 60:331-336 (1995).
Griffin et al. *Gene*, 137(1):25-31 (1993).
Grindel et al. *Antisense Nucl. Acid Drug Dev.*, 8(1):43-52 (1998).
Hamaguchi et al. *Anal. Biochem.*, 294:126-131 (2001).
Harris et al. *Nat. Rev. Drug Discov.*, 2(3):214-221 (2003).
Hartig et al. *Nat. Biotech.*, 20:717-722 (2002).
Heinreich et al. *Science*, 299(5607):708-710 (2003).
Hirose et al. *Tet. Lett.*, 28:2449-2452 (1978).
Hobbs et al. *Biochem.*, 12(25):5138-5145 (1973).
Jaeger et al. *Proc. Natl. Acad. Sci. USA.* 86:7706-7710 (1989).
Jain et al. *Cancer Res.*, 47(12):3039-3051 (1987).
Jain et al. *Adv. Drug Deilv.*, 26:71-90 (1997).
Jellinek et al. *Biochem.*, 34(36):11363-11372 (1995).
Jenison et al. *Antisense Nucl. Acid Drug Dev.*, 8(4):265-279 (1998).
Jenne et al. *Nat. Biotech.*, 19:56-61 (2001).
Khati et al. *J. Virol.*, 77(23):12692-12698 (2003).
Koizumi et al. *Nucl. Acids Symp. Ser.*, 42:275-276 (1999).
Koizumi et al. *Nat. Struct. Biol.*, 6(11):1062-1071 (1999).
Kraus et al. *J. Immunol.*, 160:5209-5212 (1998).
Krieg A.M. *Annu. Rev. Immunol.*, 20:709-760 (2002).
Lebedeva et al. *Eur. J. Pharm. Biopharm.*, 50(1):101-119 (2000).
Li et al. *Curr. Opin. Struct. Biol.*, 9:315-323 (1999).
Li et al. *Proc. Natl. Acad. Sci. USA*, 96:2746-2751 (1999).
Lin et al. *Nucl. Acids Res.*, 22(24):5529-5234 (1994).
Magnusson et al., *Blood*, 98(8):2518-2525 (2001).
Manoharan M. *Antisense Nucl. Acid Drug Dev.*, 12(2):103-128 (2002).
Marshall et al., *Nat. Struct. Biol.*, 6(11):992-994 (1999).
Mathews et al. *J. Mol. Biol.*, 288(5):911-940 (1999).
Monteith et al. *Toxicol. Pathol.*, 27(1):8-13 (1999).
O'Brien et al. *Genes Chromosomes & Cancer*, 23(2):187-193 (1998).
Ostman et al. *Adv. Cancer Res.*, 80:1-38 (2001).
Padilla et al. *Nucl. Acids Res.*, 30(24):e138 (2002).
Pagratis et al. *Nat. Biotechnol.*, 15(1):68-73 (1997).
Peng et al. *Antisense Nucl. Acid Drug Dev.*, 11(1):15-27 (2001).
Pieken et al. *Science*, 253:314-317 (1991).
Pietersz et al. *Vaccine*, 19(11-12):1397-1405 (2001).
Pietras et al. *Cancer Res.*, 61:2929-2934 (2001).

(56) References Cited

OTHER PUBLICATIONS

Pietras et al. *Cancer Res.*, 62:5476-5484 (2002).
Pietras et al. *Cancer Cell*, 3:439-443 (2003).
Potyrailo et al. *Anal. Chem.*, 70:3419-3425 (1998).
Reyderman et al. *Pharm. Res.*, 15(6):904-910 (1998).
Richardson et al. *Biochem. Pharmacol.*, 59(9):1045-1052 (2000).
Richardson et al. *Chem. Res. Toxicol.*, 15(7):922-926 (2002).
Robertson et al. *Nucl. Acids Res.*, 28(8):1751-1759 (2000).
Robertson et al. *Nat. Biotech.*, 17:62-66 (1999).
Robertson et al. *Nat. Biotech.*, 19:650-655 (2001).
Rothbard et al. *Nat. Med.*, 6(11):1253-1257 (2000).
Rothbard J. *J. Med. Chem.*, 45(17):3612-3618 (2002).
Ruckman et al. *J. Biol. Chem.*, 273(32):20556-20567 (1998).
Sassanfar et al. *Nature*, 364:550-553 (1993).
Seetharaman et al. *Nat. Biotech.*, 19:336-341 (2001).
Seiwert et al. *Chem.& Biol.*, 7:833-843 (2000).
Shimiziu et al. *Cancer Res.*, 59:3719-3723 (1999).
Simon et al. *Nat. Genet.*, 15:95-98 (1997).
Smidt et al. *Nucl. Acids Res.*, 19(17):4695-4700 (1991).
Smith et al. *Cell*, 89(5):669-672 (1997).
Sood et al. *Nucl. Acids Res.*, 4(8):2757-2765 (1977).
Soukup et al. *Proc. Natl. Acad. Sci. USA*, 96:3584-3589 (1999).
Soukup et al. *RNA*, 5:1308-1325 (1999).
Soukup et al. *Structure*, 7(7):783-791 (1999).
Soukup et al. *Tren. Biotech.*, 17:469-476 (1999).
Soukup et al. in *Ribozyme Biochem. Biotech.*, Eaton Publishing, Chapter 8, pp. 149-170, Krupp & Gaur, eds. (2000).
Soukup et al. *RNA*, 7:524-536 (2001).
Soukup et al. *J. Mol. Biol.*, 298:623-632 (2000).
Sproat et al. *Nucl. Acids Res.*, 19(4):733-738 (1991).
Srinivasan et al. *J. Clin. Lab. Anal.*, 9(2):129-137 (1995).
Tang et al. *Chem. & Biol.*, 4:453-459 (1997).
Tang et al. *Nucl. Acids Res.*, 26(18):4214-4221 (1998).
Tang et al. *RNA*, 3:914-925 (1997).
Tavitian et al. *Nat. Med.*, 4(4):467-471 (1998).
Tucker et al. *J. Chromatography B*, 732:203-212 (1999).
Tuerk et al. *Science*, 249(4968):505-510 (1990).
Uhlmann et al. *Methods Enzymol.*, 313:268-284 (2000).
Vaish et al. *Biochem.*, 42(29):8842-8851 (2003).
Vives et al. *J. Biol. Chem.*, 272(25):16010-16017 (1997).
Watson et al. *Antisense Nucl. Acid Drug Dev.*, 10(2):63-75 (2000).
Wlotzka et al. *Proc. Natl. Acad. Sci. USA*, 99(13):8898-8902 (2002).
Zubin et al. *FEBS Lett.*, 456(1):59-62 (1999).
Zuker M. *Science*, 244:48-52 (1989).
Agrawal, S., et al., Antisense and/or Immunostimulatory Oligonucleotide Therapeutics, Current Cancer Drug Targets, 1:197-209 (2001).
Andrake (1988) Proc. Natl. Acad. Sci. USA 85:7942.
Balasubramanian, V. et al., Role of Platelet Derived Growth Factor in Vascular Remodeling during Pulmonary Hypertension the Ovine Fetus, Am J. Physiol Lung Cell Mol Phy, 284:L826-33 (2003).
Bergers, G., et al. Benefits of targeting both pericytes and endothelial cells in the tumor vasculature with kinase inhibitors, Journal of Clin Invest vol. 111:9: 1287-95 (May 2003).
Binkley, J. et al., RNA Ligands to Human Nerve Growth Factor, Nucleic Acids Research (1995), vol. 23, No. 16 p. 3198-3205.
Carey et al., (1983) Biochem. 22(11 ):2601-10.
Cerchia, L., et al., Nucleic acid aptamers in cancer medicine, Federation of European Biochemical Societies, 528, 12-16 (2002).
Cload, S., The Aptamer Therapeutics Company, RNA in Drug Development, San Diego, CA., Nov. 10, 2003.
Cohen et al., (1969) Proc. Natl. Acad. Sci. USA 63:458-64.
Davis, J., et al., Identifying Consensus Patterns and Secondary Structure in SELEX Sequence Seta, Methods in Enzymology, vol. 267 (18) 302-314, (1996).
Drolet, D. et al., Pharmacokinetics and Safety of an Anti-Vascular Endothelial Growth Factor Aptamer . . . , Pharmaceutical Research, vol. 17, No. 12:1503-9 (2000).

Ellington & Szostak (1990) Abstracts of papers presented at the 1990 meeting on RNA Processing, Cold Spring Harbor Laboratory, Cold Spring Harbor, NY, p. 84.
Fitzwater, T., et al., A Selex Primer, Methods in Enzymology, vol. 267 (17) 275-301 (1996).
Floege, J., et al., Novel Approach to Specific Growth Factor Inhibition in Vivo, American Journal of Pathology, vol. 154, No. 1:169-179 (Jan. 1999).
Fredriksson S., et al., Protein detection using proximity-dependent DNA Ligation assays, Nature Biotechnology, vol. 20: 473-77 (May 2002).
Grate, Dilara, PDGF Blockade data, AACR 2004, Orlando, Florida , Mar. 27, 2004.
Green, L.S. et al., Inhibitory DNA Ligands to Platelet Derived Growth Factor B-Chain, Biochemistry, 35:14413-14424 (1996).
Griffen, R., et al., Simultaneous Inhibition of the Receptor Kinase Activity of Vascular Endothelial, Fibroblast, and Platelet-derived . . . , Cancer Research 62: 1702-1706 (2002).
Huang, J., et al., Highly Specific Antiangiogenic Therapy is Effective in Suppressing Growth of Experimental Wilms Tumors, J. of Pediatric Surgery, vol. 36, No. 2:357-361 (2001).
Jellinek, D., High-Affinity RNA Ligands to Basic Fibroblast Growth Factor Inhibit Receptor Binding, Proc. Nat'l Acad. Sci. USA, vol. 90, pp. 11227-11231, Dec. 1993.
Jellinek, D., Inhibition of Receptor Binding by High-Affinity RNA Ligands to Vascular Endothelial Growth Factor, Biochemistry, 1994, 33:10450-56.
Joyce (1989) Gene, RNA: Catalysis, Splicing, Evolution, 82:83.
Joyce & Innoue (1989) Nucleic Acids Research 17:711-22.
Kacian et al. (1972) Proc. Natl. Acad. Sci. USA 69:3038-42.
Kadonaga et al. (1986) Proc. Natl. Acad. Sci. USA 83:5889-93.
Kim, E. et al., Potent VEGF Blockade Causes Regression of Coopted Vessels in a Model of Neuroblastoma, PNAS, Aug. 20, 2002, vol. 99, No. 17, pp. 11399-11404.
Kinzler & Vogelstein (1989) Nucleic Acids Research 17:3645-53.
Kinzler et al. (1990) Mol. Cell. Biol. 10:634-42.
Kramer et al. (1974) J. Mol. Biol. 89:719-36.
Leppanen, OL, et al., Intimal Hyperplasia Recurs After Removal of PDGF-AB and-BB Inhibition in the Rate Carotid Artery Injury Model, Arterioscler Throm Vasc Biol. (Nov. 2000) 20:e89-e95.
Lestienne et al. (1983) Biochime. 65:49-52.
Levisohn & Spiegelman (1968) PNAS USA 60:866-72.
Levisohn & Spiegelman (1969) PNAS USA 63:805-11.
Ma and Ptashne (1987) Cell 51: 113-19.
Maniatis (1982) Molecular Cloning: a Laboratory Manual,. paqe 118.
Maniatis et al. (1987) Science 236: 1237-45.
Miele et al.. (1983)J. Mol. Biol. 171:281-95.
Mills et al.. (1967) Proc. Natl. Acad. Sci. 58:217-220.
Mills et al. (1973) Science 180:916-27.
Min et al. (1988) Nucleic Acids Res. 16:5075-88.
Muesing et al. (1985) Nature 313:450-58.
Oliphant & Struhl 1 (1987) Methods in Enzymology 155:568-82.
Oliphant & Struhl 1 (1988) Nucleic Acids Research 16:7673-83.
Oliphant et al. (1986) Gene 44:177-83.
Oliphant et al. (1989) Mol. Cell. Biol. 9:2944-49.
Orgel (1979) Proc. R. Soc. Lon. B205:435-42.
Ostendorf, T. et al., The Journal of Clinical Investigation, (Oct. 1999), vol. 104, No. 7:913-29.
Ostendorf, T. et al, J Am Soc Nephrol 12:909-918, 2001.
Ostendorf, T. et al, , J Am Soc Nephrol 13: 658-667, 2002.
Ou et al. (1988) Science 239:295-97.
Ringquist, S. et al., (1998) Cytometry 33:394-405.
Robertson & Joyce (1990) Nature 344:467-68.
Romaniuk et al. (1987) Biochem. 26(6):1563-68.
Saffhill et al. (1970) J. Mol. Biol. 51 :531-39.
Sambrook et al. (1989) Molecular Cloning: A Laboratory Manual., Cold Spring Harbor, NY, section 8.9-8.10.
Sjöblom, T., Paracrine and Autocrine Functions of PDGF in Malignant Disease, Comprehensive Summaries of Uppsala Dissertations From the Faculty of Medicine (2002).
Singleton et al., Dictionary of Microbiol. & Molec. Biol., Wiley & Sons, New York, NY, 2nd ed. p. 270.

(56) References Cited

OTHER PUBLICATIONS

Szostak, A., Structure and Activity of Ribozymes, in Redesigning the Molecules of Life, (SA Benner ed.) Springer-Verlag Berline Heidelberg, pp. 87-113 (1988).
Thiesen & Bach (1990) Nucleic Acids Research 18:3203-9.
Uhlenbeck et al. (1983) J. Biomolecular Structure and Dynamics 1:539-52.
Uhrbom, L., et al., Int., J. Cancer: 85, 398-406 (2000).
Watson et al. (1987) Molecular Biolology of the Gene. Benjamin/Cummings Publishing Co., Inc. California, pp. 267,295,323,361,394,396,397 and 405.
Willis, M., et al., Bioconjugate Chem. 1998, 9, 573-582.
Wu, C. et al., Human Gene Therapy 14:849-860 (Jun. 10, 2003).
Belyea, et al., *Am. J. Phthalmol.*, 124(1):40-45 (1997).
Blindish, et al., *Ophthalmol.*, 109(7):1336-1342 (2002).
Broadway, et al., *Invest. Ophtalmol. Vis. Sci.*, "Adjunctive anti-TGFβ2 human Mab as a novel agent to prevent scarring following phacotrabeculectomy", 43:E-Abstract 3331 (2002).
Kupin, et al., *Am. J. Ophthalmol.*, 119:30-39 (1995).
Ochiai, et al., *Jpn. J. Ophthalmol.*, 46(3):249-253 (2002).
Tripathi, et al., *Exp. Eye Res.*, 58(5):523-528 (1994).
International Search Report for PCT/US03/37338, dated Aug. 23, 2004.
Lewis, et al., *Bioconjug. Chem.*, 12(2):320-324 (2001).
Stetsenko, et al., *Nucleosides, Nucleotides & Nucl. Acids*, 19(10-12):1751-1764 (2000).
Eaton et al., "Post-SELEX Combinatorial Optimization of Aptamers", *Bio. Med. Chem.*, 5(6):1087-1096 (1997).
Fang et al., "Synthetic DNA Aptamers to Detect Protein Molecular Variants in a High Throughput Fluorescence Quencing Assay", *ChemBioChem.*, 4:829-834 (2003).
Golden et al., "Diagnostic potential of PhotoSELEX-evolved ssDNA aptamers", J. Biotech., 81:167-178 (2000).
Martin-Orozco et al., "Enhancement of antigen-presenting cell surface molecules involved in cognate interactions by immunostimulatory DNA sequences", *Intl. Immunol.*, 11(7):1111-1118 (1999).
Hartmann et al., "Mechanism and Function of a Newly Identified CpG DNA Motif in Human Primary B Cells", *J. Immunol.*, 164:944-952 (2000).
Hartmann et al., "Cytokines and therapeutic oligonucleotides", *Cell Mol. Ther.*, 3:247-256 (1997).
Hartmann et al., "Rational design of new CpG oligonucleotides that combine B cell activation with high IFN-α induction in plasmacytoid dendritic cells", *Eur. J. Immunol.*, 33:1633-1641 (2003).

\* cited by examiner

A)

B)

A)

B)

A)

B)

A)

B)

A)

B)

```
          mA  mA
      mG       mG
        mA mU
          mG mC
    mU
    mU
          mU mG
          mG mC
    mA
          mC mG
          mG mC
          mU mA
          mA mU
              idT
```

ARC126

ARC126= SEQ ID NO:1-HEG-SEQ ID NO:2-HEG-SEQ ID NO:3-[3T]

A)

B)

C)

D)

E)

standard PEGylation multiple PEGylation dimerization via PEGylation

SEQUENCE LISTING

```
<160> NUMBER OF SEQ ID NOS: 98

<210> SEQ ID NO 1
<211> LENGTH: 9
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (6)..(6)
<223> OTHER INFORMATION: 2'-Fluoro-Uracil
<220> FEATURE:
<221> NAME/KEY: modified_base
<222> LOCATION: (8)..(8)
<223> OTHER INFORMATION: 2'-Fluoro-Cytosine
<220> FEATURE:
<221> NAME/KEY: modified_base
<222> LOCATION: (9)..(9)
<223> OTHER INFORMATION: gm

<400> SEQUENCE: 1 caggcuacg                                                                9

<210> SEQ ID NO 2
<211> LENGTH: 12
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (10)..(10)
<223> OTHER INFORMATION: 2' Fluoro-Uracil
<220> FEATURE:
<221> NAME/KEY: modified_base
<222> LOCATION: (11)..(11)
<223> OTHER INFORMATION: 2' Fluoro-Cytosine
<220> FEATURE:
<221> NAME/KEY: modified_base
<222> LOCATION: (12)..(12)
<223> OTHER INFORMATION: 2'-O-methyl-Adenosine

<400> SEQUENCE: 2
cgtagagcau ca                                                           12

<210> SEQ ID NO 3
<211> LENGTH: 9
<212> TYPE: DNA
<213> ORGANISM: Artificial
<220> FEATURE:
<223> OTHER INFORMATION: aptamer
<220> FEATURE:
```

```
<221> NAME/KEY: modified_base
<222> LOCATION: (5)..(6)
<223> OTHER INFORMATION: 2'-fluoro-Cytosine
<220> FEATURE:
<221> NAME/KEY: modified_base
<222> LOCATION: (7)..(7)
<223> OTHER INFORMATION: 2'-fluoro-Uracil
<220> FEATURE:
<221> NAME/KEY: modified_base
<222> LOCATION: (8)..(8)
<223> OTHER INFORMATION: gm

<400> SEQUENCE: 3 tgatccugt                                                                    9

<210> SEQ ID NO 4
<211> LENGTH: 9
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (4)..(4)
<223> OTHER INFORMATION: 2'-fluoro-Cytosine
<220> FEATURE:
<221> NAME/KEY: modified_base
<222> LOCATION: (4)..(4)
<223> OTHER INFORMATION: 2'-fluoro-cytosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluoro-Uracil
<220> FEATURE:
<221> NAME/KEY: modified_base
<222> LOCATION: (8)..(8)
<223> OTHER INFORMATION: 2'-fluoro-Cytosine
<220> FEATURE:
<221> NAME/KEY: modified_base
<222> LOCATION: (9)..(9)
<223> OTHER INFORMATION: gm

<400> SEQUENCE: 4 cagcguacg                                                                    9

<210> SEQ ID NO 5
<211> LENGTH: 12
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (10)..(10)
<223> OTHER INFORMATION: 2'-fluoro-Uracil
<220> FEATURE:
<221> NAME/KEY: modified_base
<222> LOCATION: (11)..(11)
<223> OTHER INFORMATION: 2'-fluoro-Cytosine
<220> FEATURE:
<221> NAME/KEY: modified_base
<222> LOCATION: (12)..(12)
<223> OTHER INFORMATION: 2'-methyl-Adenosine
<220> FEATURE:
<221> NAME/KEY: modified_base
<222> LOCATION: (12)..(12)
<223> OTHER INFORMATION: 2'-O-methyl-adenosine
```

```
<400> SEQUENCE: 5
cgtaccgatu ca                                                              12

<210> SEQ ID NO 6
<211> LENGTH: 9
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (6)..(6)
<223> OTHER INFORMATION: 2'-fluoro-Cytosine
<220> FEATURE:
<221> NAME/KEY: modified_base
<222> LOCATION: (7)..(7)
<223> OTHER INFORMATION: 2'-fluoro-Uracil
<220> FEATURE:
<221> NAME/KEY: modified_base
<222> LOCATION: (8)..(8)
<223> OTHER INFORMATION: gm

<400> SEQUENCE: 6 tgaagcugt                                                                   9

<210> SEQ ID NO 7
<211> LENGTH: 23
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (1)..(1)
<223> OTHER INFORMATION: 2'-O-methyl-adenosine
<220> FEATURE:
<221> NAME/KEY: modified_base
<222> LOCATION: (2)..(2)
<223> OTHER INFORMATION: 2'-O-methyl-uracil
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-O-methyl-adenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(9)
<223> OTHER INFORMATION: 2'-O-methyl-uracil
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: 2'-O-methyl-adenosine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(14)
```

```
<223> OTHER INFORMATION: 2'-O-methyl-adenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-O-methyl-uracil
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: gm
<220> FEATURE:
<221> NAME/KEY: modified_base
<222> LOCATION: (21)..(21)
<223> OTHER INFORMATION: cm
<220> FEATURE:
<221> NAME/KEY: modified_base
<222> LOCATION: (22)..(22)
<223> OTHER INFORMATION: 2'-O-methyl-adenosine
<220> FEATURE:
<221> NAME/KEY: modified_base
<222> LOCATION: (23)..(23)
<223> OTHER INFORMATION: 2'-O-methyl-uracil

<400> SEQUENCE: 7
augcaguuug agaagucgcg cau                                           23

<210> SEQ ID NO 8
<211> LENGTH: 29
<212> TYPE: DNA
<213> ORGANISM: Artificial
<220> FEATURE:
<223> OTHER INFORMATION: aptamer

<400> SEQUENCE: 8
caggctacgc gtagagcatc atgatcctg                                     29

<210> SEQ ID NO 9
<211> LENGTH: 56
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (10)..(10)
<223> OTHER INFORMATION: 2'-O-methyl-adenosine
<220> FEATURE:
<221> NAME/KEY: modified_base
<222> LOCATION: (11)..(11)
<223> OTHER INFORMATION: 2'-O-methyl-uracil
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: cm
<220> FEATURE:
<221> NAME/KEY: modified_base
```

-continued

```
<222> LOCATION: (14)..(14)
<223> OTHER INFORMATION: 2'-O-methyl-adenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(18)
<223> OTHER INFORMATION: 2'-O-methyl-uracil
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyl-adenosine
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(23)
<223> OTHER INFORMATION: 2'-O-methyl-adenosine
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(25)
<223> OTHER INFORMATION: 2'-O-methyl-uracil
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: gm
<220> FEATURE:
<221> NAME/KEY: modified_base
<222> LOCATION: (28)..(28)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: 2'-O-methyl-adenosine
<220> FEATURE:
<221> NAME/KEY: modified_base
<222> LOCATION: (32)..(32)
<223> OTHER INFORMATION: 2'-O-methyl-uracil

<400> SEQUENCE: 9
caggctacga ugcaguuuga gaagucgcgc aucgtagagc atcagaaatg atcctg          56

<210> SEQ ID NO 10
<211> LENGTH: 54
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (10)..(10)
<223> OTHER INFORMATION: 2'-O-methyl-uracil
<220> FEATURE:
```

```
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-O-methyl-adenosine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(17)
<223> OTHER INFORMATION: 2'-O-methyl-uracil
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-O-methyl-adenosine
<220> FEATURE:
<221> NAME/KEY: modified_base
<222> LOCATION: (20)..(20)
<223> OTHER INFORMATION: gm
<220> FEATURE:
<221> NAME/KEY: modified_base
<222> LOCATION: (21)..(22)
<223> OTHER INFORMATION: 2'-O-methyl-adenosine
<220> FEATURE:
<221> NAME/KEY: modified_base
<222> LOCATION: (23)..(23)
<223> OTHER INFORMATION: gm
<220> FEATURE:
<221> NAME/KEY: modified_base
<222> LOCATION: (24)..(24)
<223> OTHER INFORMATION: 2'-O-methyl-uracil
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: gm
<220> FEATURE:
<221> NAME/KEY: modified_base
<222> LOCATION: (27)..(27)
<223> OTHER INFORMATION: cm
<220> FEATURE:
<221> NAME/KEY: modified_base
<222> LOCATION: (28)..(28)
<223> OTHER INFORMATION: gm
<220> FEATURE:
<221> NAME/KEY: modified_base
<222> LOCATION: (29)..(29)
<223> OTHER INFORMATION: cm
<220> FEATURE:
<221> NAME/KEY: modified_base
<222> LOCATION: (30)..(30)
<223> OTHER INFORMATION: 2'-O-methyl-adenosine

<400> SEQUENCE: 10
caggctacgu gcaguuugag aagucgcgca cgtagagcat cagaaatgat cctg      54

<210> SEQ ID NO 11
<211> LENGTH: 39
<212> TYPE: DNA
<213> ORGANISM: Artificial
<220> FEATURE:
<223> OTHER INFORMATION: aptamer
```

```
<400> SEQUENCE: 11
cacaggctac ggcacgtaga gcatcaccat gatcctgtg                              39

<210> SEQ ID NO 12
<211> LENGTH: 22
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(22)
<223> OTHER INFORMATION: phosphorothioate backbone

<400> SEQUENCE: 12
tgactgtgaa cgttcgagat ga                                                22

<210> SEQ ID NO 13
<211> LENGTH: 14
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(14)
<223> OTHER INFORMATION: phosphorothioate backbone

<400> SEQUENCE: 13
tgaacgttcg agat                                                         14

<210> SEQ ID NO 14
<211> LENGTH: 12
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(12)
<223> OTHER INFORMATION: phosphorothioate backbone

<400> SEQUENCE: 14
aacgttcgag at                                                           12

<210> SEQ ID NO 15
<211> LENGTH: 10
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(10)
<223> OTHER INFORMATION: phosphorothioate backbone

<400> SEQUENCE: 15
aacgttcgag                                                              10

<210> SEQ ID NO 16
<211> LENGTH: 13
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(13)
```

```
<223> OTHER INFORMATION: phosphorothioate backbone

<400> SEQUENCE: 16
gtgaacgttc gag                                                        13

<210> SEQ ID NO 17
<211> LENGTH: 24
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(24)
<223> OTHER INFORMATION: phosphorothioate backbone

<400> SEQUENCE: 17
tcgtcgtttt gtcgttttgt cgtt                                            24

<210> SEQ ID NO 18
<211> LENGTH: 18
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(18)
<223> OTHER INFORMATION: phosphorothioate backbone

<400> SEQUENCE: 18
gtcgttttgt cgttttgt                                                   18

<210> SEQ ID NO 19
<211> LENGTH: 14
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(14)
<223> OTHER INFORMATION: phosphorothioate backbone

<400> SEQUENCE: 19
gtcgttttgt cgtt                                                       14

<210> SEQ ID NO 20
<211> LENGTH: 46
<212> TYPE: DNA
<213> ORGANISM: Artificial
<220> FEATURE:
<223> OTHER INFORMATION: aptamer

<400> SEQUENCE: 20
aacgttcgag caggctacgg cacgtagagc atcaccatga tcctgc                    46

<210> SEQ ID NO 21
<211> LENGTH: 49
<212> TYPE: DNA
<213> ORGANISM: Artificial
<220> FEATURE:
<223> OTHER INFORMATION: aptamer

<400> SEQUENCE: 21
gtgaacgttc gagcaggcta cggcacgtag agcatcacca tgatcctgc                 49
```

```
<210> SEQ ID NO 22
<211> LENGTH: 64
<212> TYPE: DNA
<213> ORGANISM: Artificial
<220> FEATURE:
<223> OTHER INFORMATION: aptamer

<400> SEQUENCE: 22
tgactgtgaa cgttcgagat gacaggctac ggcacgtaga gcatcaccat gatcctgttt    60
tttt                                                                 64

<210> SEQ ID NO 23
<211> LENGTH: 34
<212> TYPE: DNA
<213> ORGANISM: Artificial
<220> FEATURE:
<223> OTHER INFORMATION: aptamer

<400> SEQUENCE: 23
caggctacgt tcgtagagca tcaccatgat cctg                                34

<210> SEQ ID NO 24
<211> LENGTH: 35
<212> TYPE: DNA
<213> ORGANISM: Artificial
<220> FEATURE:
<223> OTHER INFORMATION: aptamer

<400> SEQUENCE: 24
caggctacgt ttcgtagagc atcaccatga tcctg                               35

<210> SEQ ID NO 25
<211> LENGTH: 35
<212> TYPE: DNA
<213> ORGANISM: Artificial
<220> FEATURE:
<223> OTHER INFORMATION: aptamer

<400> SEQUENCE: 25
caggcaacgt ttcgttgagc atcaccatga tcctg                               35

<210> SEQ ID NO 26
<211> LENGTH: 34
<212> TYPE: DNA
<213> ORGANISM: Artificial
<220> FEATURE:
<223> OTHER INFORMATION: aptamer

<400> SEQUENCE: 26
caggcaacgt tcgttgagca tcaccatgat cctg                                34

<210> SEQ ID NO 27
<211> LENGTH: 36
<212> TYPE: DNA
<213> ORGANISM: Artificial
<220> FEATURE:
<223> OTHER INFORMATION: aptamer

<400> SEQUENCE: 27
caggcaacgt tttcgttgag catcaccatg atcctg                              36

<210> SEQ ID NO 28
<211> LENGTH: 35
<212> TYPE: DNA
<213> ORGANISM: Artificial
<220> FEATURE:
```

<223> OTHER INFORMATION: aptamer

<400> SEQUENCE: 28
caggctacgt tcgtagagc atcaccatga tcctg    35

<210> SEQ ID NO 29
<211> LENGTH: 35
<212> TYPE: DNA
<213> ORGANISM: Artificial
<220> FEATURE:
<223> OTHER INFORMATION: aptamer

<400> SEQUENCE: 29
caggctacgt tcgtagagc atcaccatga tcctg    35

<210> SEQ ID NO 30
<211> LENGTH: 36
<212> TYPE: DNA
<213> ORGANISM: Artificial
<220> FEATURE:
<223> OTHER INFORMATION: aptamer

<400> SEQUENCE: 30
caggcgtcgt tttcgacgag catcaccatg atcctg    36

<210> SEQ ID NO 31
<211> LENGTH: 36
<212> TYPE: DNA
<213> ORGANISM: Artificial
<220> FEATURE:
<223> OTHER INFORMATION: aptamer

<400> SEQUENCE: 31
caggcgtcgt cgtcgacgag catcaccatg atcctg    36

<210> SEQ ID NO 32
<211> LENGTH: 36
<212> TYPE: DNA
<213> ORGANISM: Artificial
<220> FEATURE:
<223> OTHER INFORMATION: aptamer

<400> SEQUENCE: 32
caggcttcgt cgtcgaagag catcaccatg atcctg    36

<210> SEQ ID NO 33
<211> LENGTH: 36
<212> TYPE: DNA
<213> ORGANISM: Artificial
<220> FEATURE:
<223> OTHER INFORMATION: aptamer

<400> SEQUENCE: 33
caggctacgt cgtcgtagag catcaccatg atcctg    36

<210> SEQ ID NO 34
<211> LENGTH: 35
<212> TYPE: DNA
<213> ORGANISM: Artificial
<220> FEATURE:
<223> OTHER INFORMATION: aptamer

<400> SEQUENCE: 34
caggcaagct ttgcttgagc atcaccatga tcctg    35

<210> SEQ ID NO 35
<211> LENGTH: 36
<212> TYPE: DNA
<213> ORGANISM: Artificial
<220> FEATURE:
<223> OTHER INFORMATION: aptamer

<400> SEQUENCE: 35
caggcaagct tttgcttgag catcaccatg atcctg                          36

<210> SEQ ID NO 36
<211> LENGTH: 33
<212> TYPE: DNA
<213> ORGANISM: Artificial
<220> FEATURE:
<223> OTHER INFORMATION: aptamer

<400> SEQUENCE: 36
cacaggctac ggcacgtaga gcatcaccat gat                             33

<210> SEQ ID NO 37
<211> LENGTH: 10
<212> TYPE: DNA
<213> ORGANISM: Artificial
<220> FEATURE:
<223> OTHER INFORMATION: aptamer

<400> SEQUENCE: 37
aacgttcgag                                                       10

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 93
<212> TYPE: DNA
<213> ORGANISM: Artificial
<220> FEATURE:
<223> OTHER INFORMATION: pool
<220> FEATURE:
<221> NAME/KEY: misc_feature
<222> LOCATION: (25)..(54)
<223> OTHER INFORMATION: n is a, c, g, t or u

<400> SEQUENCE: 50
catcgatgct agtcgtaacg atccnnnnnn nnnnnnnnnn nnnnnnnnnn nnnncgagaa    60
cgttctctcc tctccctata gtgagtcgta tta    93

<210> SEQ ID NO 51
<211> LENGTH: 92
<212> TYPE: DNA
<213> ORGANISM: Artificial
<220> FEATURE:
<223> OTHER INFORMATION: pool
<220> FEATURE:
<221> NAME/KEY: misc_feature
<222> LOCATION: (24)..(53)
<223> OTHER INFORMATION: n is a, c, g, t or u

<400> SEQUENCE: 51
catgcatcgc gactgactag ccgnnnnnnn nnnnnnnnnn nnnnnnnnnn nnngtagaac    60
gttctctcct ctccctatag tgagtcgtat ta    92

<210> SEQ ID NO 52
<211> LENGTH: 92

-continued

```
<212> TYPE: DNA
<213> ORGANISM: Artificial
<220> FEATURE:
<223> OTHER INFORMATION: pool
<220> FEATURE:
<221> NAME/KEY: misc_feature
<222> LOCATION: (24)..(53)
<223> OTHER INFORMATION: n is a, c, g, t or u

<400> SEQUENCE: 52
catcgatcga tcgatcgaca gcgnnnnnnn nnnnnnnnnn nnnnnnnnnn nnngtagaac      60
gttctctcct ctccctatag tgagtcgtat ta                                    92

<210> SEQ ID NO 53
<211> LENGTH: 9
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (9)..(9)
<223> OTHER INFORMATION: gm

<400> SEQUENCE: 53 caggctacg                                                               9

<210> SEQ ID NO 54
<211> LENGTH: 12
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (12)..(12)
<223> OTHER INFORMATION: 2'-O-methyl-adenosine

<400> SEQUENCE: 54
cgtagagcat ca                                                          12

<210> SEQ ID NO 55
<211> LENGTH: 8
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (8)..(8)
<223> OTHER INFORMATION: gm

<400> SEQUENCE: 55 tgatcctg                                                                8

<210> SEQ ID NO 56
<211> LENGTH: 9
<212> TYPE: DNA
<213> ORGANISM: Artificial
<220> FEATURE:
<223> OTHER INFORMATION: aptamer
<220> FEATURE:
```

```
<221> NAME/KEY: modified_base
<222> LOCATION: (6)..(6)
<223> OTHER INFORMATION: 2'-O-methyl-uracil
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: gm

<400> SEQUENCE: 56 caggcuacg                                                                  9

<210> SEQ ID NO 57
<211> LENGTH: 12
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (10)..(10)
<223> OTHER INFORMATION: 2'-O-methyl-uracil
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-O-methyl-adenosine

<400> SEQUENCE: 57
cgtagagcau ca                                                             12

<210> SEQ ID NO 58
<211> LENGTH: 8
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(6)
<223> OTHER INFORMATION: cm
<220> FEATURE:
<221> NAME/KEY: modified_base
<222> LOCATION: (7)..(7)
<223> OTHER INFORMATION: 2'-O-methyl-uracil

<400> SEQUENCE: 58 tgatccug                                                                   8

<210> SEQ ID NO 59
<211> LENGTH: 9
<212> TYPE: DNA
<213> ORGANISM: Artificial
<220> FEATURE:
<223> OTHER INFORMATION: aptamer

<400> SEQUENCE: 59 caggctacg                                                                  9
```

```
<210> SEQ ID NO 60
<211> LENGTH: 12
<212> TYPE: DNA
<213> ORGANISM: Artificial
<220> FEATURE:
<223> OTHER INFORMATION: aptamer

<400> SEQUENCE: 60
cgtagagcat ca                                                        12

<210> SEQ ID NO 61
<211> LENGTH: 8
<212> TYPE: DNA
<213> ORGANISM: Artificial
<220> FEATURE:
<223> OTHER INFORMATION: aptamer

<400> SEQUENCE: 61 tgatcctg                                                              8

<210> SEQ ID NO 62
<211> LENGTH: 9
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: 2'-O-methyl-adenosine
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-O-methyl-uracil
<220> FEATURE:
<221> NAME/KEY: modified_base
<222> LOCATION: (7)..(7)
<223> OTHER INFORMATION: 2'-O-methyl-adenosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: gm

<400> SEQUENCE: 62 caggcuacg                                                             9

<210> SEQ ID NO 63
<211> LENGTH: 12
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (1)..(1)
```

```
<223> OTHER INFORMATION: cm
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyl-uracil
<220> FEATURE:
<221> NAME/KEY: modified_base
<222> LOCATION: (4)..(4)
<223> OTHER INFORMATION: 2'-O-methyl-adenosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-O-methyl-adenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: 2'-O-methyl-adenosine
<220> FEATURE:
<221> NAME/KEY: modified_base
<222> LOCATION: (10)..(10)
<223> OTHER INFORMATION: 2'-O-methyl-uracil
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-O-methyl-adenosine

<400> SEQUENCE: 63
cguagagcau ca                                                          12

<210> SEQ ID NO 64
<211> LENGTH: 8
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (1)..(1)
<223> OTHER INFORMATION: 2'-O-methyl-uracil
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyl-adenosine
<220> FEATURE:
<221> NAME/KEY: modified_base
<222> LOCATION: (4)..(4)
<223> OTHER INFORMATION: 2'-O-methyl-uracil
<220> FEATURE:
<221> NAME/KEY: modified_base
<222> LOCATION: (5)..(6)
<223> OTHER INFORMATION: cm
<220> FEATURE:
<221> NAME/KEY: modified_base
```

<222> LOCATION: (7)..(7)
<223> OTHER INFORMATION: 2'-O-methyl-uracil
<220> FEATURE:
<221> NAME/KEY: modified_base
<222> LOCATION: (8)..(8)
<223> OTHER INFORMATION: gm

<400> SEQUENCE: 64 ugauccug                                                                 8

<210> SEQ ID NO 65
<211> LENGTH: 10
<212> TYPE: DNA
<213> ORGANISM: Artificial
<220> FEATURE:
<223> OTHER INFORMATION: aptamer

<400> SEQUENCE: 65
acaggctacg                                                              10

<210> SEQ ID NO 66
<211> LENGTH: 9
<212> TYPE: DNA
<213> ORGANISM: Artificial
<220> FEATURE:
<223> OTHER INFORMATION: aptamer

<400> SEQUENCE: 66 tgatcctgt                                                                9

<210> SEQ ID NO 67
<211> LENGTH: 11
<212> TYPE: DNA
<213> ORGANISM: Artificial
<220> FEATURE:
<223> OTHER INFORMATION: aptamer

<400> SEQUENCE: 67
cacaggctac g                                                            11

<210> SEQ ID NO 68
<211> LENGTH: 10
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (7)..(7)
<223> OTHER INFORMATION: 2'-O-methyl-uracil

<400> SEQUENCE: 68
tgatccugtg                                                              10

<210> SEQ ID NO 69
<211> LENGTH: 8
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(6)
<223> OTHER INFORMATION: cm
<220> FEATURE:
<221> NAME/KEY: modified_base
<222> LOCATION: (8)..(8)
<223> OTHER INFORMATION: gm

```
<400> SEQUENCE: 69 tgatcctg                                                                 8

<210> SEQ ID NO 70
<211> LENGTH: 9
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: 2'-O-methyl-adenosine
<220> FEATURE:
<221> NAME/KEY: modified_base
<222> LOCATION: (3)..(4)
<223> OTHER INFORMATION: gm

<400> SEQUENCE: 70 caggctacg                                                                9

<210> SEQ ID NO 71
<211> LENGTH: 9
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (9)..(9)
<223> OTHER INFORMATION: 2'-O-methyl-uracil

<400> SEQUENCE: 71 tgatcctgu                                                                9

<210> SEQ ID NO 72
<211> LENGTH: 10
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(6)
<223> OTHER INFORMATION: cm
<220> FEATURE:
<221> NAME/KEY: modified_base
<222> LOCATION: (7)..(7)
<223> OTHER INFORMATION: 2'-O-methyl-uracil
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-O-methyl-uracil
<220> FEATURE:
<221> NAME/KEY: modified_base
<222> LOCATION: (10)..(10)
<223> OTHER INFORMATION: gm

<400> SEQUENCE: 72
tgatccugug                                                              10

<210> SEQ ID NO 73
<211> LENGTH: 9
```

```
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: gm

<400> SEQUENCE: 73 caggctacg                                                                  9

<210> SEQ ID NO 74
<211> LENGTH: 9
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (6)..(6)
<223> OTHER INFORMATION: 2'-O-methyl-uracil
<220> FEATURE:
<221> NAME/KEY: modified_base
<222> LOCATION: (9)..(9)
<223> OTHER INFORMATION: gm

<400> SEQUENCE: 74 caggcuacg                                                                  9

<210> SEQ ID NO 75
<211> LENGTH: 12
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-O-methyl-adenosine

<400> SEQUENCE: 75
cgtagagcat ca                                                             12

<210> SEQ ID NO 76
<211> LENGTH: 12
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
```

```
<223> OTHER INFORMATION: gm
<220> FEATURE:
<221> NAME/KEY: modified_base
<222> LOCATION: (10)..(10)
<223> OTHER INFORMATION: 2'-O-methyl-uracil
<220> FEATURE:
<221> NAME/KEY: modified_base
<222> LOCATION: (12)..(12)
<223> OTHER INFORMATION: 2'-O-methyl-adenosine

<400> SEQUENCE: 76
cgtagagcau ca                                                      12

<210> SEQ ID NO 77
<211> LENGTH: 9
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-O-methyl-uracil
<220> FEATURE:
<221> NAME/KEY: modified_base
<222> LOCATION: (8)..(8)
<223> OTHER INFORMATION: cm

<400> SEQUENCE: 77 caggcuacg                                                           9

<210> SEQ ID NO 78
<211> LENGTH: 12
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (3)..(3)
<223> OTHER INFORMATION: 2'-O-methyl-uracil
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: 2'-O-methyl-uracil
<220> FEATURE:
<221> NAME/KEY: modified_base
<222> LOCATION: (11)..(11)
<223> OTHER INFORMATION: cm

<400> SEQUENCE: 78
cguagagcau ca                                                      12

<210> SEQ ID NO 79
<211> LENGTH: 8
<212> TYPE: DNA
<213> ORGANISM: Artificial
<220> FEATURE:
<223> OTHER INFORMATION: aptamer
<220> FEATURE:
<221> NAME/KEY: modified_base
```

```
<222> LOCATION: (1)..(1)
<223> OTHER INFORMATION: 2'-O-methyl-uracil
<220> FEATURE:
<221> NAME/KEY: modified_base
<222> LOCATION: (4)..(4)
<223> OTHER INFORMATION: 2'-O-methyl-uracil
<220> FEATURE:
<221> NAME/KEY: modified_base
<222> LOCATION: (5)..(6)
<223> OTHER INFORMATION: cm
<220> FEATURE:
<221> NAME/KEY: modified_base
<222> LOCATION: (7)..(7)
<223> OTHER INFORMATION: 2'-O-methyl-uracil

<400> SEQUENCE: 79 ugauccug                                                                    8

<210> SEQ ID NO 80
<211> LENGTH: 8
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: 2'-O-methyl-uracil
<220> FEATURE:
<221> NAME/KEY: modified_base
<222> LOCATION: (8)..(8)
<223> OTHER INFORMATION: gm

<400> SEQUENCE: 80 tgatccug                                                                    8

<210> SEQ ID NO 81
<211> LENGTH: 11
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (11)..(11)
<223> OTHER INFORMATION: gm

<400> SEQUENCE: 81
cacaggctac g                                                               11

<210> SEQ ID NO 82
<211> LENGTH: 10
<212> TYPE: DNA
<213> ORGANISM: Artificial
<220> FEATURE:
<223> OTHER INFORMATION: aptamer

<400> SEQUENCE: 82
tgatcctgtg                                                                 10

<210> SEQ ID NO 83
<211> LENGTH: 10
<212> TYPE: DNA
<213> ORGANISM: Artificial
<220> FEATURE:
<223> OTHER INFORMATION: aptamer
<220> FEATURE:
```

```
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: 2'-O-methyl-uracil
<220> FEATURE:
<221> NAME/KEY: modified_base
<222> LOCATION: (9)..(9)
<223> OTHER INFORMATION: 2'-O-methyl-uracil
<220> FEATURE:
<221> NAME/KEY: modified_base
<222> LOCATION: (10)..(10)
<223> OTHER INFORMATION: gm

<400> SEQUENCE: 83
tgatccugug                                                          10

<210> SEQ ID NO 84
<211> LENGTH: 11
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (8)..(8)
<223> OTHER INFORMATION: 2'-O-methyl-uracil
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: gm

<400> SEQUENCE: 84
cacaggcuac g                                                        11

<210> SEQ ID NO 85
<211> LENGTH: 8
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: 2'-O-methyl-uracil
<220> FEATURE:
<221> NAME/KEY: modified_base
<222> LOCATION: (8)..(8)
<223> OTHER INFORMATION: gm

<400> SEQUENCE: 85 tgatccug                                                            8

<210> SEQ ID NO 86
<211> LENGTH: 11
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (11)..(11)
<223> OTHER INFORMATION: gm
```

<400> SEQUENCE: 86
cccaggctac g											11

<210> SEQ ID NO 87
<211> LENGTH: 10
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (8)..(10)
<223> OTHER INFORMATION: gm

<400> SEQUENCE: 87 tgatcctggg											10

<210> SEQ ID NO 88
<211> LENGTH: 10
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (8)..(10)
<223> OTHER INFORMATION: gm

<400> SEQUENCE: 88 tgatcctggg											10

<210> SEQ ID NO 89
<211> LENGTH: 10
<212> TYPE: DNA
<213> ORGANISM: Artificial
<220> FEATURE:
<223> OTHER INFORMATION: aptamer

<400> SEQUENCE: 89 tgatcctggg											10

<210> SEQ ID NO 90
<211> LENGTH: 10
<212> TYPE: DNA
<213> ORGANISM: Artificial
<220> FEATURE:
<223> OTHER INFORMATION: aptamer
<220> FEATURE:
<221> NAME/KEY: modified_base
<222> LOCATION: (5)..(5)
<223> OTHER INFORMATION: cm

<400> SEQUENCE: 90 tgatcctggg											10

<210> SEQ ID NO 91
<211> LENGTH: 88
<212> TYPE: DNA
<213> ORGANISM: Artificial
<220> FEATURE:
<223> OTHER INFORMATION: pool
<220> FEATURE:
<221> NAME/KEY: misc_feature
<222> LOCATION: (25)..(64)

-continued

<223> OTHER INFORMATION: n is a, c, g, t or u

<400> SEQUENCE: 91
gggaaaagcg aaucauacac aagannnnnn nnnnnnnnnn nnnnnnnnnn    60
nnnngcuccg ccagagacca accgagaa    88

<210> SEQ ID NO 92
<211> LENGTH: 41
<212> TYPE: DNA
<213> ORGANISM: Artificial
<220> FEATURE:
<223> OTHER INFORMATION: aptamer

<400> SEQUENCE: 92
taatacgact cactataggg aaaagcgaat catacacaag a    41

<210> SEQ ID NO 93
<211> LENGTH: 24
<212> TYPE: DNA
<213> ORGANISM: Artificial
<220> FEATURE:
<223> OTHER INFORMATION: aptamer

<400> SEQUENCE: 93
ttctcggttg gtctctggcg gagc    24

<210> SEQ ID NO 94
<211> LENGTH: 87
<212> TYPE: DNA
<213> ORGANISM: Artificial
<220> FEATURE:
<223> OTHER INFORMATION: aptamer

<400> SEQUENCE: 94
gggaaaagcg aatcatacac aagatcgcca ggagcaaagt cacggaggag tggggtacg    60 aatgctccgc cagagaccaa ccgagaa    87

<210> SEQ ID NO 95
<211> LENGTH: 88
<212> TYPE: DNA
<213> ORGANISM: Artificial
<220> FEATURE:
<223> OTHER INFORMATION: aptamer

<400> SEQUENCE: 95
gggaaaagcg aatcatacac aagaccggga actcggattc ttcgcatgtg gatgcgatca    60
gtatgctccg ccagagacca accgagaa    88

<210> SEQ ID NO 96
<211> LENGTH: 88
<212> TYPE: DNA
<213> ORGANISM: Artificial
<220> FEATURE:
<223> OTHER INFORMATION: aptamer

<400> SEQUENCE: 96
gggaaaagcg aatcatacac aagaccggga actcggattc ttcacatgtg gatgtgatca    60
gtatgctccg ccagagacca accgagaa    88

<210> SEQ ID NO 97
<211> LENGTH: 88
<212> TYPE: DNA
<213> ORGANISM: Artificial

```
<220> FEATURE:
<223> OTHER INFORMATION: aptamer

<400> SEQUENCE: 97
gggaaaagcg aatcatacac aagaccggaa actcggattc ttcgcatgtg gatgcgatca    60
gtatgctccg ccagagacca accgagaa                                      88

<210> SEQ ID NO 98
<211> LENGTH: 88
<212> TYPE: DNA
<213> ORGANISM: Artificial
<220> FEATURE:
<223> OTHER INFORMATION: aptamer

<400> SEQUENCE: 98
gggaaaagcg aatcatacac aagagagtgg aggaggtatg tatggtttgt gcgtctggtg    60
cggtgctccg ccagagacca accgagaa                                      88
```

APTAMERS COMPRISING CPG MOTIFS

REFERENCE TO RELATED APPLICATIONS

This non-provisional patent application is a continuation-in-part of U.S. Ser. No. 10/718,833, filed Nov. 21, 2003, which claims priority to U.S. Ser. No. 60/428,102, filed Nov. 21, 2002 and U.S. Ser. No. 60/469,628, filed on May 8, 2003; is a continuation in part of U.S. Ser. No. 10/826,077, filed on Apr. 15, 2004; and this patent application claims priority under 35 U.S.C. § 119(e) to the following provisional applications: U.S. Ser. No. 60/464,239, filed Apr. 21, 2003; U.S. Ser. No. 60/465,053, filed Apr. 23, 2003; U.S. Ser. No. 60/474,133, filed May 29, 2003; U.S. Ser. No. 60/486,580, filed Jul. 11, 2003; U.S. Ser. No. 60/489,810, filed Jul. 23, 2003; U.S. Ser. No. 60/503,596, filed Sep. 16, 2003; and. U.S. Ser. No. 60/523,935, filed Nov. 21, 2003; each of which is herein incorporated by reference in its entirety.

FIELD OF THE INVENTION

The invention relates generally to the field of nucleic acids and more particularly to aptamers capable of binding to platelet derived growth factor ("PDGF") useful as therapeutics in oncology and/or other diseases or disorders in which PDGF has been implicated. The invention further relates to materials and methods for the administration of aptamers capable of binding to platelet derived growth factor.

BACKGROUND OF THE INVENTION

Aptamers are nucleic acid molecules having specific binding affinity to molecules through interactions other than classic Watson-Crick base pairing.

Aptamers, like peptides generated by phage display or monoclonal antibodies (MAbs), are capable of specifically binding to selected targets and, through binding, block their targets' ability to function. Created by an in vitro selection process from pools of random sequence oligonucleotides (FIG. 1), aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

Aptamers have a number of desirable characteristics for use as therapeutics (and diagnostics) including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial (therapeutic) leads. In vitro selection allows the specificity and affinity of the aptamer to be tightly controlled and allows the generation of leads against both toxic and non-immunogenic targets.
2) Toxicity and Immunogenicity. Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers (most likely because aptamers cannot be presented by T-cells via the MHC and the immune response is generally trained not to recognize nucleic acid fragments).
3) Administration. Whereas all currently approved antibody therapeutics are administered by intravenous infusion (typically over 2-4 hours), aptamers can be administered by subcutaneous injection. This difference is primarily due to the comparatively low solubility and thus large volumes necessary for most therapeutic MAbs. With good solubility (>150 mg/ml) and comparatively low molecular weight (aptamer: 10-50 kDa; antibody: 150 kDa), a weekly dose of aptamer may be delivered by injection in a volume of less than 0.5 ml. Aptamer bioavailability via subcutaneous administration is >80% in monkey studies (Tucker et al., J. Chromatography B. 732: 203-212, 1999). In addition, the small size of aptamers allows them to penetrate into areas of conformational constrictions that do not allow for antibodies or antibody fragments to penetrate, presenting yet another advantage of aptamer-based therapeutics or prophylaxis.
4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale synthesizer can produce upwards of 100 kg oligonucleotide per year and requires a relatively modest initial investment. The current cost of goods for aptamer synthesis at the kilogram scale is estimated at $500/g, comparable to that for highly optimized antibodies. Continuing improvements in process development are expected to lower the cost of goods to <$100/g in five years.
5) Stability. Therapeutic aptamers are chemically robust. They are intrinsically adapted to regain activity following exposure to heat, denaturants, etc. and can be stored for extended periods (>1 yr) at room temperature as lyophilized powders. In contrast, antibodies must be stored refrigerated.

Interstitial Fluid Pressure

The three most common types of cancer treatment are surgical removal of cancerous tissue, radiotherapy to obliterate cancerous tissue, and chemotherapy. These treatments are aimed at removing the cancerous tissues or cells or destroying them in the body with therapeutics or other agents. Chemotherapy remains a major treatment modality for solid tumors. To potentially reduce toxic side effects and to achieve higher efficacy of chemotherapeutic drugs, strategies to improve distribution of drugs between normal tissues and tumors are highly desirable.

A major obstacle in the treatment of solid tumors is the limited uptake of therapeutic agents into tumor tissue. Elevated interstitial fluid pressure ("IFP") is one of the physiologically distinctive properties of solid tumors that differ from healthy connective tissue and is considered to be the main obstacle limiting free diffusion of therapeutics into solid tumors. PDGF receptors, particularly PDGF-β, have been implicated in the regulation of IFP. As a tumor enters a hyperproliferative state, blood supplying oxygen and other nutrients cannot keep up with the tumors' demands and a state of hypoxia results. Hypoxia triggers an "angiogenic switch" which will up-regulate the expression of several factors including VEGF and PDGF which in turn serve to initiate angiogenesis. However, the angiogenesis that results forms an abnormal tumor vasculature. The tumor vasculature becomes impaired to the point of being unable to adequately drain excess fluid from the interstitium and fluid accumulation distends the elastic interstitial matrix causing an increase in pressure. When pressure exceeds capillary wall resistance, compression occurs and blood flow resistance increases.

This property of most solid tumors—tumor interstitial hypertension or increased IFP—has been suggested as a potential target for efforts to increase tumor drug uptake (Jain et al., (1987) Cancer Res., 47:3039-3051). Increased IFP acts as a barrier for tumor transvascular transport (Jain et al. (1997), Adv. Drug Deliv. Rev. 26:71-90). Lessening of tumor IFP, or modulation of microvascular pressure, has been shown to increase transvascular transport of tumor-targeting antibodies or low-molecular weight tracer compounds (Pietras et al., (2001), Cancer Res., 61, 2929-2934). The etiology of interstitial hypertension in tumors is poorly understood. One proposed theory is that the lack of lymphatic vessels in tumors is a contributing factor to the increased tumor IFP (Jain et al., (1987), Cancer Res., 47:3039-3051). Another proposed theory is that the microvasculature and the supporting stroma compartment are likely to be important determinants for tumor IFP (Pietras et al., (2002) Cancer Res., 62: 5476-5484). Accumulating evidence points toward the transmembrane PDGF β-receptor tyrosine kinase as a potential target for pharmacological therapeutics to modulate tumor interstitial hypertension. Among other potential targets are growth factors that bind to the PDGF β-receptor.

PDGF Mediated Cancer

In addition to IFP and the difficulty of penetrating tumors with therapeutics, another obstacle in cancer treatment are mutations in certain forms of cancer by PDGF mediated cancer leading to constitutive expression of PDGF. These mutations drive abnormal proliferation of cells which results in the various forms of cancer as shown in FIG. 3 (Pietras et al., (2001), Cancer Res., 61, 2929-2934). A gene mutation results in amplification of PDGF α-receptors in high grade glioblastomas. In chronic myelomonocytic leukemia (CMML), constitutive activation of PDGF-β receptors results from a mutation which causes the fusion of β-receptors with proteins other than PDGF (Golub et al., (1994) Cell 77, 307-316, Magnusson et al., (2001) Blood 100, 623-626). Constitutive activation of PDGF-α-receptor due to activating point mutations has also been identified in patients with gastrointestinal stromal tumors (GIST) (Heinreich et al., (2003) Science 299, 708-710). Dermatofibrosarcoma protuberans (DFSP) is associated with constitutive production of fusion proteins which are processed to PDGF-BB (O'Brian et al., (1998) Gene Chrom. Cancer 23, 187-193; Shimiziu et al. (1999) Cancer Res. 59, 3719-3723; Simon et al. (1997) Nat. Genet., 15, 95-98). In addition to the constitutive activation of PDGF ligand and/or receptor due to mutations, up regulation has been shown in soft tissue sarcomas and gliomas (Ostman and Heldin, (2001), Adv. Cancer Res. 80, 1-38).

PDGF

Growth factors are substances that have a cell-proliferative effect on cells or tissues. Any given growth factor may have more than one receptor or induce cell proliferation in more than one cell line or tissue. PDGF belongs to the cysteine-knot growth factor family and was originally isolated from platelets for promoting cellular mitogenic and migratory activity. PDGF is a strong mitogen and has a pivotal role in regulation of normal cell proliferation such as fibroblasts, smooth muscle cells, neuroglial cells and connective-tissue cells. In addition, PDGF mediates pathological cell growth such as in proliferative disorders, and also plays a role in angiogenesis. Another growth factor involved in tumor angiogenesis is vascular endothelial growth factor (VEGF).

Four PDGF polypeptide chains have been identified which are currently known to make up five dimeric PDGF isoforms: PDGF-AA, -BB, -CC, -DD, and -AB. The most abundant species are PDGF AB and BB. PDGF isoforms bind to α and β tyrosine kinase receptors. PDGF receptors are expressed by many different cell types within tumors. The binding of PDGF isoforms to their cognate receptors induces the dimerization and subsequent phosphorylation of specific residues in the intracellular tyrosine kinase domain of the receptors and activation of the signaling pathway. PDGF isoforms -AA, -BB, -CC, and -AB induce PDGF α-receptor dimerization. PDGF-BB and PDGF-DD activate PDGF β receptor dimerization. All isoforms of PDGF except PDGF-AA activate both α and β receptors in cells which co-express both receptor types (FIG. 2). Because they are potent mitogens, PDGF isoforms have been targeted for proliferative disease therapeutics development, such as cancer, diabetic retinopathy, glomerulonephritis, and restenosis.

PDGF, which is secreted by endothelial cells, acts as direct mitogen for fibroblasts, recruits pericytes and stimulates vascular smooth muscle cells. Many solid tumors display paracrine signaling of PDGF in the tumor stroma. PDGF is known to up-regulate synthesis of collagen and to mediate interactions of anchor proteins such as integrins with extracellular matrix (ECM) components. PDGF interactions between connective tissue, ECM and intracellular actin filament systems cause increased tensile strength which contributes to high IFP. High IFP is localized to the site of tumor and is associated with poor prognosis in human cancers as it increases with tumor size and severity and the grade of malignancy. The role of PDGF signaling in control of IFP and the up-regulated expression in various solid tumors, has prompted investigation into whether the inhibition of PDGF signaling can decrease IFP and thereby increase drug uptake into solid tumors. Previous work has demonstrated that inhibition of PDGF signaling with small molecule receptor antagonists and a PDGF specific aptamer decreases interstitial fluid pressure and increases the uptake of chemotherapeutics into solid tumors (Pietras et al., (2001), Cancer Res., 61: 2929-2934).

Accordingly, it would be beneficial to have novel materials and methods in oncology therapy to reduce tumor IFP, decrease tumor angiogenesis, and reduce the deleterious effects of mutation by the constitutive expression of PDGF. The present invention provides materials and methods to meet these and other needs.

BRIEF DESCRIPTION OF THE DRAWINGS

FIG. 24 is a graph depicting the inhibitory effect of various PDGF-AA aptamers of the invention (ARX33P1.D2, ARX33P1.E5, and ARX33P1.E10) on PDGF-AA induced 3T3 cell proliferation.

FIG. 25 is a graph depicting the effect of PDGF-AA aptamers on PDGF-BB induced 3T3 cell proliferation.

SUMMARY OF THE INVENTION

Figure 1:
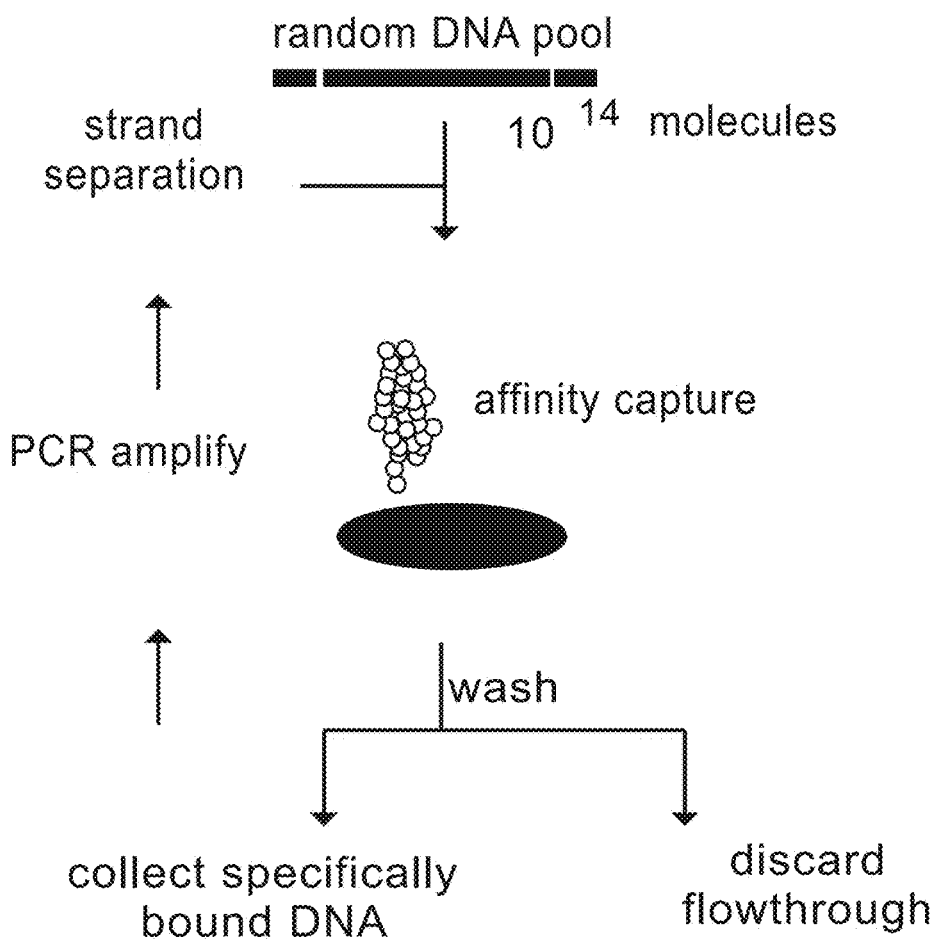
FIG. 1 is a schematic representation of the in vitro aptamer selection (SELEX™) process from pools of random sequence oligonucleotides.
Figure 2:
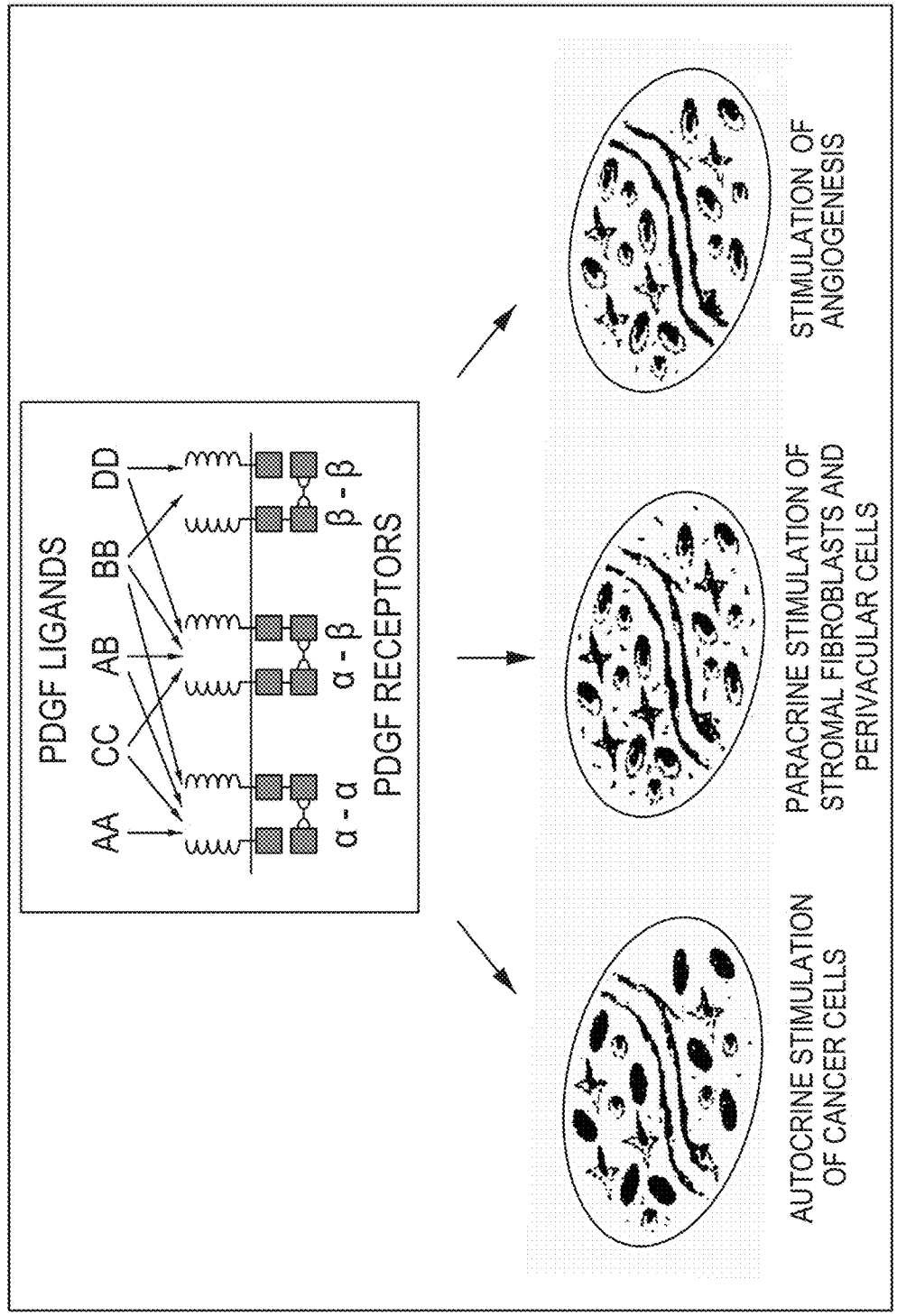
FIG. 2 is a schematic of isoforms AA, BB, CC, DD, and AB of PDGF and cognate receptors.
Figure 3:
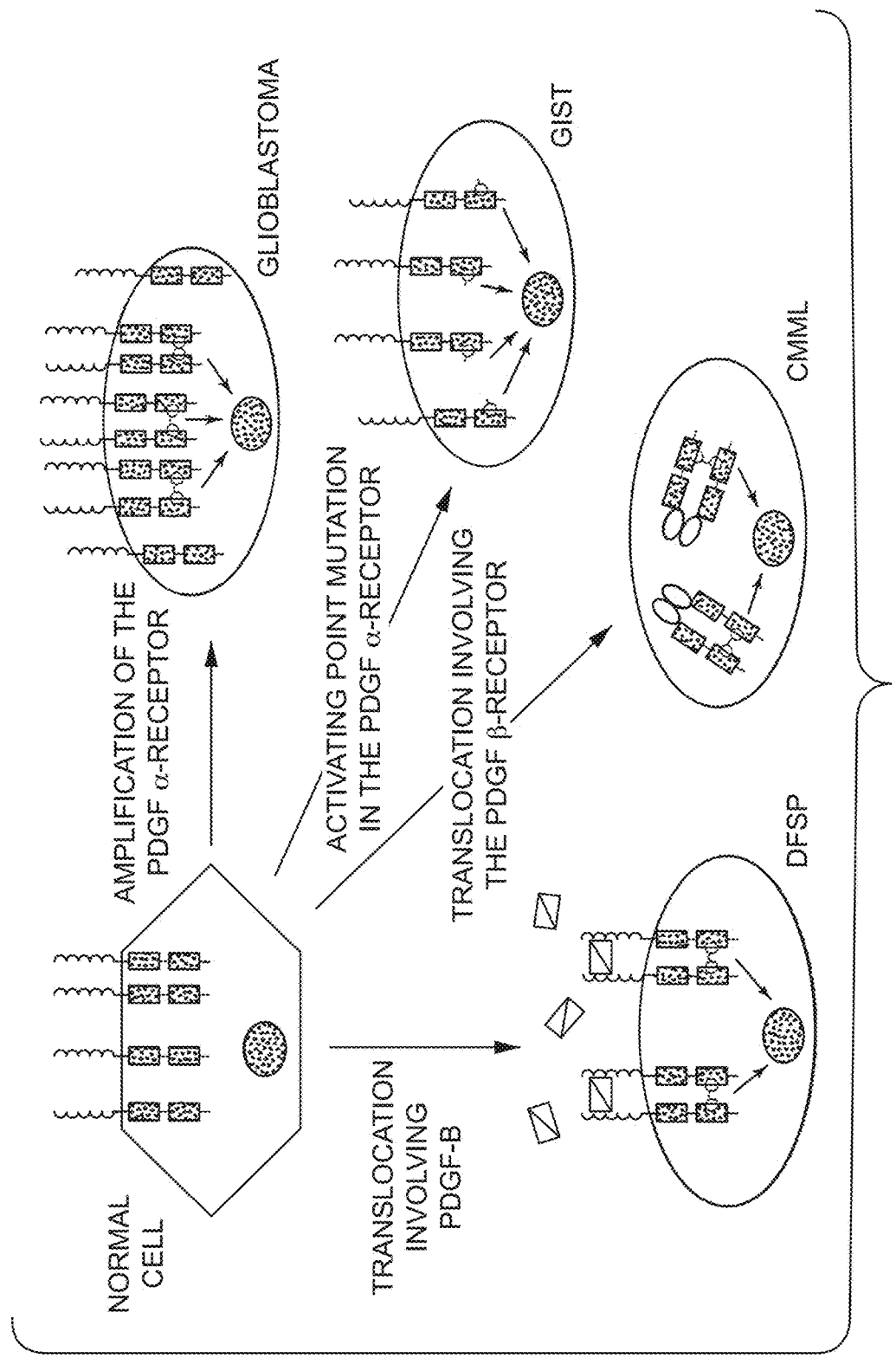
FIG. 3 is a schematic of gene mutations that give rise to constitutive PDGF receptor signaling in cancer cells found in glioblastomas, chronic myelomonocytic leukemia (CMML), dermatofibrosarcoma protuberans (DFSP), gastrointestinal stromal tumors (GIST), and other soft tissue sarcomas.

The present invention provides materials and methods for the treatment of cancer, solid tumor cancers in particular, by the administration to patients of therapeutically effective amounts of aptamers or aptamer compositions capable of binding with great affinity and specificity to platelet derived growth factor, vascular endothelial growth factor, their isoforms, their receptors, or any combination thereof, thus inhibiting the bound ligand's biological role in cancer etiology. The aptamers of the present invention may be used with known chemotherapeutic cytotoxic agents and may include one or more CpG motifs embedded therein or appended thereto.

The present invention provides aptamers that bind to PDGF. In one embodiment, the aptamers that bind to PDGF include a nucleic acid sequence selected from SEQ ID NO:1 to SEQ ID NO:3, SEQ ID NO:9 to SEQ ID NO:38, SEQ ID NO:50, SEQ ID NO:54 to SEQ ID NO:90, and SEQ ID NO:94 to SEQ ID NO:99. In one embodiment, the oligonucleotide sequence of the aptamer contains less than seven nucleotides having a 2' fluoro substituent.

The invention also provides aptamers that include a first sequence that binds to a first target and a second sequence that binds to a second target. In one embodiment, the first target is PDGF, PDGF-isoforms, or PDGF receptor, and the second target is VEGF or VEGF receptor. The PDGF isoforms are, for example, PDGF BB, PDGF AB, PDGF CC, and PDGF DD. In one embodiment, the aptamers that bind to PDGF include a nucleic acid sequence selected from SEQ ID NO:1 to SEQ ID NO:3, SEQ ID NO:9 to SEQ ID NO:38, SEQ ID NO:50, SEQ ID NO:54 to SEQ ID NO:90, and SEQ ID NO:94 to SEQ ID NO:99.

In one embodiment, the first target does not, upon binding of the aptamer, stimulate an immune response, and moreover, the second target does, upon binding of the aptamer, stimulate an immune response. In one embodiment, the second target is a toll-like receptor. In another embodiment, the second sequence is an immunostimulatory sequence. In one embodiment, the immunostimulatory sequence is a CpG motif.

In one embodiment, the first sequence is capable of binding to one of the following targets: PDGF, IgE, IgE Fcε R1, PSMA, CD22, TNF-alpha, CTLA4, PD-1, PD-L1, PD-L2, FcRIIB, BTLA, TIM-3, CD11c, BAFF, B7-X, CD19, CD20, CD25, and CD33. In one embodiment, the first sequence is capable of binding to PDGF.

The present invention also provides compositions that contain a PDGF-binding aptamer of the invention and a pharmaceutically acceptable carrier.

In one embodiment, the compositions of the invention include a PDGF-binding aptamer of the invention, a cytotoxic agent and a pharmaceutically acceptable carrier. In one embodiment, the cytotoxic agent belongs to a class of cytotoxic agents such as tubulin stabilizers, tubulin destabilizers, anti-metabolites, purine synthesis inhibitors, nucleoside analogs, DNA alkylating agents, DNA modifying agents, and vascular disrupting agents. In one embodiment, the cytotoxic agent is used alone or in combinations with one or more cytotoxic agents selected from the group consisting of calicheamycin, doxorubicin, taxol, methotrexate, gemcitabine, cytarabine, vinblastin, daunorubicin, docetaxel, irinotecan, epothilone B, epothilone D, cisplatin, carboplatin, and 5-fluoro-U.

The invention also provides compositions that include a PDGF-binding aptamer of the invention, a VEGF-binding aptamer and a pharmaceutically acceptable carrier. In one embodiment, these compositions also include a cytotoxic agent. Suitable cytotoxic agents include agents belonging to a class of cytotoxic agents selected from the group consisting of tubulin stabilizers, tubulin destabilizers, anti-metabolites, purine synthesis inhibitors, nucleoside analogs, DNA alkylating agents, DNA modifying agents, and vascular disrupting agents. The cytotoxic agent is used alone or in combinations of one or more cytotoxic agents selected from the group consisting of calicheamycin, doxorubicin, taxol, methotrexate, gemcitabine, cytarabine, vinblastin, daunorubicin, docetaxel, irinotecan, epothilone B, epothilone D, cisplatin, carboplatin, and 5-fluoro-U.

The invention also provides methods of treating cancer by administering a therapeutically effective amount of a PDGF-binding aptamer of the invention. The invention also provides methods of treating cancer by administering a therapeutically effective amount of a composition of the invention.

In one embodiment, the cancer or tumor is PDGF mediated cancer or tumor. In one embodiment, the PDGF mediated cancer or tumor is a glioblastoma, chronic myelomonocytic leukemia, a dermafibrosarcoma protuberan, a gastrointestinal stromal tumor or a soft tissue sarcoma.

In one embodiment, the composition includes a cytotoxic agent that belongs to a class of cytotoxic agents selected from the group consisting of tubulin stabilizers, tubulin destabilizers, anti-metabolites, purine synthesis inhibitors, nucleoside analogs, DNA alkylating agents, DNA modifying agents, and vascular disrupting agents. In one embodiment, the cytotoxic agent is used alone or in combinations of one or more cytotoxic agents such as calicheamycin, doxorubicin, taxol, methotrexate, gemcitabine, cytarabine, vinblastin, daunorubicin, docetaxel, irinotecan, epothilone B, epothilone D, cisplatin, carboplatin, and 5-fluoro-U.

The invention also provides methods of inhibiting growth of a solid tumor by administering a therapeutically effective amount of a PDGF-binding aptamer of the invention. The invention also provides methods of inhibiting growth of a solid tumor by administering a therapeutically effective amount of a composition of the invention.

In one embodiment, the cancer or tumor is PDGF mediated cancer or tumor. In one embodiment, the PDGF mediated cancer or tumor is a glioblastoma, chronic myelomonocytic leukemia, a dermafibrosarcoma protuberan, a gastrointestinal stromal tumor or a soft tissue sarcoma.

In one embodiment, the composition includes a cytotoxic agent belonging to a class of cytotoxic agents selected from the group consisting of tubulin stabilizers, tubulin destabilizers, anti-metabolites, purine synthesis inhibitors, nucleoside analogs, DNA alkylating agents, DNA modifying agents, and vascular disrupting agents. In one embodiment, the cytotoxic agent is used alone or in combinations of one or more cytotoxic agents such as calicheamycin, doxorubicin, taxol, methotrexate, gemcitabine, cytarabine, vinblastin, daunorubicin, docetaxel, irinotecan, epothilone B, epothilone D, cisplatin, carboplatin, and 5-fluoro-U.

The invention also provides methods of reducing IFP in a solid tumor by administering a therapeutically effective amount of a PDGF-binding aptamer of the invention. The invention also provides methods of reducing IFP in a solid tumor by administering a therapeutically effective amount of a composition of the invention.

In one embodiment, the cancer or tumor is PDGF mediated cancer or tumor. In one embodiment, the PDGF mediated cancer or tumor is a glioblastoma, chronic myelomonocytic leukemia, a dermafibrosarcoma protuberan, a gastrointestinal stromal tumor or a soft tissue sarcoma.

In one embodiment, the composition includes a cytotoxic agent belonging to a class of cytotoxic agents selected from the group consisting of tubulin stabilizers, tubulin destabilizers, anti-metabolites, purine synthesis inhibitors, nucleoside analogs, DNA alkylating agents, DNA modifying agents, and vascular disrupting agents. In one embodiment, the cytotoxic agent is used alone or in combinations of one or more cytotoxic agents such as calicheamycin, doxorubicin, taxol, methotrexate, gemcitabine, cytarabine, vinblastin, daunorubicin, docetaxel, irinotecan, epothilone B, epothilone D, cisplatin, carboplatin, and 5-fluoro-U.

The invention also provides methods of increasing the permeability of a solid tumor to cytotoxic agents by administering a therapeutically effective amount of a PDGF-binding aptamer of the invention. The invention also provides methods of increasing the permeability of a solid tumor to cytotoxic agents by administering a therapeutically effective amount of a composition of the invention.

In one embodiment, the cancer or tumor is PDGF mediated cancer or tumor. In one embodiment, the PDGF mediated cancer or tumor is a glioblastoma, chronic myelomonocytic leukemia, a dermafibrosarcoma protuberan, a gastrointestinal stromal tumor or a soft tissue sarcoma.

In one embodiment, the composition includes a cytotoxic agent belonging to a class of cytotoxic agents selected from the group consisting of tubulin stabilizers, tubulin destabilizers, anti-metabolites, purine synthesis inhibitors, nucleoside analogs, DNA alkylating agents, DNA modifying agents, and vascular disrupting agents. In one embodiment, the cytotoxic agent is used alone or in combinations of one or more cytotoxic agents such as calicheamycin, doxorubicin, taxol, methotrexate, gemcitabine, cytarabine, vinblastin, daunorubicin, docetaxel, irinotecan, epothilone B, epothilone D, cisplatin, carboplatin, and 5-fluoro-U.

The invention also provides methods of reducing constitutive expression of platelet derived growth factor in a tumor by administering a therapeutically effective amount of a PDGF-binding aptamer of the invention. The invention also provides methods of reducing constitutive expression of platelet derived growth factor in a tumor by administering a therapeutically effective amount of a composition of the invention.

In one embodiment, the cancer or tumor is PDGF mediated cancer or tumor. In one embodiment, the PDGF mediated cancer or tumor is a glioblastoma, chronic myelomonocytic leukemia, a dermafibrosarcoma protuberan, a gastrointestinal stromal tumor or a soft tissue sarcoma.

In one embodiment, the composition includes a cytotoxic agent belonging to a class of cytotoxic agents selected from the group consisting of tubulin stabilizers, tubulin destabilizers, anti-metabolites, purine synthesis inhibitors, nucleoside analogs, DNA alkylating agents, DNA modifying agents, and vascular disrupting agents. In one embodiment, the cytotoxic agent is used alone or in combinations of one or more cytotoxic agents such as calicheamycin, doxorubicin, taxol, methotrexate, gemcitabine, cytarabine, vinblastin, daunorubicin, docetaxel, irinotecan, epothilone B, epothilone D, cisplatin, carboplatin, and 5-fluoro-U.

The invention also provides methods of reducing angiogenesis and neovascularization in a tumor by administering a therapeutically effective amount of a PDGF-binding aptamer of the invention. The invention also provides methods of reducing angiogenesis and neovascularization in a tumor by administering a therapeutically effective amount of a composition of the invention.

In one embodiment, the cancer or tumor is PDGF mediated cancer or tumor. In one embodiment, the PDGF mediated cancer or tumor is a glioblastoma, chronic myelomonocytic leukemia, a dermafibrosarcoma protuberan, a gastrointestinal stromal tumor or a soft tissue sarcoma.

In one embodiment, the composition includes a cytotoxic agent belonging to a class of cytotoxic agents selected from the group consisting of tubulin stabilizers, tubulin destabilizers, anti-metabolites, purine synthesis inhibitors, nucleoside analogs, DNA alkylating agents, DNA modifying agents, and vascular disrupting agents. In one embodiment, the cytotoxic agent is used alone or in combinations of one or more cytotoxic agents such as calicheamycin, doxorubicin, taxol, methotrexate, gemcitabine, cytarabine, vinblastin, daunorubicin, docetaxel, irinotecan, epothilone B, epothilone D, cisplatin, carboplatin, and 5-fluoro-U.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The SELEX™ Method

A suitable method for generating an aptamer is with the process entitled "Systematic Evolution of Ligands by Exponential Enrichment" ("SELEX™") generally depicted in FIG. 1. The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX-identified nucleic acid ligand is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

SELEX™ relies as a starting point upon a large library of single stranded oligonucleotide templates comprising randomized sequences derived from chemical synthesis on a standard DNA synthesizer. In some examples, a population of 100% random oligonucleotides is screened. In others, each oligonucleotide in the population comprises a random sequence and at least one fixed sequence at its 5' and/or 3' end which comprises a sequence shared by all the molecules of the oligonucleotide population. Fixed sequences include sequences such as hybridization sites for PCR primers, promoter sequences for RNA polymerases (e.g., T3, T4, T7, SP6, and the like), restriction sites, or homopolymeric sequences, such as poly A or poly T tracts, catalytic cores, sites for selective binding to affinity columns, and other sequences to facilitate cloning and/or sequencing of an oligonucleotide of interest.

The random sequence portion of the oligonucleotide can be of any length and can comprise ribonucleotides and/or deoxyribonucleotides and can include modified or non-natural nucleotides or nucleotide analogs. See, e.g., U.S. Pat. Nos. 5,958,691; 5,660,985; 5,958,691; 5,698,687; 5,817, 635; and 5,672,695, PCT publication WO 92/07065. Random oligonucleotides can be synthesized from phosphodiester-linked nucleotides using solid phase oligonucleotide synthesis techniques well known in the art (Froehler et al., Nucl. Acid Res. 14:5399-5467 (1986); Froehler et al., Tet. Lett. 27:5575-5578 (1986)). Oligonucleotides can also be synthesized using solution phase methods such as triester synthesis methods (Sood et al., Nucl. Acid Res. 4:2557 (1977); Hirose et al., Tet. Lett., 28:2449 (1978)). Typical syntheses carried out on automated DNA synthesis equipment yield $10^{15}$-$10^{17}$ molecules. Sufficiently large regions of random sequence in the sequence design increases the likelihood that each synthesized molecule is likely to represent a unique sequence.

To synthesize randomized sequences, mixtures of all four nucleotides are added at each nucleotide addition step during the synthesis process, allowing for random incorporation of nucleotides. In one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

Template molecules typically contain fixed 5' and 3' terminal sequences which flank an internal region of 30-50 random nucleotides. A standard (1 µmole) scale synthesis will yield $10^{15}$-$10^{16}$ individual template molecules, sufficient for most SELEX experiments. The RNA library is generated from this starting library by in vitro transcription using recombinant T7 RNA polymerase. This library is then mixed with the target under conditions favorable for binding and subjected to step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

Within a nucleic acid mixture containing a large number of possible sequences and structures, there is a wide range of binding affinities for a given target. A nucleic acid mixture comprising, for example a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain sub portions of conserved sequence incorporated with randomized sequence. Sequence variation in test nucleic acids can be introduced or increased by mutagenesis before or during the selection/amplification iterations.

In one embodiment of SELEX™, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20-50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photoreactive groups capable of binding and/or photocrosslinking to and/or photoinactivating a target molecule. U.S. Pat. No. 5,567,588 and U.S. application Ser. No. 08/792,075, filed Jan. 31, 1997, entitled "Flow Cell SELEX", describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

SELEX™ can also be used to obtain nucleic acid ligands that bind to more than one site on the target molecule, and to obtain nucleic acid ligands that include non-nucleic acid species that bind to specific sites on the target. SELEX™ provides means for isolating and identifying nucleic acid ligands which bind to any envisionable target, including large and small biomolecules including proteins (including both nucleic acid-binding proteins and proteins not known to bind nucleic acids as part of their biological function) cofactors and other small molecules. For example, see U.S. Pat. No. 5,580,737 which discloses nucleic acid sequences identified through SELEX™ which are capable of binding with high affinity to caffeine and the closely related analog, theophylline.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of a) preparing a candidate mixture of nucleic acids; b) contacting the candidate mixture with the target, wherein nucleic acids having an increased affinity to the target relative to the candidate mixture may be partitioned from the remainder of the candidate mixture; c) partitioning the increased affinity nucleic acids from the remainder of the candidate mixture; d) contacting the increased affinity nucleic acids with one or more non-target molecules such that nucleic acid ligands with specific affinity for the non-target molecule(s) are removed; and e) amplifying the nucleic acids with specific affinity to the target molecule to yield a mixture of nucleic acids enriched for nucleic acid sequences with a relatively higher affinity and specificity for binding to the target molecule.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985, which describes oligonucleotides containing nucleotide derivatives chemically modified at the 2' position of ribose, 5 position of pyrimidines, and 8 position of purines. U.S. Pat. No. 5,756,703 describes oligonucleotides containing various 2'-modified pyrimidines. U.S. Pat. No. 5,580,737 describes highly specific nucleic acid ligands containing one or more nucleotides modified with 2'-amino (2'-NH$_2$), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

The SELEX method encompasses combining selected oligonucleotides with other selected oligonucleotides and non-oligonucleotide functional units as described in U.S. Pat. No. 5,637,459 and U.S. Pat. No. 5,683,867. The SELEX method further encompasses combining selected nucleic acid ligands with lipophilic or non-immunogenic high molecular weight compounds in a diagnostic or therapeutic complex, as described in U.S. Pat. No. 6,011,020. VEGF nucleic acid ligands that are associated with a lipophilic compound, such as diacyl glycerol or dialkyl glycerol, in a diagnostic or therapeutic complex are described in U.S. Pat. No. 5,859,228.

VEGF nucleic acid ligands that are associated with a lipophilic compound, such as a glycerol lipid, or a non-immunogenic high molecular weight compound, such as polyalkylene glycol are further described in U.S. Pat. No. 6,051,698. VEGF nucleic acid ligands that are associated with a non-immunogenic, high molecular weight compound or a lipophilic compound are further described in PCT Publication No. WO 98/18480. These patents and applications allow the combination of a broad array of shapes and other properties, and the efficient amplification and replication properties, of oligonucleotides with the desirable properties of other molecules.

The identification of nucleic acid ligands to small, flexible peptides via the SELEX method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified.

To generate oligonucleotide populations which are resistant to nucleases and hydrolysis, modified oligonucleotides can be used and can include one or more substitute internucleotide linkages, altered sugars, altered bases, or combinations thereof. In one embodiment, oligonucleotides are provided in which the P(O)O group is replaced by P(O)S ("thioate"), P(S)S ("dithioate"), P(O)NR$_2$ ("amidate"), P(O) R, P(O)OR', CO or CH$_2$ ("formacetal") or 3'-amine (—NH—CH$_2$—CH$_2$—), wherein each R or R' is independently H or substituted or unsubstituted alkyl. Linkage groups can be attached to adjacent nucleotide through an —O—, —N—, or —S— linkage. Not all linkages in the oligonucleotide are required to be identical.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). The use of 2-fluoro-ribonucleotide oligomer molecules can increase the sensitivity of a nucleic acid molecule for a target molecule by ten-to-one hundred-fold over those generated using unsubstituted ribo- or deoxyribooligonucleotides (Pagratis, et al., Nat. Biotechnol. 15:68-73 (1997)), providing additional binding interactions with a target molecule and increasing the stability of the secondary structure(s) of the nucleic acid molecule (Kraus, et al., Journal of Immunology 160:5209-5212 (1998); Pieken, et al., Science 253:314-317 (1991); Lin, et al., Nucl. Acids Res. 22:5529-5234 (1994); Jellinek, et al. Biochemistry 34:11363-11372 (1995); Pagratis, et al., Nat. Biotechnol 15:68-73 (1997)).

Nucleic acid aptamer molecules are generally selected in a 5 to 20 cycle procedure. In one embodiment, heterogeneity is introduced only in the initial selection stages and does not occur throughout the replicating process.

The starting library of DNA sequences is generated by automated chemical synthesis on a DNA synthesizer. This library of sequences is transcribed in vitro into RNA using T7 RNA polymerase or modified T7 RNA polymerases and purified. In one example, the 5'-fixed:random:3'-fixed sequence is separated by random sequence having 30 to 50 nucleotides.

The aptamers with specificity and binding affinity to the targets of the present invention are selected by the SELEX process described above. As part of the SELEX process the sequences selected to bind to the target are then optionally minimized to determine the minimal sequence having binding affinity, and optimized by performing random or directed mutagenesis of the minimized sequence to determine if increases of affinity or alternatively which positions in the sequence are essential for binding activity. Additionally, selections can be performed with sequences incorporating modified sequences to stabilize the aptamer molecules against degradation in vivo.

2'Modified SELEX™

In addition, the SELEX™ method can be performed to generate 2'modified aptamers as described in U.S. Ser. No. 60/430,761, filed Dec. 3, 2002, U.S. Provisional Patent Application Ser. No. 60/487,474, filed Jul. 15, 2003, and U.S. Provisional Patent Application Ser. No. 60/517,039, filed Nov. 4, 2003, and U.S. patent application Ser. No. 10/729,581, filed Dec. 3, 2003, each of which is herein incorporated by reference in its entirety.

In order for an aptamer to be suitable for use as a therapeutic, it is preferably inexpensive to synthesize, safe and stable in vivo. Wild-type RNA and DNA aptamers are typically not stable in vivo because of their susceptibility to degradation by nucleases. Resistance to nuclease degradation can be greatly increased by the incorporation of modifying groups at the 2'-position. Fluoro and amino groups have been successfully incorporated into oligonucleotide libraries from which aptamers have been subsequently selected. However, these modifications greatly increase the cost of synthesis of the resultant aptamer, and may introduce safety concerns because of the possibility that the modified nucleotides could be recycled into host DNA, by degradation of the modified oligonucleotides and subsequent use of the nucleotides as substrates for DNA synthesis.

Aptamers that contain 2'-O-methyl (2'-OMe) nucleotides overcome many of these drawbacks. Oligonucleotides containing 2'-O-methyl nucleotides are nuclease-resistant and inexpensive to synthesize. Although 2'-O-methyl nucleotides are ubiquitous in biological systems, natural polymerases do not accept 2'-O-methyl NTPs as substrates under physiological conditions, thus there are no safety concerns over the recycling of 2'-O-methyl nucleotides into host DNA.

The present invention also provides materials and methods to produce stabilized oligonucleotides, including, e.g., aptamers, which contain modified nucleotides (e.g., nucleotides which have a modification at the 2'position) which make the oligonucleotide more stable than the unmodified oligonucleotide. The stabilized oligonucleotides produced by the materials and methods of the present invention are also more stable to enzymatic and chemical degradation as well as thermal and physical degradation. For example, oligonucleotides containing 2'-O-methyl nucleotides are nuclease-resistant and inexpensive to synthesize. Although 2'-O-methyl nucleotides are ubiquitous in biological systems, natural polymerases do not accept 2'-O-methyl NTPs as substrates under physiological conditions, thus there are no safety concerns over the recycling of 2'-O-methyl nucleotides into host DNA.

In one embodiment, the present invention provides combinations of 2'-OH, 2'-F, 2'-deoxy, and 2'-OMe modifications of the ATP, GTP, CTP, TTP, and UTP nucleotides. In another embodiment, the present invention provides combinations of 2'-OH, 2'-F, 2'-deoxy, 2'-OMe, 2'-NH$_2$, and 2'-methoxyethyl modifications of the ATP, GTP, CTP, TTP, and UTP nucleotides. In one embodiment, the present invention provides 56 combinations of 2'-OH, 2'-F, 2'-deoxy, 2'-OMe, 2'-NH$_2$, and 2'-methoxyethyl modifications the ATP, GTP, CTP, TTP, and UTP nucleotides.

2' modified aptamers of the invention are created using modified polymerases, such as, e.g., a modified T7 polymerase, having a higher incorporation rate of modified nucleotides having bulky substituents at the furanose 2' position, than wild-type polymerases. For example, a double T7 polymerase mutant (Y639F/H784A) having the histidine at position 784 changed to an alanine, or other small amino acid, residue, in addition to the Y639F mutation has been described for incorporation of bulky 2' substituents and has been used to incorporate modified pyrimidine NTPs. A single mutant T7 polymerase (H784A) having the histidine at position 784 changed to an alanine residue has also been described. (Padilla et al., Nucleic Acids Research, 2002, 30: 138). In both the Y639F/H784A double mutant and H784A single mutant T7 polymerases, the change to smaller amino acid residues allows for the incorporation of bulkier nucleotide substrates, e.g., 2'-O methyl substituted nucleotides.

Another important factor in the production of 2'-modified aptamers is the use of both divalent magnesium and manganese in the transcription mixture. Different combinations of concentrations of magnesium chloride and manganese chloride have been found to affect yields of 2'-O-methylated transcripts, the optimum concentration of the magnesium and manganese chloride being dependent on the concentration in the transcription reaction mixture of NTPs which complex divalent metal ions.

Priming transcription with GMP or guanosine is also important. This effect results from the specificity of the polymerase for the initiating nucleotide. As a result, the 5'-terminal nucleotide of any transcript generated in this fashion is likely to be 2'-OH G. The preferred concentration of GMP (or guanosine) is 0.5 mM and even more preferably 1 mM. It has also been found that including PEG, preferably PEG-8000, in the transcription reaction is useful to maximize incorporation of modified nucleotides.

There are several examples of 2'-OMe containing aptamers in the literature, see, for example Green et al., Current Biology 2, 683-695, 1995. These were generated by the in vitro selection of libraries of modified transcripts in which the C and U residues were 2'-fluoro (2'-F) substituted and the A and G residues were 2'-OH. Once functional sequences were identified then each A and G residue was tested for tolerance to 2'-OMe substitution, and the aptamer was re-synthesized having all A and G residues which tolerated 2'-OMe substitution as 2'-OMe residues. Most of the A and G residues of aptamers generated in this two-step fashion tolerate substitution with 2'-OMe residues, although, on average, approximately 20% do not. Consequently, aptamers generated using this method tend to contain from two to four 2'-OH residues, and stability and cost of synthesis are compromised as a result. By incorporating modified nucleotides into the transcription reaction which generate stabilized oligonucleotides used in oligonucleotide libraries from which aptamers are selected and enriched by SELEX™ (and/or any of its variations and improvements, including those described below), the methods of the present invention eliminate the need for stabilizing the selected aptamer oligonucleotides (e.g., by resynthesizing the aptamer oligonucleotides with modified nucleotides).

Furthermore, the modified oligonucleotides of the invention can be further stabilized after the selection process has been completed. (See "post-SELEX™ modifications", including truncating, deleting and modification, below.)

To generate oligonucleotide populations which are resistant to nucleases and hydrolysis, modified oligonucleotides can be used and can include one or more substitute internucleotide linkages, altered sugars, altered bases, or combinations thereof. In one embodiment, oligonucleotides are provided in which the P(O)O group is replaced by P(O)S ("thioate"), P(S)S ("dithioate"), P(O)NR$_2$ ("amidate"), P(O) R, P(O)OR', CO or CH$_2$ ("formacetal") or 3'-amine (—NH—CH$_2$—CH$_2$—), wherein each R or R' is independently H or substituted or unsubstituted alkyl. Linkage groups can be attached to adjacent nucleotide through an —O—, —N—, or —S— linkage. Not all linkages in the oligonucleotide are required to be identical.

Incorporation of modified nucleotides into the aptamers of the invention is accomplished before (pre-) the selection process (e.g., a pre-SELEX™ process modification). Optionally, aptamers of the invention in which modified nucleotides have been incorporated by pre-SELEX™ process modification can be further modified by post-SELEX™ process modification (i.e., a post-SELEX™ process modification after a pre-SELEX™ modification). Pre-SELEX™ process modifications yield modified nucleic acid ligands with specificity for the SELEX™ target and also improved in vivo stability. Post-SELEX™ process modifications (e.g., modification of previously identified ligands having nucleotides incorporated by pre-SELEX™ process modification) can result in a further improvement of in vivo stability without adversely affecting the binding capacity of the nucleic acid ligand having nucleotides incorporated by pre-SELEX™ process modification.

Modified Polymerases

A single mutant T7 polymerase (Y639F) in which the tyrosine residue at position 639 has been changed to phenylalanine readily utilizes 2'deoxy, 2'amino-, and 2'fluoronucleotide triphosphates (NTPs) as substrates and has been widely used to synthesize modified RNAs for a variety of applications. However, this mutant T7 polymerase reportedly can not readily utilize (e.g., incorporate) NTPs with bulkier 2'-substituents, such as 2'-O-methyl (2'-OMe) or 2'-azido (2'-N$_3$) substituents. For incorporation of bulky 2' substituents, a double T7 polymerase mutant (Y639F/H784A) having the histidine at position 784 changed to an alanine, or other small amino acid, residue, in addition to the Y639F mutation has been described and has been used to incorporate modified pyrimidine NTPs. A single mutant T7 polymerase (H784A) having the histidine at position 784 changed to an alanine residue has also been described. (Padilla et al., Nucleic Acids Research, 2002, 30: 138). In both the Y639F/H784A double mutant and H784A single mutant T7 polymerases, the change to smaller amino acid residues allows for the incorporation of bulkier nucleotide substrates, e.g., 2'-O methyl substituted nucleotides.

The present invention provides methods and conditions for using these and other modified T7 polymerases having a higher incorporation rate of modified nucleotides having bulky substituents at the furanose 2' position, than wild-type polymerases. Generally, it has been found that under the conditions disclosed herein, the Y693F single mutant can be used for the incorporation of all 2'-OMe substituted NTPs except GTP and the Y639F/H784A double mutant can be used for the incorporation of all 2'-OMe substituted NTPs including GTP. It is expected that the H784A single mutant possesses similar properties when used under the conditions disclosed herein.

The present invention provides methods and conditions for modified T7 polymerases to enzymatically incorporate modified nucleotides into oligonucleotides. Such oligonucleotides may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this way, transcripts, or libraries of transcripts are generated using any combination of modifications, for example, ribonucleotides, (2'-OH, "rN"), deoxyribonucleotides (2'-deoxy), 2'-F, and 2'-OMe nucleotides. A mixture containing 2'-OMe C and U and 2'-OH A and G is called "rRmY"; a mixture containing deoxy A and G and 2'-OMe U and C is called "dRmY"; a mixture containing 2'-OMe A, C, and U, and 2'-OH G is called "rGmH"; a mixture alternately containing 2'-OMe A, C, U and G and 2'-OMe A, U and C and 2'-F G is called "toggle"; a mixture containing 2'-OMe A, U, C, and G, where up to 10% of the G's are deoxy is called "r/mGmH"; a mixture containing 2'-O Me A, U, and C, and 2'-F G is called "fGmH"; and a mixture containing deoxy A, and 2'-OMe C, G and U is called "dAmB".

A preferred embodiment includes any combination of 2'-OH, 2'-deoxy and 2'-OMe nucleotides. A more preferred embodiment includes any combination of 2'-deoxy and 2'-OMe nucleotides. An even more preferred embodiment is with any combination of 2'-deoxy and 2'-OMe nucleotides in which the pyrimidines are 2'-OMe (such as dRmY, mN or dGmH).

2'-O-Methyl Modified Nucleotide SELEX™

The present invention provides methods to generate libraries of 2'-modified (e.g., 2'-OMe) RNA transcripts in conditions under which a polymerase accepts 2'-modified NTPs. Preferably, the polymerase is the Y693F/H784A double mutant or the Y693F single mutant. Other polymerases, particularly those that exhibit a high tolerance for bulky 2'-substituents, may also be used in the present invention. Such polymerases can be screened for this capability by assaying their ability to incorporate modified nucleotides under the transcription conditions disclosed herein. A number of factors have been determined to be crucial for the transcription conditions useful in the methods disclosed herein. For example, great increases in the yields of modified transcript are observed when a leader sequence is incorporated into the 5' end of a fixed sequence at the 5' end of the DNA transcription template, such that at least about the first 6 residues of the resultant transcript are all purines.

Another important factor in obtaining transcripts incorporating modified nucleotides is the presence or concentration of 2'-OH GTP. Transcription can be divided into two phases: the first phase is initiation, during which an NTP is added to the 3'-hydroxyl end of GTP (or another substituted guanosine) to yield a dinucleotide which is then extended by about 10-12 nucleotides, the second phase is elongation, during which transcription proceeds beyond the addition of the first about 10-12 nucleotides. It has been found that small amounts of 2'-OH GTP added to a transcription mixture containing an excess of 2'-OMe GTP are sufficient to enable the polymerase to initiate transcription using 2'-OH GTP, but once transcription enters the elongation phase the reduced discrimination between 2'-OMe and 2'-OH GTP, and the excess of 2'-OMe GTP over 2'-OH GTP allows the incorporation of principally the 2'-OMe GTP.

Another important factor in the incorporation of 2'-OMe into transcripts is the use of both divalent magnesium and manganese in the transcription mixture. Different combinations of concentrations of magnesium chloride and manganese chloride have been found to affect yields of 2'-O-methylated transcripts, the optimum concentration of the magnesium and manganese chloride being dependent on the concentration in the transcription reaction mixture of NTPs which complex divalent metal ions. To obtain the greatest yields of maximally 2' substituted O-methylated transcripts (i.e., all A, C, and U and about 90% of G nucleotides), concentrations of approximately 5 mM magnesium chloride and 1.5 mM manganese chloride are preferred when each NTP is present at a concentration of 0.5 mM. When the concentration of each NTP is 1.0 mM, concentrations of approximately 6.5 mM magnesium chloride and 2.0 mM manganese chloride are preferred. When the concentration of each NTP is 2.0 mM, concentrations of approximately 9.6 mM magnesium chloride and 2.9 mM manganese chloride are preferred. In any case, departures from these concentrations of up to two-fold still give significant amounts of modified transcripts.

Priming transcription with GMP or guanosine is also important. This effect results from the specificity of the polymerase for the initiating nucleotide. As a result, the 5'-terminal nucleotide of any transcript generated in this fashion is likely to be 2'-OH G. The preferred concentration of GMP (or guanosine) is 0.5 mM and even more preferably 1 mM. It has also been found that including PEG, preferably PEG-8000, in the transcription reaction is useful to maximize incorporation of modified nucleotides.

For maximum incorporation of 2'-OMe ATP (100%), UTP (100%), CTP (100%) and GTP (~90%) ("r/mGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (6.5 mM where the concentration of each 2'-OMe NTP is 1.0 mM), MnCl$_2$ 1.5 mM (2.0 mM where the concentration of each 2'-OMe NTP is 1.0 mM), 2'-OMe NTP (each) 500 µM (more preferably, 1.0 mM), 2'-OH GTP 30 µM, 2'-OH GMP 500 µM, pH 7.5, Y639F/H784A T7 RNA Polymerase 15 units/ml, inorganic pyrophosphatase 5 units/ml, and an all-purine leader sequence of at least 8 nucleotides long. As used herein, one unit of the Y639F/H784A mutant T7 RNA polymerase, or any other mutant T7 RNA polymerase specified herein) is defined as the amount of enzyme required to incorporate 1 nmole of 2'-OMe NTPs into transcripts under the r/mGmH conditions. As used herein, one unit of inorganic pyrophosphatase is defined as the amount of enzyme that will liberate 1.0 mole of inorganic orthophosphate per minute at pH 7.2 and 25° C.

For maximum incorporation (100%) of 2'-OMe ATP, UTP and CTP ("rGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (9.6 mM where the concentration of each 2'-OMe NTP is 2.0 mM), MnCl$_2$ 1.5 mM (2.9 mM where the concentration of each 2'-OMe NTP is 2.0 mM), 2'-OMe NTP (each) 500 µM (more preferably, 2.0 mM), pH 7.5, Y639F T7 RNA Polymerase 15 units/ml, inorganic pyrophosphatase 5 units/ml, and an all-purine leader sequence of at least 8 nucleotides long.

For maximum incorporation (100%) of 2'-OMe UTP and CTP ("rRmY") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (9.6 mM where the concentration of each 2'-OMe NTP is 2.0 mM), MnCl$_2$ 1.5 mM (2.9 mM where the concentration of each 2'-OMe NTP is 2.0 mM), 2'-OMe NTP (each) 500 µM (more preferably, 2.0 mM), pH 7.5, Y639F/H784A T7 RNA Polymerase 15 units/ml, inorganic pyrophosphatase 5 units/ml, and an all-purine leader sequence of at least 8 nucleotides long.

For maximum incorporation (100%) of deoxy ATP and GTP and 2'-OMe UTP and CTP ("dRmY") into transcripts the following conditions are preferred: HEPES buffer 200 mM, DTT 40 mM, spermine or spermidine 2 mM, PEG-8000 10% (w/v), Triton X-100 0.01% (w/v), MgCl$_2$ 9.6 mM, MnCl$_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For maximum incorporation (100%) of 2'-OMe ATP, UTP and CTP and 2'-F GTP ("fGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 9.6 mM, MnCl$_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For maximum incorporation (100%) of deoxy ATP and 2'-OMe UTP, GTP and CTP ("dAmB") into transcripts the following conditions are preferred: HEPES buffer 200 mM, DTT 40 mM, spermidine 2 mM, PEG-8000 10% (w/v), Triton X-100 0.01% (w/v), MgCl$_2$ 9.6 mM, MnCl$_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For each of the above, (1) transcription is preferably performed at a temperature of from about 30° C. to about 45° C. and for a period of at least two hours and (2) 50-300 nM of a double stranded DNA transcription template is used (200 nm template was used for round 1 to increase diversity (300 nm template was used for dRmY transcriptions), and for subsequent rounds approximately 50 nM, a 1/10 dilution of an optimized PCR reaction, using conditions described herein, was used). The preferred DNA transcription templates are described below (where ARC254 and ARC256 transcribe under all 2'-OMe conditions and ARC255 transcribes under rRmY conditions).

ARC254:
5'-CATCGATGCTAGTCGTAACGATCNNNNNNNNNNNNNNNNNNNNNNNNN
NNNNNCGAGAACGTTCTCTCCTCTCCCTATAGTGAGTCGTATTA-3'  (SEQ ID NO: 51)

ARC255:
5'-CATGCATCGCGACTGACTAGCCGNNNNNNNNNNNNNNNNNNNNNNNNN
NNNNNGTAGAACGTTCTCTCCTCTCCCTATAGTGAGTCGTATTA-3'  (SEQ ID NO: 52)

ARC256:
5'-CATCGATCGATCGATCGACAGCGNNNNNNNNNNNNNNNNNNNNNNNNN
NNNNNGTAGAACGTTCTCTCCTCTCCCTATAGTGAGTCGTATTA-3'  (SEQ ID NO: 53)

Under rN transcription conditions of the present invention, the transcription reaction mixture comprises 2'-OH adenosine triphosphates (ATP), 2'-OH guanosine triphosphates (GTP), 2'-OH cytidine triphosphates (CTP), and 2'-OH uridine triphosphates (UTP). The modified oligonucleotides produced using the rN transcription mixtures of the present invention comprise substantially all 2'-OH adenosine, 2'-OH guanosine, 2'-OH cytidine, and 2'-OH uridine. In a preferred embodiment of rN transcription, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-OH cytidine, and at least 80% of all uridine nucleotides are 2'-OH uridine. In a more preferred embodiment of rN transcription, the resulting modified oligonucleotides of the present invention comprise a sequence where at least 90% of all adenosine nucleotides are 2'-OH adenosine, at least 90% of all guanosine nucleotides are 2'-OH guanosine, at least 90% of all cytidine nucleotides are 2'-OH cytidine, and at least 90% of all uridine nucleotides are 2'-OH uridine. In a most preferred embodiment of rN transcription, the modified oligonucleotides of the present invention comprise 100% of all adenosine nucleotides are 2'-OH adenosine, of all guanosine nucleotides are 2'-OH guanosine, of all cytidine nucleotides are 2'-OH cytidine, and of all uridine nucleotides are 2'-OH uridine.

Under rRmY transcription conditions of the present invention, the transcription reaction mixture comprises 2'-OH adenosine triphosphates, 2'-OH guanosine triphosphates, 2'-O-methyl cytidine triphosphates, and 2'-O-methyl uridine triphosphates. The modified oligonucleotides produced using the rRmY transcription mixtures of the present invention comprise substantially all 2'-OH adenosine, 2'-OH guanosine, 2'-O-methyl cytidine and 2'-O-methyl uridine. In a preferred embodiment, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-O-methyl cytidine and at least 80% of all uridine nucleotides are 2'-O-methyl uridine. In a more preferred embodiment, the resulting modified oligonucleotides comprise a sequence where at least 90% of all adenosine nucleotides are 2'-OH adenosine, at least 90% of all guanosine nucleotides are 2'-OH guanosine, at least 90% of all cytidine nucleotides are 2'-O-methyl cytidine and at least 90% of all uridine nucleotides are 2'-O-methyl uridine In a most preferred embodiment, the resulting modified oligonucleotides comprise a sequence where 100% of all adenosine nucleotides are 2'-OH adenosine, 100% of all guanosine nucleotides are 2'-OH guanosine, 100% of all cytidine nucleotides are 2'-O-methyl cytidine and 100% of all uridine nucleotides are 2'-O-methyl uridine.

Under dRmY transcription conditions of the present invention, the transcription reaction mixture comprises 2'-deoxy purine triphosphates and 2'-O-methyl pyrimidine triphosphates. The modified oligonucleotides produced using the dRmY transcription conditions of the present invention comprise substantially all 2'-deoxy purines and 2'-O-methyl pyrimidines. In a preferred embodiment, the resulting modified oligonucleotides of the present invention comprise a sequence where at least 80% of all purine nucleotides are 2'-deoxy purines and at least 80% of all pyrimidine nucleotides are 2'-O-methyl pyrimidines. In a more preferred embodiment, the resulting modified oligonucleotides of the present invention comprise a sequence where at least 90% of all purine nucleotides are 2'-deoxy purines and at least 90% of all pyrimidine nucleotides are 2'-O-methyl pyrimidines. In a most preferred embodiment, the resulting modified oligonucleotides of the present invention comprise a sequence where 100% of all purine nucleotides are 2'-deoxy purines and 100% of all pyrimidine nucleotides are 2'-O-methyl pyrimidines.

Under rGmH transcription conditions of the present invention, the transcription reaction mixture comprises 2'-OH guanosine triphosphates, 2'-O-methyl cytidine triphosphates, 2'-O-methyl uridine triphosphates, and 2'-O-methyl adenosine triphosphates. The modified oligonucleotides produced using the rGmH transcription mixtures of the present invention comprise substantially all 2'-OH guanosine, 2'-O-methyl cytidine, 2'-O-methyl uridine, and 2'-O-methyl adenosine. In a preferred embodiment, the resulting modified oligonucleotides comprise a sequence where at least 80% of all guanosine nucleotides are 2'-OH guanosine, at least 80% of all cytidine nucleotides are 2'-O-methyl cytidine, at least 80% of all uridine nucleotides are 2'-O-methyl uridine, and at least 80% of all adenosine nucleotides are 2'-O-methyl adenosine. In a more preferred embodiment, the resulting modified oligonucleotides comprise a sequence where at least 90% of all guanosine nucleotides are 2'-OH guanosine, at least 90% of all cytidine nucleotides are 2'-O-methyl cytidine, at least 90% of all uridine nucleotides are 2'-O-methyl uridine, and at least 90% of all adenosine nucleotides are 2'-O-methyl adenosine. In a most preferred embodiment, the resulting modified oligonucleotides comprise a sequence where 100% of all guanosine nucleotides are 2'-OH guanosine, 100% of all cytidine nucleotides are 2'-O-methyl cytidine, 100% of all uridine nucleotides are 2'-O-methyl uridine, and 100% of all adenosine nucleotides are 2'-O-methyl adenosine.

Under r/mGmH transcription conditions of the present invention, the transcription reaction mixture comprises 2'-O-methyl adenosine triphosphate, 2'-O-methyl cytidine triphosphate, 2'-O-methyl guanosine triphosphate, 2'-O-methyl uridine triphosphate and deoxy guanosine triphosphate. The resulting modified oligonucleotides produced using the r/mGmH transcription mixtures of the present invention comprise substantially all 2'-O-methyl adenosine, 2'-O-methyl cytidine, 2'-O-methyl guanosine, and 2'-O-methyl uridine, wherein the population of guanosine nucleotides has a maximum of about 10% deoxy guanosine. In a preferred embodiment, the resulting r/mGmH modified oligonucleotides of the present invention comprise a sequence where at least 80% of all adenosine nucleotides are 2'-O-methyl adenosine, at least 80% of all cytidine nucleotides are 2'-O-methyl cytidine, at least 80% of all guanosine nucleotides are 2'-O-methyl guanosine, at least 80% of all uridine nucleotides are 2'-O-methyl uridine, and no more than about 10% of all guanosine nucleotides are deoxy guanosine. In a more preferred embodiment, the resulting modified oligonucleotides comprise a sequence where at least 90% of all adenosine nucleotides are 2'-O-methyl adenosine, at least 90% of all cytidine nucleotides are 2'-O-methyl cytidine, at least 90% of all guanosine nucleotides are 2'-O-methyl guanosine, at least 90% of all uridine nucleotides are 2'-O-methyl uridine, and no more than about 10% of all guanosine nucleotides are deoxy guanosine. In a most preferred embodiment, the resulting modified oligonucleotides comprise a sequence where 100% of all adenosine nucleotides are 2'-O-methyl adenosine, 100% of all cytidine nucleotides are 2'-O-methyl cytidine, 90% of all guanosine nucleotides are 2'-O-methyl guanosine, and 100% of all uridine nucleotides are 2'-O-methyl uridine, and no more than about 10% of all guanosine nucleotides are deoxy guanosine.

Under fGmH transcription conditions of the present invention, the transcription reaction mixture comprises 2'-O-methyl adenosine triphosphates (ATP), 2'-O-methyl uridine triphosphates (UTP), 2'-O-methyl cytidine triphosphates (CTP), and 2'-F guanosine triphosphates. The modified oligonucleotides produced using the fGmH transcription conditions of the present invention comprise substantially all 2'-O-methyl adenosine, 2'-O-methyl uridine, 2'-O-methyl cytidine, and 2'-F guanosine. In a preferred embodiment, the resulting modified oligonucleotides comprise a sequence where at least 80% of all adenosine nucleotides are 2'-O-methyl adenosine, at least 80% of all uridine nucleotides are 2'-O-methyl uridine, at least 80% of all cytidine nucleotides are 2'-O-methyl cytidine, and at least 80% of all guanosine nucleotides are 2'-F guanosine. In a more preferred embodiment, the resulting modified oligonucleotides comprise a sequence where at least 90% of all adenosine nucleotides are 2'-O-methyl adenosine, at least 90% of all uridine nucleotides are 2'-O-methyl uridine, at least 90% of all cytidine nucleotides are 2'-O-methyl cytidine, and at least 90% of all guanosine nucleotides are 2'-F guanosine. The resulting modified oligonucleotides comprise a sequence where 100% of all adenosine nucleotides are 2'-O-methyl adenosine, 100% of all uridine nucleotides are 2'-O-methyl uridine, 100% of all cytidine nucleotides are 2'-O-methyl cytidine, and 100% of all guanosine nucleotides are 2'-F guanosine.

Under dAmB transcription conditions of the present invention, the transcription reaction mixture comprises 2'-deoxy adenosine triphosphates (dATP), 2'-O-methyl cytidine triphosphates (CTP), 2'-O-methyl guanosine triphosphates (GTP), and 2'-O-methyl uridine triphosphates (UTP). The modified oligonucleotides produced using the dAmB transcription mixtures of the present invention comprise substantially all 2'-deoxy adenosine, 2'-O-methyl cytidine, 2'-O-methyl guanosine, and 2'-O-methyl uridine. In a preferred embodiment, the resulting modified oligonucleotides comprise a sequence where at least 80% of all adenosine nucleotides are 2'-deoxy adenosine, at least 80% of all cytidine nucleotides are 2'-O-methyl cytidine, at least 80% of all guanosine nucleotides are 2'-O-methyl guanosine, and at least 80% of all uridine nucleotides are 2'-O-methyl uridine. In a more preferred embodiment, the resulting modified oligonucleotides comprise a sequence where at least 90% of all adenosine nucleotides are 2'-deoxy adenosine, at least 90% of all cytidine nucleotides are 2'-O-methyl cytidine, at least 90% of all guanosine nucleotides are 2'-O-methyl guanosine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all cytidine nucleotides are 2'-O-methyl cytidine, 100% of all guanosine nucleotides are 2'-O-methyl guanosine, and 100% of all uridine nucleotides are 2'-O-methyl uridine.

In each case, the transcription products can then be used as the library in the SELEX™ process to identify aptamers and/or to determine a conserved motif of sequences that have binding specificity to a given target. The resulting sequences are already stabilized, eliminating this step from the process to arrive at a stabilized aptamer sequence and giving a more highly stabilized aptamer as a result. Another advantage of the 2'-OMe SELEX™ process is that the resulting sequences are likely to have fewer 2'-OH nucleotides required in the sequence, possibly none.

As described below, lower but still useful yields of transcripts fully incorporating 2'-OMe substituted nucleotides can be obtained under conditions other than the optimized conditions described above. For example, variations to the above transcription conditions include:

The HEPES buffer concentration can range from 0 to 1 M. The present invention also contemplates the use of other buffering agents having a pKa between 5 and 10, for example without limitation, Tris(hydroxymethyl)aminomethane.

The DTT concentration can range from 0 to 400 mM. The methods of the present invention also provide for the use of other reducing agents, for example without limitation, mercaptoethanol.

The spermidine and/or spermine concentration can range from 0 to 20 mM.

The PEG-8000 concentration can range from 0 to 50% (w/v). The methods of the present invention also provide for the use of other hydrophilic polymer, for example without limitation, other molecular weight PEG or other polyalkylene glycols.

The Triton X-100 concentration can range from 0 to 0.1% (w/v). The methods of the present invention also provide for the use of other non-ionic detergents, for example without limitation, other detergents, including other Triton-X detergents.

The $MgCl_2$ concentration can range from 0.5 mM to 50 mM. The $MnCl_2$ concentration can range from 0.15 mM to 15 mM. Both $MgCl_2$ and $MnCl_2$ must be present within the ranges described and in a preferred embodiment are present in about a 10 to about 3 ratio of $MgCl_2$:$MnCl_2$, preferably, the ratio is about 3-5, more preferably, the ratio is about 3 to about 4.

The 2'-OMe NTP concentration (each NTP) can range from 5 µM to 5 mM.

The 2'-OH GTP concentration can range from 0 µM to 300 µM.

The 2'-OH GMP concentration can range from 0 to 5 mM.

The pH can range from pH 6 to pH 9. The methods of the present invention can be practiced within the pH range of activity of most polymerases that incorporate modified nucleotides. In addition, the methods of the present invention provide for the optional use of chelating agents in the transcription reaction condition, for example without limitation, EDTA, EGTA, and DTT.

The selected aptamers having the highest affinity and specific binding as demonstrated by biological assays as described in the examples below are suitable therapeutics for treating conditions in which the target is involved in pathogenesis.

Aptamer Therapeutics

Aptamers represent a promising class of therapeutic agents currently in pre-clinical and clinical development. Like biologics, e.g., peptides or monoclonal antibodies, aptamers are capable of binding specifically to molecular targets and, through binding, inhibiting target function. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), Gene 137(1): 25-31; Jenison, et al. (1998), Antisense Nucleic Acid Drug Dev. 8(4): 265-79; Bell, et al. (1999), In Vitro Cell. Dev. Biol. Anim. 35(9): 533-42; Watson, et al. (2000), Antisense Nucleic Acid Drug Dev. 10(2): 63-75; Daniels, et al. (2002), Anal. Biochem. 305(2): 214-26; Chen, et al. (2003), Proc. Natl. Acad. Sci. U.S.A. 100(16): 9226-31; Khati, et al. (2003), J. Virol. 77(23): 12692-8; Vaish, et al. (2003), Biochemistry 42(29): 8842-51). Created by an entirely in vitro selection process (SELEX™) from libraries of random sequence oligonucleotides, aptamers have been generated against numerous proteins of therapeutic interest, including growth factors, enzymes, immunoglobulins, and receptors (Ellington and Szostak (1990), Nature 346(6287): 818-22; Tuerk and Gold (1990), Science 249(4968): 505-510).

Aptamers have a number of attractive characteristics for use as therapeutics. In addition to high target affinity and specificity, aptamers have shown little or no toxicity or immunogenicity in standard assays (Wlotzka, et al. (2002), Proc. Natl. Acad. Sci. U.S.A. 99(13): 8898-902). Several therapeutic aptamers have been optimized and advanced through varying stages of pre-clinical development, including pharmacokinetic analysis, characterization of biological efficacy in cellular and animal disease models, and preliminary safety pharmacology assessment (Reyderman and Stavchansky (1998), Pharmaceutical Research 15(6): 904-10; Tucker et al., (1999), J. Chromatography B. 732: 203-212; Watson, et al. (2000), Antisense Nucleic Acid Drug Dev. 10(2): 63-75).

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), such aptamers must be able to be distributed to target organs and tissues, and remain in the body (unmodified) for a period of time consistent with the desired dosing regimen. Early work on nucleic acid-based therapeutics has shown that, while unmodified oligonucleotides are degraded rapidly by nuclease digestion, protective modifications at the 2'-position of the sugar, and use of inverted terminal cap structures, e.g., [3'-3'dT], dramatically improve nucleic acid stability in vitro and in vivo (Green, et al. (1995), Chem. Biol. 2(10): 683-95; Jellinek, et al. (1995), Biochemistry 34(36): 11363-72; Ruckman, et al. (1998), J. Biol. Chem. 273(32): 20556-67; Uhlmann, et al. (2000), Methods Enzymol. 313: 268-84). In some SELEX selections (i.e., SELEX experiments or SELEXions), starting pools of nucleic acids from which aptamers are selected are typically pre-stabilized by chemical modification, for example by incorporation of 2'-fluoropyrimidine (2'-F) substituted nucleotides, to enhance resistance of aptamers against nuclease attack. Aptamers incorporating 2'-O-methylpurine (2'-OMe purine) substituted nucleotides have also been developed through post-SELEX modification steps or, more recently, by enabling synthesis of 2'-OMe-containing random sequence libraries as an integral component of the SELEX process itself, as described above.

In addition to clearance by nucleases, oligonucleotide therapeutics are subject to elimination via renal filtration. As such, a nuclease-resistant oligonucleotide administered intravenously exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation of small therapeutics to a PEG polymer (PEGylation), described below, can dramatically lengthen residence times of aptamers in circulation, thereby decreasing dosing frequency and enhancing effectiveness against vascular targets. Previous work in animals has examined the plasma pharmacokinetic properties of PEG-conjugated aptamers (Reyderman and Stavchansky (1998), Pharmaceutical Research 15(6): 904-10; Watson, et al. (2000), Antisense Nucleic Acid Drug Dev. 10(2): 63-75). Determining the extravasation of an aptamer therapeutic, including aptamer therapeutics conjugated to a modifying moiety or containing modified nucleotides, and in particular, determining the potential of aptamers or their modified forms to access diseased tissues (for example, sites of inflammation, or the interior of tumors) will better define the spectrum of therapeutic opportunities for aptamer intervention.

The pharmacokinetic profiles of aptamer compositions of the invention have "tunability" (i.e., the ability to modulate aptamer pharmacokinetics). The tunability of aptamer pharmacokinetics is achieved, for example through conjugation of modifying moieties (e.g., PEG polymers) to the aptamer and/or the incorporation of modified nucleotides (e.g., 2'-fluoro and/or 2'-OMe substitutions) to alter the chemical composition of the nucleic acid.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described in provisional application U.S. Ser. No. 60/550,790, filed on Mar. 5, 2004 and entitled "Controlled Modulation of the Pharmacokinetics and Biodistribution of Aptamer Therapeutics", PEGylation of an aptamer therapeutic (e.g. PEGylation with a 20 kDa PEG polymer) is used to target inflamed tissues, such that the PEGylated aptamer therapeutic preferentially accumulates in inflamed tissue.

The pharmacokinetic and biodistribution profiles of aptamer therapeutics are determined by monitoring a variety of parameters. Such parameters include, for example, the half-life ($t_{1/2}$), the plasma clearance (Cl), the volume of distribution (Vss), the area under the concentration-time curve (AUC), maximum observed serum or plasma concentration ($C_{max}$), and the mean residence time (MRT) of an aptamer composition. As used herein, the term "AUC" refers to the area under the plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (Cl) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

PDGF and PDGF-VEGF Specific Binding Aptamers as Oncology Therapeutics

Aptamers specifically capable of binding and inhibiting different PDGF isoforms are set forth herein. These aptamers, which include aptamers that bind only to PDGF, aptamers that bind to both PDGF and VEGF, and either of the above aptamers having a CpG motif incorporated therein, provide a low-toxicity, safe, and effective modality of inhibiting most PDGF-mediated tumor progression, including without limitation, glioblastomas, chronic myelomonocytic leukemia (CMML), dermatofibrosarcoma protuberans (DFSP), gastrointestinal stromal tumors, (GIST), and other soft tissue sarcomas.

Examples of PDGF and PDGF-VEGF specific binding aptamers for use as oncology therapeutics include the following sequences:

PDGF-Binding Aptamers:

ARC126:
5'-(5'-NH2-dC-dA-dG-dG-dC-fU-dA-fC-mG- 3',
SEQ ID No. 1)-

HEG-(5'-dC-dG-T-dA-mG-dA-mG-dC-dA-fU-fC-mA-3',
SEQ ID No. 2)-

HEG-(5'-T-dG-dA-T-fC-fC-fU-mG-3'dT-3',
SEQ ID No. 3)-3' wherein HEG=hexaethylene glycol amidite.

ARC127:
5'-[40K PEG]-(5'-NH2-dC-dA-dG-dG-dC-fU-dA-fC-mG-3',
SEQ ID No. 1)-

HEG-(5'-dC-dG-T-dA-mG-dA-mG-dC-dA-fU-fC-mA-3',
SEQ ID No. 2)-

HEG-(5'-T-dG-dA-T-fC-fC-fU-mG-3'dT-3',
SEQ ID No. 3)-3' wherein HEG=hexaethylene glycol amidite.

ARC240:
5'-[20K PEG]-(5'-NH2-dC-dA-dG-dG-dC-fU-dA-fC-mG-3',
SEQ ID No. 1)-

HEG-(5'-dC-dG-T-dA-mG-dA-mG-dC-dA-fU-fC-mA-3',
SEQ ID No. 2)-

HEG-(5'-T-dG-dA-T-fC-fC-fU-mG-3'dT-3',
SEQ ID No. 3)-3' wherein HEG=hexaethylene glycol amidite.

ARC308:
5'-[30K PEG]-(5'-NH2-dC-dA-dG-dG-dC-fU-dA-fC-mG-3',
SEQ ID No. 1)-

HEG-(5'-dC-dG-T-dA-mG-dA-mG-dC-dA-fU-fC-mA-3',
SEQ ID No. 2)-

HEG-(5'-T-dG-dA-T-fC-fC-fU-mG-3'dT-3',
SEQ ID No. 3)-3' wherein HEG=hexaethylene glycol amidite.

deoxyARC126:
5'-dCdAdGdGdCdTdAdCdGdCdGdTdAdGdAdGdCdAdTdCdAdTdGdAdTdCdCdTdG-[3T]-3'
(SEQ ID NO: 8)

wherein "d" indicates unmodified deoxynucleotides and "[3T]" is as defined above.

ARC124:
5' CACAGGCTACGGCACGTAGAGCATCACCATGATCCTGTG3'InvdT
(SEQ ID NO.: 11)

Scrambled Control Aptamer:

ARC128: (Scrambled ARC126):
5'-(5'-NH2-dC-dA-dG-fC-mG-fU-dA-fC-mG-3',
SEQ ID No. 4)-

HEG-(5'-dC-dG-T-dA-dC-dC-mG-dA-T-fU-fC-mA-3',
SEQ ID No. 5)-

HEG-(5'-T-dG-dA-dA-dG-fC-fU-mG-3'dT-3',
SEQ ID No. 6)-3' wherein HEG=hexaethylene glycol amidite.

VEGF-Binding Aptamer:

ARC245:
5'-mAmUmGmCmAmGmUmUmUmGmAmGmAmAmGmUmCmGmCmGmCmAmU-[3T]-3', (SEQ ID NO: 7)

wherein "m" indicates 2'-OMe nucleotides and "[3T]" refers to an inverted thymidine nucleotide that is attached to the 3'end of the oligonucleotide at the 3' position on the ribose sugar, thus the oligonucleotide has two 5'ends and is thus resistant to nucleases acting on the 3' hydroxyl end.

PDGF/VEGF Binding Multivalent Aptamers:

TK.131.012.A: (SEQ ID NO: 9)
5'dCdAdGdGdCdTdAdCdGmAmUmGmCmAmGmUmUmGmAmGmAmAmGmUmCmG
mCmGmCmAmUdCdGdTdAdGdAdGdCdAdTdCdAdGdAdAdAdTdGdAdTdCdCdCdTdG[3T]-3', wherein "m" indicates 2'-OMe nucleotides, "d" and "[3T]" are as defined above.

TK.131.012.B: (SEQ ID NO: 10)
5'dCdAdGdGdCdTdAdCdGmUmGmCmAmGmUmUmGmAmGmAmAmGmUmCmGmC mGmCmAdCdGdTdAdGdAdGdCdAdTdCdAdGdAdAdAdTdGdAdTdCdCdTdG-[3T]

wherein "m" and "[3T]" are as defined above.

Other aptamers that bind PDGF and/or VEGF are described below, e.g., in Table 2 and in Example 12.

It has been demonstrated that inhibition of PDGF signaling with small molecule receptor antagonists decreases interstitial fluid pressure and increases the uptake of chemotherapeutics into solid tumors. Pietras et al. validated the hypothesis that PDGF-B is involved in IFP and that blocking PDGF-B function could lead to increased uptake of chemotherapeutics into tumors. (Pietras et al., (2003), Cancer Cell vol. 3 p. 439-443). Using the KAT-4 thyroid carcinoma model, which has known PDGF paracrine signaling properties, Pietras et al. demonstrated that KAT-4 tumors expressed PDGF β-receptors in the stroma and that PDGF-B bound KAT-4 cells in vitro. Next, Pietras et al. used the tyrosine kinase inhibiting drug STI571 (GLEEVEC™) to block PDGF-B signaling in KAT-4 tumors and showed that this treatment significantly decreased tumor IFP in vivo leading to increased uptake of taxol. However, since STI571 targets both PDGF α and β receptors, as well as Kit, Abl, and Arg tyrosine kinases, it was impossible to know if the effect of STI571 was due to PDGF-B blockage alone. This ambiguity was solved by using a highly specific aptamer to block PDGF-B in similar experiments. The aptamer has an affinity of 100 pM for PDGF-B and no appreciable affinity for the PDGF-A sequence. As with STI571, treatment of KAT-4 xenograft mice with PEG-conjugated PDGF-B aptamer lowered IFP and dramatically increased tumor uptake of taxol. Most importantly, aptamer treatment strongly enhanced taxol's ability to inhibit tumor growth. In addition, a currently marketed cancer therapeutic, the PDGF-receptor antagonist GLEEVEC™ has been shown to be effective at reducing tumor IFP and increasing the tumor uptake of cytotoxins when used in combination with a cytotoxin such as taxol. Thus, the methods and materials of the present are used to inhibit the biological activity of PDGF-B and its etiology in tumor development and growth by enhancing the uptake and efficacy of chemotherapeutics.

Figure 4:
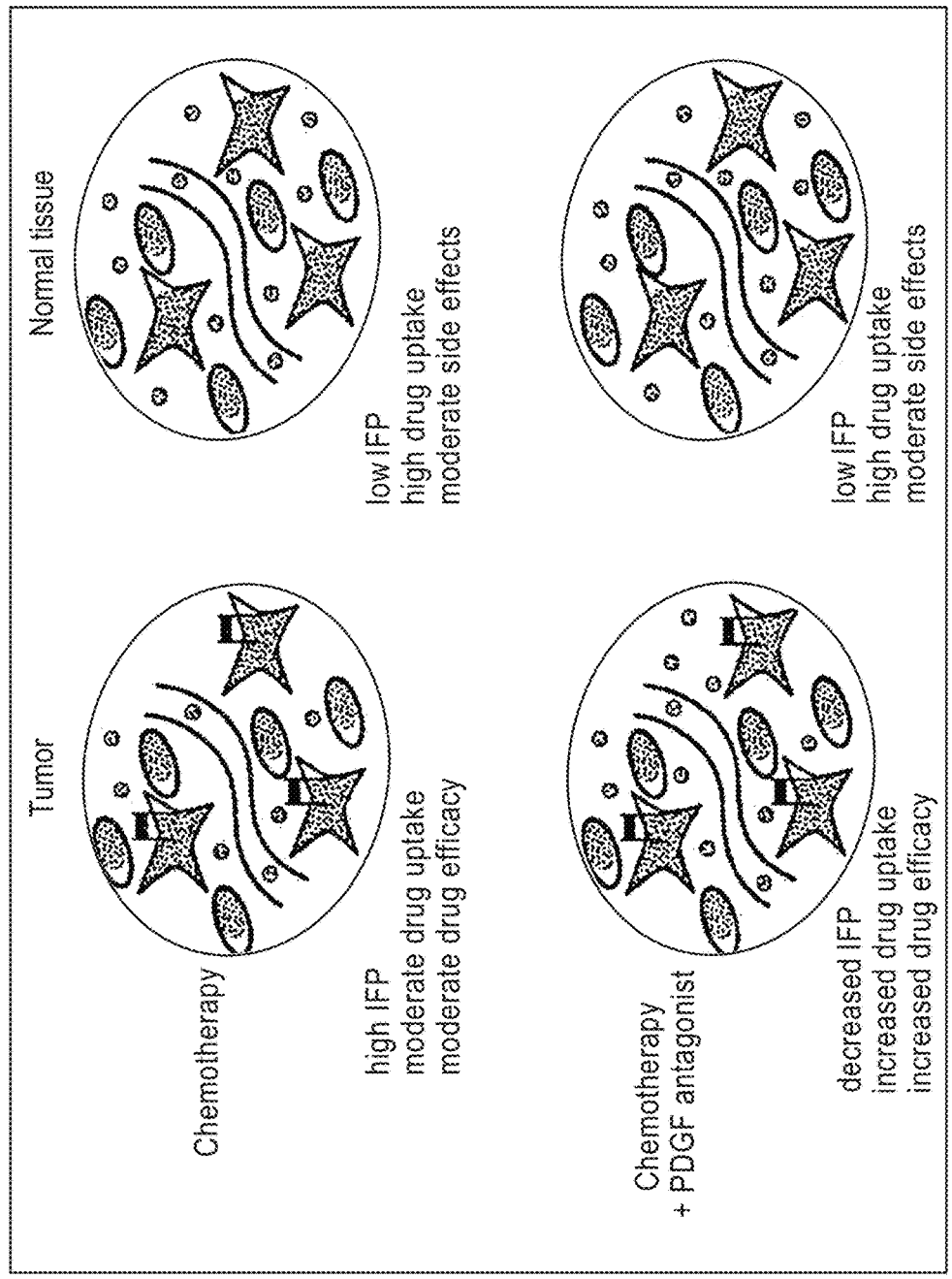
FIG. 4 is a schematic of the transport of cytotoxins across tumor vasculature with and without PDGF antagonists by the methods of the present invention.

In other words, combination therapy methods of the present invention combining PDGF-specific aptamers of the present invention with cytotoxic agents, i.e. combining PDGF-specific aptamers with other known cytotoxins, provides an effective method of delivering drug specifically at the site of tumors, by the selective lowering of IFP in tumor vessels, which in turn allows the increased uptake of cytotoxins in tumors through the tumor vasculature. FIG. 4 shows a schematic of the transport to cytotoxins across tumor vasculature with and without PDGF antagonists by the methods of the present invention (Pietras et al., (2003), Cancer Cell vol. 3 p. 439-443).

The PDGF aptamers of the present invention can be used in combination with a variety of known cytotoxic or cytostatic (collectively, "cytotoxic") agents to lower tumor IFP, and thereby increase delivery and tumor uptake of cytotoxic agents to all solid tumors. Suitable cytotoxic or cytostatic agents include tubulin stabilizers/destabilizers, anti-metabolites, purine synthesis inhibitors, nucleoside analogs, and DNA alkylating or other DNA modifying agents, including but not limited to paclitaxel (TAXOL™), docetaxel, irinotecan, topotecan, gemcitabine, epothilone, cisplatinum, carboplatin, 5-fluoro-U, calicheamycin, doxorubicin, methotrexate, AraC (cytarabine), vinblastin, daunorubicin, oxaliplatinum, cyclophosphamide, iflosamide, pharmarubicin, epirubicin, vinflunine, oblimersen sodium, permetrexed, kinase inhibitors, including but not limited to EGF receptor kinase, VEGF receptor kinase, aurora kinase, either alone or in any combination thereof. The PDGF aptamers of the present invention can be used in combination with a variety of known vascular targeting agents wherein "vascular targeting agent" means a small molecule therapeutic (e.g., irenotecan), a protein therapeutic (e.g., bevicizumab), and/or an oligonucleotide therapeutic (e.g., antisense molecules, siRNA molecules) which modifies the existing vasculature and neovasculature network that supports blood and lymphatic flow to the tumor. The PDGF aptamers of the present invention can be used in combination with a conjugate therapeutic comprising a binding or targeting moiety, and a cytotoxic moiety, wherein the binding or targeting moiety is, but is not limited to, an aptamer, antibody, including, but not limited to trastuzumab, rituximab, cetuximab, panitumumab, gemtuzumab, bevicizumab, and tositumomab, peptide, a vascular targeting agent or folate compound, and wherein the cytotoxic moiety belongs to a class of compounds including but not limited to, tubulin stabilizers/destabilizers, anti-metabolites, purine synthesis inhibitors, nucleoside analogs, and DNA alkylating agents, other DNA modifying agents, or vascular disruptive agents (e.g., flavonoids) alone or in any combination thereof. The materials and methods of the present invention provide a more effective way of administering known chemotherapeutic agents to inhibit solid tumor formation which results in a variety of cancers including but not limited to colorectal, pancreatic, breast, lung, prostate, and ovarian cancer.

In addition, PDGF aptamer compositions of the present invention can be used as anti-angiogenic agents to inhibit the formation of tumor vasculature by targeting pericytes. Alternatively, PDGF aptamer compositions of the present invention can be used in combination with a VEGF/VEGFR antagonist, such as an aptamer specific for VEGF, to provide a more effective way of inhibiting tumor angiogenesis than either a PDGF aptamer therapeutic or VEGF/VEGFR antagonists therapeutic alone. An advantage of the PDGF-B- and VEGF-targeting agents of the present invention is that the therapeutic compositions of the present invention do not appear to exhibit any off-target tyrosine kinase activity, since they are exquisitely specific to their target ligand, and are not designed to enter cells to elicit their biological function. In contrast, currently marketed small molecule kinase inhibitor therapeutics, for example GLEEVEC™, exhibit high off-target activity. GLEEVEC™ targets both the α and β tyrosine kinase receptors in addition to BCR-Abl, C-kit and Arg tyrosine kinases. Small molecule kinase inhibitors, such as GLEEVEC™, are administered at or near their maximum tolerated dose when used in the treatment of solid tumors. The toxicity of GLEEVEC™ and other tyrosine kinase inhibitors (TKIs) is likely limited by both mechanism-related side-effects and non-mechanism (off-target) related side-effects. Hence, off-target activity is a major impediment to the development of small molecule kinase inhibitors in general. Based on in vivo experiments with ARC127 (5'-[40K PEG]-(SEQ ID No.1)-HEG-(SEQ ID NO:2)-HEG-(SEQ ID NO:3)-3'-dT-3') and ARC308 (5'-[30K PEG]-(SEQ ID No.1)-HEG-(SEQ ID NO:2)-HEG-(SEQ ID NO:3)-3'-dT-3') dose-limiting side effects are not evident. Additional advantages are that the aptamer therapeutic compositions of the present invention can be administered via intravenous, subcutaneous, or intra-peritoneal routes, which means ease of administration. When compared to monoclonal antibody cancer therapeutics, aptamers are non-immunogenic, thus reaction to the drug or resistance to the drug are not an issue.

Aptamers to PDGF and PDGF Isoforms

The materials of the present invention comprise a series of nucleic acid aptamers of 31-35 nucleotides in length (SEQ ID NO:1 to SEQ ID NO:3, SEQ ID NO:9 to SEQ ID NO:38, SEQ ID NO:50, SEQ ID NO:54 to SEQ ID NO:90, and SEQ ID NO:94 to SEQ ID NO:99) which bind specifically to PDGF-B protein in vitro and which functionally block the activity of PDGF-BB in in vivo and cell-based assays. The anti-PDGF-B aptamers sequences of the present invention are derived from a parent molecule ARC126 (5'-(SEQ ID No.1)-HEG-(SEQ ID NO:2)-HEG-(SEQ ID NO:3)-3'-dT-3') which contains seven individual 2'F containing residues. 2'F containing residues were incorporated into ARC126 to increase the in vitro serum and in vivo stability of the therapeutic aptamer by blocking its degradation by serum endonucleases and/or exonucleases. In an effort to replace potentially toxic 2'F containing nucleotide residues in the ARC126 anti-PDGF-B aptamer, a new series of fully 2'F-free aptamers have been identified. The new aptamers of the present invention retain potent in vitro binding and anti-proliferative activity, and contain naturally occurring 2'deoxy or 2'OMe substituted nucleotides. These new aptamers of the present invention also retain substantial serum stability as determined through resistance to nuclease degradation in an in vitro stability assay, with no degradation detected for up to 48 hours.

The aptamer therapeutics of the present invention have great affinity and specificity to PDGF, PDGF isoforms, and PDGF receptor while reducing the deleterious side effects from non-naturally occurring nucleotide substitutions when the aptamer therapeutics break down in the body of patients or subjects. The therapeutic compositions containing the aptamer therapeutics of the present invention are free of or have a reduced amount of fluorinated nucleotides.

Materials and Methods to Increase the Efficacy of Anti-Tumor Agents

The materials and methods of the present invention further comprise methods to increase the efficacy of antitumor agents by dual therapy with the aptamers of the present invention, namely ARC127 and ARC308. In addition, the methods of the present invention have demonstrated that PDGF-B specific aptamers, ARC127 (i.e., ARC126+40K PEG) and ARC308 (i.e., ARC 126+30K PEG) are active anti-tumor agents when co-administered with irinotecan to nude mice bearing the colorectal LS174t tumor xenograft. The use of the cancer therapeutic methods of the present invention have shown that both ARC127 and ARC308 are safe non-cytotoxic agents when administered alone, but in combination with other cytotoxic agents, ARC127 and ARC308 potentiate their anti-tumor effects through a novel mechanism of action. The methods of the present invention further demonstrate that the serum-derived ARC127 aptamer when administered to mice parenterally, i.e. intravenously, subcutaneously, or by intraperitoneal injection, retains full biological activity.

Aptamer-Chimera Specific for PDGF-B and VEGF

The materials and methods of the present invention further provide bi-functional aptamer-chimera that target both PDGF-B and VEGF. The PDGF-B-VEGF aptamer chimera TK.131.12.A (SEQ ID No.9) and TK.131.12.B (SEQ ID No.10) of the present invention allow for the simultaneous targeting of PDGF-B and VEGF for the treatment of cancer. The PDGF-B aptamer used in the chimeric molecule is derived from the ARC127 aptamer sequence. The VEGF aptamer that was used in the chimeric molecule is derived from the ARC245 (SEQ ID No.7) aptamer sequence. The aptamer-chimera of the present invention can be constructed from any set of PDGF-B and VEGF binding aptamers. The PDGF-B-VEGF chimera of the present invention is useful in the treatment of VEGF-dependent solid tumors that also show a high degree of neovascularization as well as pericyte recruitment to support the nascent vasculature.

Recent anti-tumor data from the RipTag pancreatic mouse tumor model suggests that there is a greater block in tumor growth conferred when anti-VEGF and anti-PDGFR therapy are undertaken simultaneously, than when either the anti-VEGF agent or the anti-PDGFR agent is added alone (Bergers et al., (2003), J. Clin. Invest., 111:9, p. 1287-1295). Since, anti-PDGFR therapy blocks all receptor-mediated signaling events, its effects can be expected to be nonspecific. The PDGF-B-VEGF chimera in this invention provide for precise PDGF-B and VEGF targeting in tumors.

The aptamer therapeutics of the present invention have great affinity and specificity to VEGF, and VEGF receptor while reducing the deleterious side effects from non-naturally occurring nucleotide substitutions when the aptamer therapeutics break down in the body of patients or subjects. The therapeutic compositions of the aptamer therapeutics of the present invention are free of or have a reduced amount of fluorinated nucleotides.

Aptamers Having Immunostimulatory Motifs

Recognition of bacterial DNA by the vertebrate immune system is based on the recognition of unmethylated CG dinucleotides in particular sequence contexts ("CpG motifs"). One receptor that recognizes such a motif is Toll-like receptor 9 ("TLR 9"), a member of a family of Toll-like receptors (~10 members) that participate in the innate immune response by recognizing distinct microbial components. TLR 9 binds unmethylated oligodeoxynucleotide (ODN) CpG sequences in a sequence-specific manner. The recognition of CpG motifs triggers defense mechanisms leading to innate and ultimately acquired immune responses. For example, activation of TLR 9 in mice induces activation of antigen presenting cells, up regulation of MHC class I and II molecules and expression of important costimulatory molecules and cytokines including IL-12 and IL-23. This activation both directly and indirectly enhances B and T cell responses, including robust up regulation of the TH1 cytokine IFN-gamma. Collectively, the response to CpG sequences leads to: protection against infectious diseases, improved immune response to vaccines, an effective response against asthma, and improved antibody-dependent cell-mediated cytotoxicity. Thus, CpG ODN's can provide protection against infectious diseases, function as immunoadjuvants or cancer therapeutics (monotherapy or in combination with mAb or other therapies), and can decrease asthma and allergic response.

Aptamers comprising one or more CpG motifs can be identified or generated by a variety of strategies using, e.g., the SELEX™ process described herein. In general the strategies can be divided into two groups. In the first group, the strategies are directed to identifying or generating aptamers comprising both a binding site for targets other than those recognizing CpG motifs and a CpG motif. These strategies are as follows: (a) performing SELEX™ to obtain an aptamer to a specific target (other than a target known to bind to CpG motifs and upon binding stimulate an immune response), preferably a target where a repressed immune response is relevant to disease development, using an oligonucleotide pool wherein a CpG motif has been incorporated into each member of the pool as, or as part of, a fixed region, e.g., in the randomized region of the pool members; (b) performing SELEX to obtain an aptamer to a specific target (other than a target known to bind to CpG motifs and upon binding stimulate an immune response), preferably a target where a repressed immune response is relevant to disease development, and then appending a CpG motif to the 5' and/or 3' end or engineering a CpG motif into a region, preferably a non-essential region, of the aptamer; (c) performing SELEX™ to obtain an aptamer to a specific target (other than a target known to bind to CpG motifs and upon binding stimulate an immune response), preferably a target where a repressed immune response is relevant to disease development, wherein during synthesis of the pool the molar ratio of the various nucleotides is biased in one or more nucleotide addition steps so that the randomized region of each member of the pool is enriched in CpG motifs; and (d) performing SELEX™ to obtain an aptamer to a specific target (other than a target known to bind to CpG motifs and upon binding stimulate an immune response), preferably a target where a repressed immune response is relevant to disease development, and identifying those aptamers comprising a CpG motif.

In the second group, the strategies are directed to identifying or generating aptamers comprising a CpG motif and/or other sequences that are bound by the receptors for the CpG motifs (e.g., TLR9 or the other toll-like receptors) and upon binding stimulate an immune response. These strategies are as follows: (i) performing SELEX™ to obtain an aptamer to a target known to bind to CpG motifs and upon binding stimulate an immune response using an oligonucleotide pool wherein a CpG motif has been incorporated into each member of the pool as, or as part of, a fixed region, e.g., in the randomized region of the pool members; (ii) performing SELEX to obtain an aptamer to a target known to bind to CpG motifs and upon binding stimulate an immune response and then appending a CpG motif to the 5' and/or 3' end or engineering a CpG motif into a region, preferably a non-essential region, of the aptamer; (iii) performing SELEX to obtain an aptamer to a target known to bind to CpG motifs and upon binding stimulate an immune response wherein during synthesis of the pool, the molar ratio of the various nucleotides is biased in one or more nucleotide addition steps so that the randomized region of each member of the pool is enriched in CpG motifs; (iv) performing SELEX to obtain an aptamer to a target known to bind to CpG motifs and upon binding stimulate an immune response and identifying those aptamers comprising a CpG motif; and (v) performing SELEX to obtain an aptamer to a target known to bind to CpG motifs and identifying those aptamers which, upon binding, stimulate an immune response not comprising a CpG motif.

A variety of different classes of CpG motifs have been identified, each resulting upon recognition in a different cascade of events, release of cytokines and other molecules, and activation of certain cell types. See, e.g., CpG Motifs in Bacterial DNA and Their Immune Effects, Annu. Rev. Immunol. 2002, 20:709-760, incorporated herein by reference. Additional immunostimulatory motifs are disclosed in the following U.S. Patents, each of which is incorporated herein by reference: U.S. Pat. Nos. 6,207,646; 6,239,116; 6,429,199; 6,214,806; 6,653,292; 6,426,434; 6,514,948 and 6,498,148. Any of these CpG or other immunostimulatory motifs can be incorporated into an aptamer. The choice of aptamers is dependent on the disease or disorder to be treated. Preferred immunostimulatory motifs are as follows (shown the 5' to 3' left to right) wherein "r" designates a purine, "y" designates a pyrimidine, and "X" designates any nucleotide: AACGTTCGAG (SEQ ID NO:37); AACGTT; ACGT, rCGy; rrCGyy, XCGX, XXCGXX, and $X_1X_2CGY_1Y_2$ wherein $X_1$ is G or A, $X_2$ is not C, $Y_1$ is not G and $Y_2$ is preferably T.

In those instances where a CpG motif is incorporated into an aptamer that binds to a specific target other than a target known to bind to CpG motifs and upon binding stimulate an immune response (a "non-CpG target"), the CpG is preferably located in a non-essential region of the aptamer. Non-essential regions of aptamers can be identified by site-directed mutagenesis, deletion analyses and/or substitution analyses. However, any location that does not significantly interfere with the ability of the aptamer to bind to the non-CpG target may be used. In addition to being embedded within the aptamer sequence, the CpG motif may be appended to either or both of the 5' and 3' ends or otherwise attached to the aptamer. Any location or means of attachment may be used so long as the ability of the aptamer to bind to the non-CpG target is not significantly interfered with.

As used herein, "stimulation of an immune response" can mean either (1) the induction of a specific response (e.g., induction of a Th1 response) or of the production of certain molecules or (2) the inhibition or suppression of a specific response (e.g., inhibition or suppression of the Th2 response) or of certain molecules.

CpG motifs can be incorporated or appended to an aptamer against any target including, but not limited to: PDGF, IgE, IgE Fcε R1, TNFa, PSMA, CTLA4, PD-1, PD-L1, PD-L2, FcRIIB, BTLA, TIM-3, CD11b, CD-11c, BAFF, B7-X, CD19, CD20, CD25 and CD33.

By incorporating CpG motifs into aptamers specifically targeting solid tumors these aptamers can be used to activate the immune system through the recruitment of antigen presenting cells that have taken up tumor derived material, enhance their maturation and migration to local lymph nodes and increase priming of tumor specific T-cells. This is especially relevant where aptamers deliver cytotoxic payload and result in cell death (such as a PSMA aptamer containing a CpG motif). Such CpG motif containing aptamers can also induce tumor-specific memory response (prophylactic use). In addition, the IFP lowering and pericyte recruitment blocking effects of a PDGF-B aptamer combined with the increased immune response observed upon CpG administration represents a potent therapeutic for cancer. Thus, aptamers with incorporated, appended or embedded CpG motifs represent a novel class of anti-cancer compounds such that when administered they can lead to a significant de-bulking of the tumor through two mechanisms: first, through activation of tumor specific T-cells within the tumor bed and second, through the intended mechanism-based action of the aptamer pharmacophore.

Pharmaceutical Compositions

The invention also includes pharmaceutical compositions containing aptamer molecules. In some embodiments, the compositions are suitable for internal use and include an effective amount of a pharmacologically active compound of the invention, alone or in combination, with one or more pharmaceutically acceptable carriers. The compounds are especially useful in that they have very low, if any toxicity.

Compositions of the invention can be used to treat or prevent a pathology, such as a disease or disorder, or alleviate the symptoms of such disease or disorder in a patient. Compositions of the invention are useful for administration to a subject suffering from, or predisposed to, a disease or disorder which is related to or derived from a target to which the aptamers specifically bind.

For example, the target is a protein involved with a pathology, for example, the target protein causes the pathology. For example, the target is PDGF involvement in the development and progression of solid tumors.

Compositions of the invention can be used in a method for treating a patient or subject having a pathology. The method involves administering to the patient or subject a composition comprising aptamers that bind a target (e.g., a protein) involved with the pathology, so that binding of the composition to the target alters the biological function of the target, thereby treating the pathology.

The patient or subject having a pathology, e.g. the patient or subject treated by the methods of this invention can be a mammal, or more particularly, a human.

In practice, the compounds or their pharmaceutically acceptable salts, are administered in amounts which will be sufficient to exert their desired biological activity, e.g., inhibiting the binding of a cytokine to its receptor.

One aspect of the invention comprises an aptamer composition of the invention in combination with other treatments for cancer or cancer related disorders. The aptamer composition of the invention may contain, for example, more than one aptamer. In some examples, an aptamer composition of the invention, containing one or more compounds of the invention, is administered in combination with another useful composition such as an anti-inflammatory agent, an immunosuppressant, an antiviral agent, or the like. Furthermore, the compounds of the invention may be administered in combination with a cytotoxic, cytostatic, or chemotherapeutic agent such as an alkylating agent, antimetabolite, mitotic inhibitor or cytotoxic antibiotic, as described above. In general, the currently available dosage forms of the known therapeutic agents for use in such combinations will be suitable.

"Combination therapy" (or "co-therapy") includes the administration of an aptamer composition of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

Therapeutic or pharmacological compositions of the present invention will generally comprise an effective amount of the active component(s) of the therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

The compounds of the invention can also be administered in such oral dosage forms as timed release and sustained release tablets or capsules, pills, powders, granules, elixirs, tinctures, suspensions, syrups and emulsions.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.01% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the aptamer molecules described herein can be provided as a complex with a lipophilic compound or non-immunogenic, high molecular weight compound constructed using methods known in the art. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 5000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the compounds of the present invention range from 0.002 mg to 50 mg per kg of body weight per day.

Compounds of the present invention may be administered in a single daily dose, or the total daily dosage may be administered in divided doses of two, three or four times daily.

Modulation of Pharmacokinetics and Biodistribution of Aptamer Therapeutics

The present invention provides materials and methods to affect the pharmacokinetics of aptamer compositions, and, in particular, the ability to tune (i.e., the "tunability") aptamer pharmacokinetics. The tunability of aptamer pharmacokinetics is achieved through conjugation of modifying moieties to the aptamer and/or the incorporation of modified nucleotides to alter the chemical composition of the nucleic acid. The ability to tune aptamer pharmacokinetics is used in the improvement of existing therapeutic applications, or alternatively, in the development of new therapeutic applications. For example, in some therapeutic applications, e.g., in anti-neoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it may be desirable to increase the residence times of aptamers in circulation.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described herein, PEGylation of an aptamer therapeutic (e.g. PEGylation with a 20 kDa PEG polymer) is used to target inflamed tissues, such that the PEGylated aptamer therapeutic preferentially accumulates in inflamed tissue.

The pharmacokinetic and biodistribution profiles of aptamer therapeutics (e.g., aptamer conjugates or aptamers having altered chemistries, such as modified nucleotides) are determined by monitoring a variety of parameters. Such parameters include, for example, the half-life ($t_{1/2}$), the plasma clearance (Cl), the volume of distribution (Vss), the area under the concentration-time curve (AUC), maximum observed serum or plasma concentration ($C_{max}$), and the mean residence time (MRT) of an aptamer composition. As used herein, the term "AUC" refers to the area under the plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (Cl) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

The pharmacokinetic and biodistribution properties of phosphorothioate-containing antisense oligonucleotides, which clear rapidly from circulation, and distribute into tissues (where elimination occurs slowly, as a result of metabolic degradation) are described in the art: (See e.g., Srinivasan and Iversen (1995), J. Clin. Lab. Anal. 9(2): 129-37; Agrawal and Zhang (1997), Ciba Found. Symp. 209: 60-75, discussion 75-8; Akhtar and Agrawal (1997), Trends Pharmacol. Sci. 18(1): 12-8; Crooke (1997), Adv. Pharmacol. 40: 1-49; Grindel, et al. (1998), Antisense Nucleic Acid Drug Dev. 8(1): 43-52; Monteith and Levin (1999), Toxicol. Pathol. 27(1): 8-13; Peng, et al. (2001), Antisense Nucleic Acid Drug Dev. 11(1): 15-27). Early studies involving antisense oligonucleotides have explored the effects of various conjugation chemistries on pharmacokinetics and biodistribution, with the ultimate goal of increasing delivery of antisense molecules to their sites of action inside cells or within certain tissue types in vivo (Antopolsky, et al. (1999), Bioconjug. Chem. 10(4): 598-606; Zubin, et al. (1999), FEBS Lett. 456(1): 59-62; Astriab-Fisher, et al. (2000), Biochem. Pharmacol. 60(1): 83-90; Lebedeva, et al., (2000), Eur. J. Pharm. Biopharm. 50(1): 101-19; Manoharan (2002), Antisense Nucleic Acid Drug Dev. 12(2): 103-28). For example, conjugation with cholesterol has been reported to increase the circulation half-life of antisense oligonucleotides, most likely through association with plasma lipoproteins, and promoting hepatic uptake (de Smidt, et al. (1991), Nucleic Acids Res. 19(17): 4695-4700). Early work involving antisense oligonucleotides has indicated that nonspecific protein-binding interactions play an important role in the rapid loss of phosphorothioate-containing antisense oligonucleotide from circulation and distribution to tissues (See e.g., Srinivasan and Iversen (1995), J. Clin. Lab. Anal. 9(2): 129-37; Agrawal and Zhang (1997), Ciba Found. Symp. 209: 60-75, discussion 75-8; Akhtar and Agrawal (1997), Trends Pharmacol. Sci 18(1): 12-8; Crooke (1997), Adv. Pharmacol. 40: 1-49; Grindel, et al. (1998), Antisense Nucleic Acid Drug Dev. 8(1): 43-52; Monteith and Levin (1999), Toxicol. Pathol. 27(1): 8-13; Peng, et al. (2001), Antisense Nucleic Acid Drug Dev. 11(1): 15-27).

In contrast to antisense oligonucleotides, aptamers are generally longer (30-40 vs. 10-20 nucleotides), possess different types of chemical modifications (sugar modifications, e.g., 2'-F, 2'-O-Me, 2'-NH$_2$, vs. backbone modifications), and assume complex tertiary structures that are more resistant to degradation. Aptamers are, in many respects, more structurally similar to the three dimensional forms of globular proteins than to nucleic acids. Given these considerable differences, the in vivo disposition of aptamers is not readily predictable from antisense results.

More recently, delivery peptides for carrying large polar macromolecules, including oligonucleotides, across cellular membranes have also been explored as a means to augment in vivo the range for application of antisense and other therapeutics. Examples of these conjugates include a 13-amino acid fragment (Tat) of the HIV Tat protein (Vives, et al. (1997), J. Biol. Chem. 272(25): 16010-7), a 16-amino acid sequence derived from the third helix of the *Drosophila antennapedia* (Ant) homeotic protein (Pietersz, et al. (2001), Vaccine 19(11-12): 1397-405), and short, positively charged cell-permeating peptides composed of polyarginine ($Arg_7$) (Rothbard, et al. (2000), Nat. Med. 6(11): 1253-7; Rothbard, J et al. (2002), J. Med. Chem. 45(17): 3612-8). For example, the TAT peptide is described in U.S. Pat. Nos. 5,804,604 and 5,674,980.

The present invention provides materials and methods to modulate, in a controlled manner, the pharmacokinetics and biodistribution of stabilized aptamer compositions in vivo by conjugating an aptamer to a modulating moiety such as a small molecule, peptide, or polymer terminal group, or by incorporating modified nucleotides into an aptamer. Pharmacokinetics and biodistribution of aptamer conjugates in biological samples are quantified radiometrically and by a hybridization-based dual probe capture assay with enzyme-linked fluorescent readout. As described herein, conjugation of a modifying moiety and/or altering nucleotide(s) chemical composition alter fundamental aspects of aptamer residence time in circulation and distribution to tissues.

Aptamers are conjugated to a variety of modifying moieties, such as, for example, high molecular weight polymers, e.g., PEG, peptides, e.g., Tat, Ant and $Arg_7$, and small molecules, e.g., lipophilic compounds such as cholesterol. As shown herein, a mixed composition aptamer containing both 2'F and 2'-OMe stabilizing modifications persisted significantly longer in the blood stream than did a fully 2'-O-methylated composition. Among the conjugates prepared according to the materials and methods of the present invention, in vivo properties of aptamers were altered most profoundly by complexation with PEG groups. For example complexation of the mixed 2'F and 2'-OMe modified aptamer therapeutic with a 20 kDa PEG polymer hindered renal filtration and promoted aptamer distribution to both healthy and inflamed tissues. Furthermore, the 20 kDa PEG polymer-aptamer conjugate proved nearly as effective as a 40 kDa PEG polymer in preventing renal filtration of aptamers. While one effect of PEGylation was on aptamer clearance, the prolonged systemic exposure afforded by presence of the 20 kDa moiety also facilitated distribution of aptamer to tissues, particularly those of highly perfused organs and those at the site of inflammation. The aptamer-20 kDa PEG polymer conjugate (ARC120) directed aptamer distribution to the site of inflammation, such that the PEGylated aptamer preferentially accumulated in inflamed tissue. In some instances, the 20 kDa PEGylated aptamer conjugate was able to access the interior of cells, such as, for example, kidney cells.

Overall, effects on aptamer pharmacokinetics and tissue distribution produced by low molecular weight modifying moieties, including cholesterol and cell-permeating peptides were less pronounced than those produced as a result of PEGylation or modification of nucleotides (e.g., an altered chemical composition). An aptamer conjugated to cholesterol showed more rapid plasma clearance relative to unconjugated aptamer, and a large volume of distribution, which suggests some degree of aptamer extravasation. This result appears to contrast published data demonstrating the capacity of a cholesterol tag to significantly prolong the plasma half-life of an antisense oligonucleotide (de Smidt et al., (1991), Nucleic Acids Res. 19(17): 4695-4700). While not intending to be bound by theory, the results provided herein, may suggest that cholesterol-mediated associations with plasma lipoproteins, postulated to occur in the case of the antisense conjugate, are precluded in the particular context of the aptamer-cholesterol conjugate folded structure, and/or relate to aspect of the lipophilic nature of the cholesterol group. Like cholesterol, the presence of a Tat peptide tag promoted clearance of aptamer from the blood stream, with comparatively high levels of conjugate appearing in the kidneys at 48 hrs. Other peptides (e.g., Ant, $Arg_7$) that have been reported in the art to mediate passage of macromolecules across cellular membranes in vitro, did not appear to promote aptamer clearance from circulation. However, like Tat, the Ant conjugate significantly accumulated in the kidneys relative to other aptamers. While not intending to be bound by theory, it is possible that unfavorable presentation of the Ant and $Arg_7$ peptide modifying moieties in the context of three dimensionally folded aptamers in vivo impaired the ability of these peptides to influence aptamer transport properties.

Prior to the invention described herein, little was known concerning the pharmacokinetics and biodistribution of oligonucleotides with a 2'-OMe chemical composition (Tavitian, et al. (1998), Nat. Med. 4(4): 467-71). For several reasons, incorporation of 2'-OMe substitutions is a particularly attractive means to stabilize aptamers against nuclease attack. One attribute is safety: 2'-O-methylation is known as a naturally occurring and abundant chemical modification in eukaryotic ribosomal and cellular RNAs. Human rRNAs are estimated to contain roughly one hundred 2'-O-methylated sugars per ribosome (Smith and Steitz (1997), Cell 89(5): 669-72). Thus, aptamer compositions incorporating 2'-OMe substitutions are expected to be non-toxic. In support of this view, in vitro and in vivo studies indicate that 2'-OMe nucleotides are not readily polymerized by human DNA polymerases (α or γ), or by human DNA primase, and thus, pose a low risk for incorporation into genomic DNA (Richardson, et al. (2000), Biochem. Pharmacol. 59(9): 1045-52; Richardson, et al. (2002), Chem. Res. Toxicol. 15(7): 922-6). Additionally, from a cost of goods perspective, pricing per gram for synthesis of 2'-OMe containing oligonucleotides is less than the pricing per gram for both 2'-F and 2'-OH containing RNAs.

A comparison of a mixed 2'F/2'-OMe composition aptamer and conjugated aptamers was conducted in vivo to determine plasma clearance. The unconjugated test aptamer which incorporates both 2'-F and 2'-OMe stabilizing chemistries, is typical of current generation aptamers as it exhibits a high degree of nuclease stability in vitro and in vivo. Compared to the mixed 2'F/2'-OMe composition aptamer, unmodified aptamer displayed rapid loss from plasma (i.e., rapid plasma clearance) and a rapid distribution into tissues, primarily into the kidney.

Tests can be conducted to determine whether the hydrophobic nature of a fully 2'-OMe modified aptamer renders the oligonucleotide more prone to nonspecific associations with plasma or cellular component (as is the case with antisense oligonucleotides). In addition, experiments can be conducted to define the protein-binding properties of 2'-OMe-modified aptamers. While not intending to be bound by theory, levels of full-length all-2'-O-methyl substituted aptamer above background were detected in several tissues, kidney, liver, and spleen, even at 48 hrs after dosing, possibly due to the extreme robustness of the fully 2'-OMe aptamer towards nuclease digestion. In one example, consistent with its plasma clearance profile and distribution to the kidney, a fully 2'-OMe aptamer was eliminated rapidly via the urine.

When expressed as percent of administered dose, all aptamers or conjugates examined herein showed significant levels of distribution to kidney, liver, and gastrointestinal tract. When corrected for organ/tissue weight, highest mass-normalized concentrations of aptamers were seen in highly perfused organs (kidneys, liver, spleen, heart, lungs) and unexpectedly, mediastinal lymph nodes. Since aptamers are bioavailable (up to 80%) following subcutaneous injection (Tucker et al., (1999), J. Chromatography B. 732: 203-212), they are expected to have access to targets in the lymphatic system through this route of administration. Ready access to the lymphatics via intravenous dosing is of interest from the standpoint of developing aptamer therapeutics for infectious disease indications such as HIV/AIDS. Thus, aptamer therapeutics conjugated to modifying moieties and aptamers having altered chemistries (e.g., including modified nucleotides) will be useful in the treatment of infectious diseases such as HIV/AIDS.

Consistent with its enhanced plasma pharmacokinetics, the concentration of 20 kDa PEGylated aptamer detected in highly perfused organs was higher than for the other aptamers that were assayed. As a general trend, aptamer concentrations measured in the kidneys decreased with time, with exception of 20 kDa PEGylated aptamer, where concentrations remained roughly constant over time. Conversely, in liver concentrations of all aptamers remained roughly constant, except for 20 kDa PEGylated aptamer, whose levels decreased with time. These differences may be understood in terms of the extended plasma half-life of the 20 kDa PEG conjugate and its increased uptake in highly perfused organs. While one of the effects of complexation with a 20 kDa PEG modifying moiety was to retard renal filtration of the aptamer conjugate, the comparatively high concentrations of the 20 kDa PEG conjugate measured in well-perfused organs, relative to other aptamers or conjugates, suggested that PEGylation can modulate aptamer distribution to tissues, as well as promote extended plasma half-life ($t_{1/2}$). As described herein, the 20 kDa PEGylated aptamer-conjugate modulated aptamer distribution to tissues. The level of the 20 kDa PEGylated aptamer detected in inflamed tissues was higher than for the other aptamers that were assayed, and, in some instances, the aptamer was able to access the interior of cells (e.g. kidney cells).

While not intending to be bound by theory, it is speculated that prolonged residence in the blood stream increases exposure of conjugated aptamer to tissues, leading to enhanced uptake, which is most pronounced in the case of highly perfused organs and in the case of inflamed tissues. The presence of aptamer in residual blood may contribute to, but is unlikely to account entirely for, the increased levels of the 20 kDa aptamer conjugate in perfused organs and inflamed tissue shown herein. The enhanced distribution of PEGylated aptamer to perfused organs and inflamed tissues represents extravasation, as suggested by experiments in mice dosed with tritiated 20 kDa PEG conjugate where [$^3$H] signal was seen in cells of both the liver and kidney (See Examples provided below). Early work on aptamer therapeutics focused primarily on development of aptamers complexed with higher molecular weight (40 kDa) PEG species in an effort to avoid renal filtration (Reyderman and Stavchansky (1998), Pharmaceutical Research 15(6): 904-10; Tucker et al., (1999), J. Chromatography B. 732: 203-212; Watson, et al. (2000), Antisense Nucleic Acid Drug Dev. 10(2): 63-75; Carrasquillo, et al. (2003), Invest. Ophthalmology Vis. Sci. 44(1): 290-9). The present invention indicates that complexation with a smaller, e.g., 20 kDa, PEG polymer sufficiently protects aptamer-based drugs from renal filtration for many therapeutic indications. Smaller PEGs (e.g., 10 kDa to 20 kDa PEG moieties) also provide the collateral benefits of ease of synthesis and reduced cost of goods, as compared to larger PEGs.

PEG-Derivatized Nucleic Acids

Derivatization of nucleic acids with high molecular weight non-immunogenic polymers has the potential to alter the pharmacokinetic and pharmacodynamic properties of nucleic acids making them more effective therapeutic agents. Favorable changes in activity can include increased resistance to degradation by nucleases, decreased filtration through the kidneys, decreased exposure to the immune system, and altered distribution of the therapeutic through the body.

The aptamer compositions of the invention may be derivatized with polyalkylene glycol (PAG) moieties. Examples of PAG-derivatized nucleic acids are found in U.S. patent application Ser. No. 10/718,833, filed on Nov. 21, 2003, which is herein incorporated by reference in its entirety. Typical polymers used in the invention include poly(ethylene glycol) (PEG), also known as or poly(ethylene oxide) (PEO) and polypropylene glycol (including poly isopropylene glycol). Additionally, random or block copolymers of different alkylene oxides (e.g., ethylene oxide and propylene oxide) can be used in many applications. In its most common form, a polyalkylene glycol, such as PEG, is a linear polymer terminated at each end with hydroxyl groups: HO—CH$_2$CH$_2$O—(CH$_2$CH$_2$O)$_n$—CH$_2$CH$_2$—OH. This polymer, alpha-, omega-dihydroxylpoly(ethylene glycol), can also be represented as HO—PEG-OH, where it is understood that the —PEG-symbol represents the following structural unit: —CH$_2$CH$_2$O—(CH$_2$CH$_2$O)$_n$—CH$_2$CH$_2$— where n typically ranges from about 4 to about 10,000.

As shown, the PEG molecule is di-functional and is sometimes referred to as "PEG diol." The terminal portions of the PEG molecule are relatively non-reactive hydroxyl moieties, the —OH groups, that can be activated, or converted to functional moieties, for attachment of the PEG to other compounds at reactive sites on the compound. Such activated PEG diols are referred to herein as bi-activated PEGs. For example, the terminal moieties of PEG diol have been functionalized as active carbonate ester for selective reaction with amino moieties by substitution of the relatively nonreactive hydroxyl moieties, —OH, with succinimidyl active ester moieties from N-hydroxy succinimide.

In many applications, it is desirable to cap the PEG molecule on one end with an essentially non-reactive moiety so that the PEG molecule is mono-functional (or mono-activated). In the case of protein therapeutics which generally display multiple reaction sites for activated PEGs, bi-functional activated PEGs lead to extensive cross-linking, yielding poorly functional aggregates. To generate mono-activated PEGs, one hydroxyl moiety on the terminus of the PEG diol molecule typically is substituted with non-reactive methoxy end moiety, —OCH$_3$. The other, un-capped terminus of the PEG molecule typically is converted to a reactive end moiety that can be activated for attachment at a reactive site on a surface or a molecule such as a protein.

PAGs are polymers which typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995). PAG conjugates are often used not only to enhance solubility and stability but also to prolong the blood circulation half-life of molecules.

Polyalkylated compounds of the invention are typically between 5 and 80 kD in size. Other PAG compounds of the invention are between 10 and 80 kD in size. Still other PAG compounds of the invention are between 10 and 60 kD in size. For example, a PAG polymer may be at least 10, 20, 30, 40, 50, 60, or 80 kD in size. Such polymers can be linear or branched.

In contrast to biologically-expressed protein therapeutics, nucleic acid therapeutics are typically chemically synthesized from activated monomer nucleotides. PEG-nucleic acid conjugates may be prepared by incorporating the PEG using the same iterative monomer synthesis. For example, PEGs activated by conversion to a phosphoramidite form can be incorporated into solid-phase oligonucleotide synthesis. Alternatively, oligonucleotide synthesis can be completed with site-specific incorporation of a reactive PEG attachment site. Most commonly this has been accomplished by addition of a free primary amine at the 5'-terminus (incorporated using a modifier phosphoramidite in the last coupling step of solid phase synthesis). Using this approach, a reactive PEG (e.g., one which is activated so that it will react and form a bond with an amine) is combined with the purified oligonucleotide and the coupling reaction is carried out in solution.

The ability of PEG conjugation to alter the biodistribution of a therapeutic is related to a number of factors including the apparent size (e.g., as measured in terms of hydrodynamic radius) of the conjugate. Larger conjugates (>10 kDa) are known to more effectively block filtration via the kidney and to consequently increase the serum half-life of small macromolecules (e.g., peptides, antisense oligonucleotides). The ability of PEG conjugates to block filtration has been shown to increase with PEG size up to approximately 50 kDa (flirter increases have minimal beneficial effect as half life becomes defined by macrophage-mediated metabolism rather than elimination via the kidneys).

Production of high molecular weight PEGs (>10 kDa) can be difficult, inefficient, and expensive. As a route towards the synthesis of high molecular weight PEG-nucleic acid conjugates, previous work has been focused towards the generation of higher molecular weight activated PEGs. One method for generating such molecules involves the formation of a branched activated PEG in which two or more PEGs are attached to a central core carrying the activated group. The terminal portions of these higher molecular weight PEG molecules, i.e., the relatively non-reactive hydroxyl (—OH) moieties, can be activated, or converted to functional moieties, for attachment of one or more of the PEGs to other compounds at reactive sites on the compound. Branched activated PEGs will have more than two termini, and in cases where two or more termini have been activated, such activated higher molecular weight PEG molecules are referred to herein as, multi-activated PEGs. In some cases, not all termini in a branch PEG molecule are activated. In cases where any two termini of a branch PEG molecule are activated, such PEG molecules are referred to as bi-activated PEGs. In some cases where only one terminus in a branch PEG molecule is activated, such PEG molecules are referred to as mono-activated. As an example of this approach, activated PEG prepared by the attachment of two monomethoxy PEGs to a lysine core which is subsequently activated for reaction has been described (Harris et al., Nature, vol. 2: 214-221, 2003).

The present invention provides another cost effective route to the synthesis of high molecular weight PEG-nucleic acid (preferably, aptamer) conjugates including multiply PEGylated nucleic acids. The present invention also encompasses PEG-linked multimeric oligonucleotides, e.g., dimerized aptamers. The present invention also relates to high molecular weight compositions where a PEG stabilizing moiety is a linker which separates different portions of an aptamer, e.g., the PEG is conjugated within a single aptamer sequence, such that the linear arrangement of the high molecular weight aptamer composition is, e.g., nucleic acid—PEG—nucleic acid—PEG—nucleic acid.

High molecular weight compositions of the invention include those having a molecular weight of at least 10 kD. Compositions typically have a molecular weight between 10 and 80 kD in size. High molecular weight compositions of the invention are at least 10, 20, 30, 40, 50, 60, or 80 kD in size.

A stabilizing moiety is a molecule, or portion of a molecule, which improves pharmacokinetic and pharmacodynamic properties of the high molecular weight aptamer compositions of the invention. In some cases, a stabilizing moiety is a molecule or portion of a molecule which brings two or more aptamers, or aptamer domains, into proximity, or provides decreased overall rotational freedom of the high molecular weight aptamer compositions of the invention. A stabilizing moiety can be a polyalkylene glycol, such a polyethylene glycol, which can be linear or branched, a homopolymer or a heteropolymer. Other stabilizing moieties include polymers such as peptide nucleic acids (PNA). Oligonucleotides can also be stabilizing moieties; such oligonucleotides can include modified nucleotides, and/or modified linkages, such as phosphorothioates. A stabilizing moiety can be an integral part of an aptamer composition, i.e., it is covalently bonded to the aptamer.

Compositions of the invention include high molecular weight aptamer compositions in which two or more nucleic acid moieties are covalently conjugated to at least one polyalkylene glycol moiety. The polyalkylene glycol moieties serve as stabilizing moieties. In compositions where a polyalkylene glycol moiety is covalently bound at either end to an aptamer, such that the polyalkylene glycol joins the nucleic acid moieties together in one molecule, the polyalkylene glycol is said to be a linking moiety. In such compositions, the primary structure of the covalent molecule includes the linear arrangement nucleic acid-PAG-nucleic acid. One example is a composition having the primary structure nucleic acid-PEG-nucleic acid. Another example is a linear arrangement of: nucleic acid—PEG—nucleic acid—PEG—nucleic acid.

To produce the nucleic acid—PEG—nucleic acid conjugate, the nucleic acid is originally synthesized such that it bears a single reactive site (e.g., it is mono-activated). In a preferred embodiment, this reactive site is an amino group introduced at the 5'-terminus by addition of a modifier phosphoramidite as the last step in solid phase synthesis of the oligonucleotide. Following deprotection and purification of the modified oligonucleotide, it is reconstituted at high concentration in a solution that minimizes spontaneous hydrolysis of the activated PEG. In a preferred embodiment, the concentration of oligonucleotide is 1 mM and the reconstituted solution contains 200 mM NaHCO$_3$-buffer, pH 8.3. Synthesis of the conjugate is initiated by slow, step-wise addition of highly purified bi-functional PEG. In a preferred embodiment, the PEG diol is activated at both ends (bi-activated) by derivatization with succinimidyl propionate. Following reaction, the PEG-nucleic acid conjugate is purified by gel electrophoresis or liquid chromatography to separate fully-, partially-, and un-conjugated species. Multiple PAG molecules concatenated (e.g., as random or block copolymers) or smaller PAG chains can be linked to achieve various lengths (or molecular weights). Non-PAG linkers can be used between PAG chains of varying lengths.

The 2'-O-methyl, 2'-fluoro modifications stabilize the aptamer against nucleases and increase its half life in vivo. The 3'-3'-dT cap also increases exonuclease resistance. See, e.g., U.S. Pat. Nos. 5,674,685; 5,668,264; 6,207,816; and 6,229,002, each of which is incorporated by reference herein in its entirety.

PAG-Derivatization of a Reactive Nucleic Acid

Figure 22:
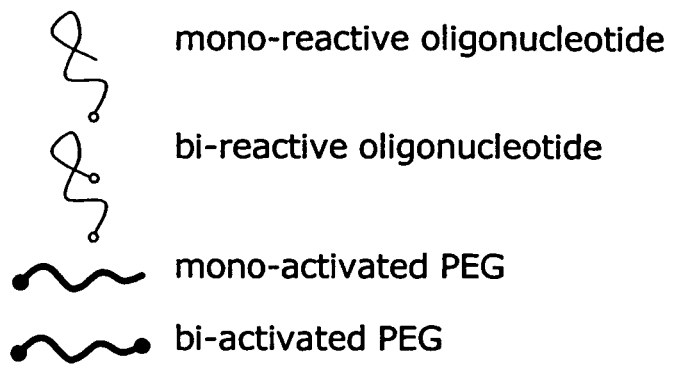
FIG. 22 is an illustration depicting various strategies for synthesis of high molecular weight PEG-nucleic acid conjugates.
Figure 22:
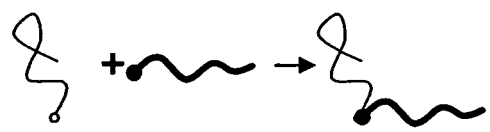
Figure 22:
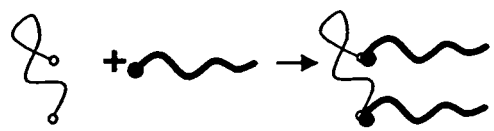
Figure 22:
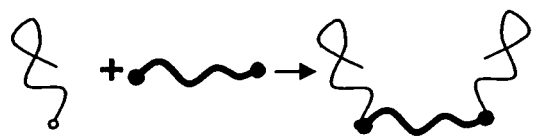

High molecular weight PAG-nucleic acid-PAG conjugates can be prepared by reaction of a mono-functional activated PEG with a nucleic acid containing more than one reactive site. In one embodiment, the nucleic acid is bi-reactive, or bi-activated, and contains two reactive sites: a 5'-amino group and a 3'-amino group introduced into the oligonucleotide through conventional phosphoramidite synthesis, for example: 3'-5'-di-PEGylation as illustrated in FIG. 22. In alternative embodiments, reactive sites can be introduced at internal positions, using for example, the 5-position of pyrimidines, the 8-position of purines, or the 2'-position of ribose as sites for attachment of primary amines. In such embodiments, the nucleic acid can have several activated or reactive sites and is said to be multiply activated. Following synthesis and purification, the modified oligonucleotide is combined with the mono-activated PEG under conditions that promote selective reaction with the oligonucleotide reactive sites while minimizing spontaneous hydrolysis. In the preferred embodiment, monomethoxy-PEG is activated with succinimidyl propionate and the coupled reaction is carried out at pH 8.3. To drive synthesis of the bi-substituted PEG, stoichiometric excess PEG is provided relative to the oligonucleotide. Following reaction, the PEG-nucleic acid conjugate is purified by gel electrophoresis or liquid chromatography to separate fully-, partially-, and un-conjugated species.

The linking domains can also have one ore more poly-alkylene glycol moieties attached thereto. Such PAGs can be of varying lengths and may be used in appropriate combinations to achieve the desired molecular weight of the composition.

The effect of a particular linker can be influenced by both its chemical composition and length. A linker that is too long, too short, or forms unfavorable steric and/or ionic interactions with the target will preclude the formation of complex between aptamer and target. A linker, which is longer than necessary to span the distance between nucleic acids, may reduce binding stability by diminishing the effective concentration of the ligand. Thus, it is often necessary to optimize linker compositions and lengths in order to maximize the affinity of an aptamer to a target.

All publications and patent documents cited herein are incorporated by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Large Scale Aptamer Synthesis and Conjugation

ARC126 (5'-(SEQ ID NO:1)-HEG-(SEQ ID NO:2)-HEG-(SEQ ID NO:3)-3' dT-3') is a 29 nucleotide aptamer (excluding an inverted T at the 3' end) specific for PDGF which contains a 3' inverted-dT cap for enhanced stability against nuclease attack. PEG moieties can be conjugated to ARC126 by using a 5'-amino terminus modifier for subsequent conjugation reactions. Syntheses were performed using standard solid-phase phosphoramidite chemistry. The oligonucleotide was deprotected with ammonium hydroxide/methylamine (1:1) at room temperature for 12 hours and purified by ion exchange HPLC. ARC 128 (5'-(SEQ ID No.4)-HEG-(SEQ ID NO:5)-HEG-(SEQ ID NO:6)-3'), an inactive variant which no longer binds PDGF, was synthesized using the same method.

ARC126 was conjugated to several different PEG moieties: 20 kDa PEG (ARC240, (5'-[20K PEG]-(SEQ ID NO:1)-HEG-(SEQ ID NO:2)-HEG-(SEQ ID NO:3)-3' dT-3')); 30 kDa PEG (ARC308, (5'-[30K PEG]-(SEQ ID NO:1)-HEG-(SEQ ID NO:2)-HEG-(SEQ ID NO:3)-3' dT-3')); 40 kDa PEG (ARC127, (5'-[40K PEG]-(SEQ ID NO:1)-HEG-(SEQ ID NO:2)-HEG-(SEQ ID NO:3)-3' dT-3')). ARC126 was dissolved to 2 mM in 100 mM sodium carbonate buffer, pH 8.5, and was reacted for 1 hour with a 2.5 molar excess of mPEG-SPA (MW 20 kDa) or mPEG2-NHS ester (MW 40 kDa) (Shearwater Corp., Huntsville, Ala.), and 3.5 molar excess (for 24 hours) of mPEG-nPNC (MW 30 kDa) (NOF Corporation, Tokyo, Japan) in equal volumes of acetonitrile. The resulting products were then purified by ion exchange HPLC on a 50 ml Super Q 5PW column (Tosoh Bioscience, Montgomeryville, Pa.) using aqueous NaCl as eluent. The conjugated oligonucleotides were then desalted on a 100 ml Amberchrom CG300S (Tosoh) column using a water/acetonitrile gradient. Aptamer conjugates were lyophilized for storage.

In order to be able to use ARC127 in animal models, the quality of the material synthesized needed to be tested for endotoxin levels. Endotoxin content of synthesized ARC127 was determined using the LAL test (performed by Nelson Labs, AZ). Results for endotoxin testing are shown in Table 1 below. The detected quantities of endotoxin were below the ISO standard for sterile irrigation solutions (0.5 EU/mL), i.e. lower than levels allowed for IV administration. This indicated that ARC 126 and ARC127 preparations were sterile and that it was possible to proceed to animal efficacy models.

TABLE 1

Endotoxin levels in large scale synthesis of therapeutic aptamers.

| Sample | Dilution | Endotoxin detected | Spike recovery |
|---|---|---|---|
| ARC126 | 1:10 | 2.5 EU/ml & 0.52 EU/mg | 73% |
|  | 1:100 | 2.8 EU/ml & .58 EU/mg | 103% |
|  | 1:200 | 2.5 EU/ml & 0.52 EU/mg | 104% |

TABLE 1-continued

Endotoxin levels in large scale synthesis of therapeutic aptamers.

| Sample | Dilution | Endotoxin detected | Spike recovery |
|---|---|---|---|
| ARC127 | 1:1 | 0.19 EU/ml & 0.17 EU/mg | 51% |
| | 1:10 | 0.33 EU/ml & 0.30 EU/mg | 97% |
| | 1:100 | 0.45 EU/ml & 0.41 EU/mg | 115% |
| ARC128 | 1:1 | 0.52 EU/ml & 0.76 EU/mg | 105% |
| | 1:10 | 0.57 EU/ml & 0.82 EU/mg | 127% |
| | 1:100 | 0.43 EU/ml & 0.62 EU/mg | 136% |

Small scale syntheses of the de-fluorinated ARC-126 aptamer variants were done on Applied Biosystems' Expedite 8909 DNA (Foster City, Calif.) synthesizer using standard solid-phase phosphoramidite chemistry and vendor's recommended coupling protocols. The aptamers were cleaved and deprotected by adding 250 µL ammonium hydroxide/40% aqueous methylamine (1:1) to column support and placed in a 65° C. heating block for 30 minutes. Aptamers were dried down in a Speed Vac (Savant), then resuspended in 200 µL diH$_2$O. HPLC purification was performed on a Transgenomic WAVE HPLC (Omaha, Nebr.). The columns used for ion-exchange are the DNA-PAC (Dionex, Sunnyvale, Calif.) and Resource (Amersham Biosciences, Piscataway, N.J.). Buffer A: 25 mM sodium phosphate/25% acetonitrile; Buffer B: 25 mM sodium phosphate/400 mM sodium perchlorate/25% acetonitrile, a gradient from 0-80% B was used. Purified fractions were then pooled and dried down in a Speed Vac and resuspended in 200 µL diH$_2$O.

Example 2

Stability Studies with Fluorinated Aptamers

ARC126 and ARC127 freshly synthesized in house were compared to ARC126 and ARC127 that were synthesized by Proligo (Boulder, Colo.), and had been stored lyophilized for 2 years at −20° C. (legacy aptamers).

Figure 5A:
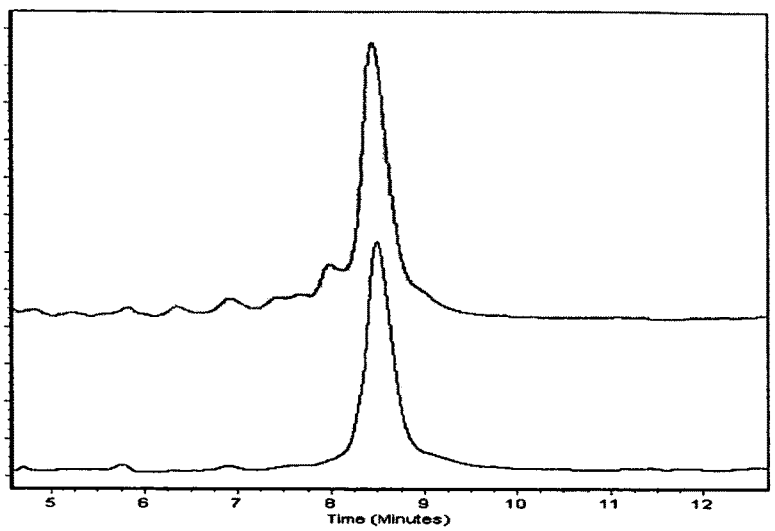
FIG. 5A is a plot of an ion-exchange HPLC analysis of ARC 127 (5'-[40K PEG]-(SEQ ID NO:1)-HEG-(SEQ ID NO:2)-HEG-(SEQ ID NO:3)-3' dT-3') freshly synthesized and stored at −20° C. for two years shows.

ARC127 synthesized in house and legacy ARC 127 were passed over an ion-exchange HPLC column for analysis. FIG. 5A is a trace of an ion-exchange HPLC analysis of freshly synthesized and legacy ARC 127 showing that after 2 years storage lyophilized at −20° C., relatively no degradation of the legacy ARC127 was detected.

Figure 5B:
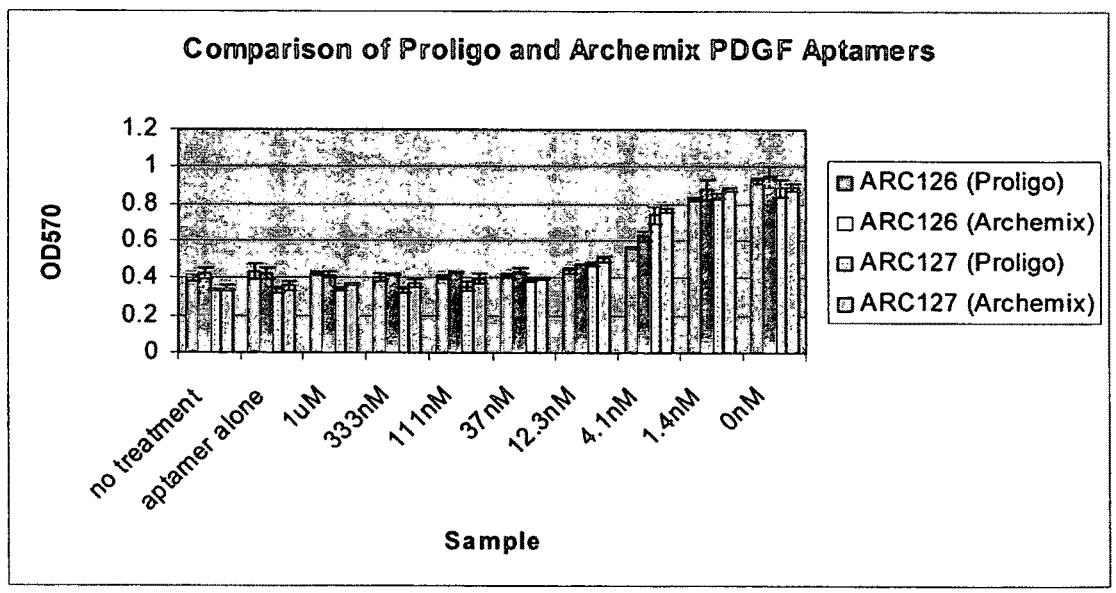
FIG. 5B is a bar-graph of 3T3 cell proliferation assay results for ARC126 (5'-(SEQ ID NO:1)-HEG-(SEQ ID NO:2)-HEG-(SEQ ID NO:3)-3' dT-3') and ARC127 newly synthesized and after storage at −20° C. for 2 years.

The legacy ARC 126 and ARC127 aptamers stored at −20° C. for two years were also tested for potency, and compared to freshly synthesized ARC126 and ARC127 synthesized in house using the 3T3 cell proliferation assay (Example 3). FIG. 5B shows cell-based assay results for potency demonstrating that even after lyophilization and storage at −20 degrees for 2 years, the legacy aptamers were just as potent as ARC126 and ARC127 newly synthesized in house.

Example 3

Composition and Sequence Optimization of ARC126 Variants

Figure 6:
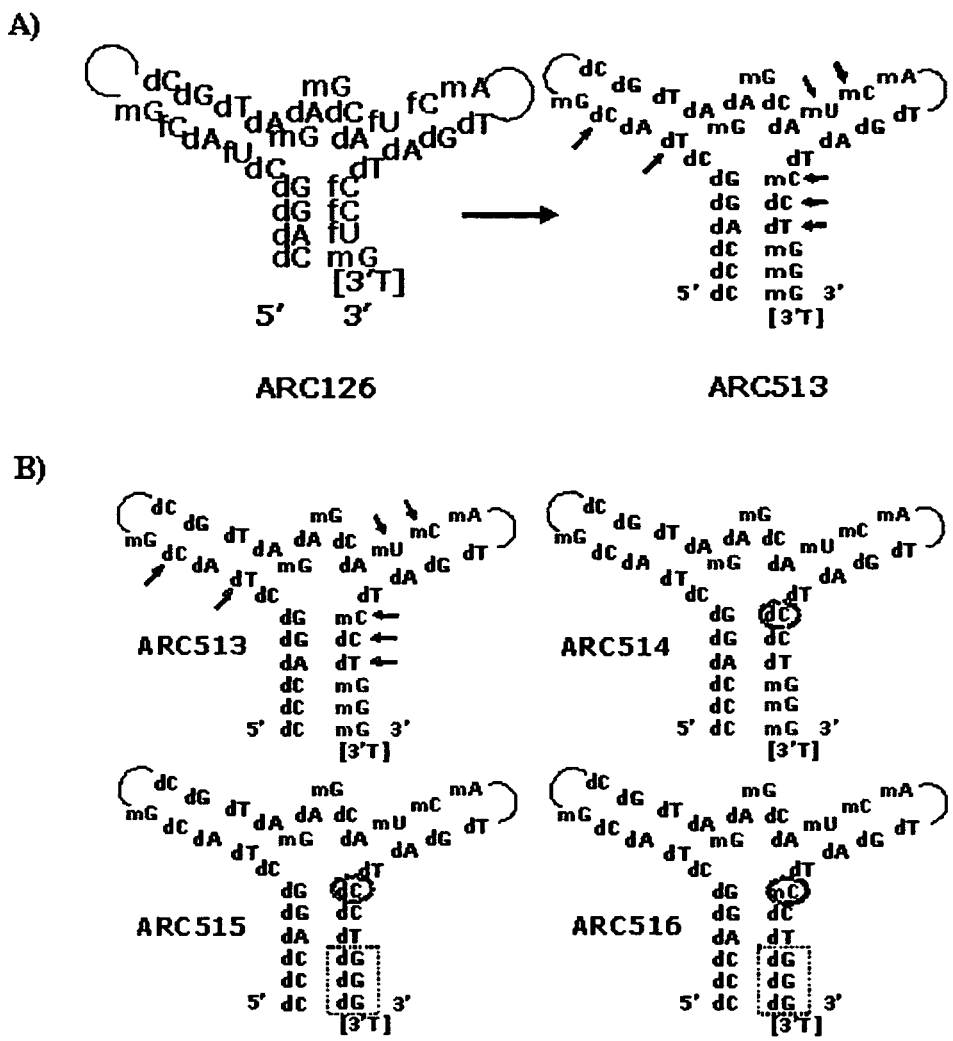
FIG. 6A is a schematic of the sequence and secondary structure of 2'-fluoro-containing PDGF aptamer composition of ARC126.
FIG. 6B is a schematic of the sequence and secondary structure of ARC126 variants ARC513 (5'-(SEQ ID NO:86)-PEG-(SEQ ID NO:57)-PEG-(SEQ ID NO:87)-3' dT-3'), ARC514 (5'-(SEQ ID NO:86)-PEG-(SEQ ID NO:57)-PEG-(SEQ ID NO:88)-3' dT-3'), ARC515 (5'-(SEQ ID NO:86)-PEG-(SEQ ID NO:57)-PEG-(SEQ ID NO:89)-3' dT-3'), and ARC516 (5'-(SEQ ID NO:86)-PEG-(SEQ ID NO:57)-PEG-(SEQ ID NO:90)-3' dT-3').

The sequence and secondary structure of the anti-PDGF aptamer designated ARC126 is shown in FIG. 6A. The sequence and secondary structure of derivatives of ARC 126 in which the nucleotides with 2'-fluoro-substituents have been replaced are shown in FIG. 6B. The loops shown at the termini of the two internal stems are polyethylene glycol-6 (PEG-6) spacers and modified nucleotides are represented by dA=deoxyadenosine; dG=deoxyguanosine; mA=2'-O-methyladenosine; dT=deoxythymidine; dC=deoxycytosine; mT=2'-O-methylthymidine; mG=2'-O-methylguanosine; mC=2'-O-methylcytosine; [3'T]=inverted deoxythymidine; fC=2'-fluorocytosine; and fU=2'-fluorouridine.

As shown in FIG. 6A, the 29-nucleotide composition of ARC126 contains seven 2'-fluoro residues (three 2'-fluorouridines and four 2'-fluorocytosines). Due to considerations including genotoxicity of breakdown products, the compositional optimization of ARC126 with the goal of modifying the sequence composition to remove all or most of 2'-fluoro residues without compromising the potency or stability of the existing molecule. One avenue for removal of 2'-fluoro residues consisted of simple substitution of all seven 2'-fluoro residues for deoxy residues. Such an all-DNA variant of ARC126, designated ARC299 (SEQ ID NO:59-PEG-SEQ ID NO:60-PEG-SEQ ID NO:61, wherein PEG=PEG-6 spacer), was synthesized and tested in in vitro biochemical binding and cell-based proliferation assays. These experiments showed that simple substitution of all 2'-fluoro residues for deoxy residues in the 29-mer composition of ARC126 induced instability in the central and upper stems, leading to significantly reduced activity/potency.

The second approach taken to effect removal of 2'-fluoro residues from ARC126 was the substitution, either singly or in blocks, of 2'-O-methyl residues for 2'-fluoro residues to ameliorate the relative base-pairing instability in the central and upper stems observed with the all-deoxy composition. A number of composition variants were synthesized, representing single point-substitutions of 2'-O-methyl or deoxy residues for 2'-fluoro residues (ARC277, 5'-(SEQ ID NO:56)-PEG-(SEQ ID NO:57)-PEG-(SEQ ID NO:58)-3T-3'), as well as block substitutions of 2'-O-methyl residues for 2'-fluoro residues (ARC337, 5'-(SEQ ID NO:59)-PEG-(SEQ ID NO:60)-PEG-(SEQ ID NO:69)-3T-3'; ARC338, 5'-(SEQ ID NO:70)-PEG-(SEQ ID NO:60)-PEG-(SEQ ID NO:71)-3T-3'; ARC339, 5'-(SEQ ID NO:65)-PEG-(SEQ ID NO:60)-PEG-(SEQ ID NO:72)-3T-3'; ARC340, 5'-(SEQ ID NO:67)-PEG-(SEQ ID NO:60)-PEG-(SEQ ID NO:69)-3T-3'; combinations of single and block substitutions (ARC341, 5'-(SEQ ID NO:99)-PEG-(SEQ ID NO:54)-PEG-(SEQ ID NO:58)-3T-3'; ARC342, 5'-(SEQ ID NO:73)-PEG-(SEQ ID NO:54)-PEG-(SEQ ID NO:58)-3T-3'; ARC344, 5'-(SEQ ID NO:74)-PEG-(SEQ ID NO:54)-PEG-(SEQ ID NO:58)-3T-3'; ARC345, 5'-(SEQ ID NO:99)-PEG-(SEQ ID NO:75)-PEG-(SEQ ID NO:58)-3T-3'; ARC346, 5'-(SEQ ID NO:99)-PEG-(SEQ ID NO:76)-PEG-(SEQ ID NO:58)-3T-3'; ARC347, 5'-(SEQ ID NO:77)-PEG-(SEQ ID NO:78)-PEG-(SEQ ID NO:79)-3T-3'; ARC362, 5'-(SEQ ID NO:99)-PEG-(SEQ ID NO:54)-PEG-(SEQ ID NO:80)-3T-3'; ARC363, 5'-(SEQ ID NO:81)-PEG-(SEQ ID NO:54)-PEG-(SEQ ID NO:82)-3T-3'; ARC364, 5'-(SEQ ID NO:67)-PEG-(SEQ ID NO:60)-PEG-(SEQ ID NO:83)-3T-3'; ARC365, 5'-(SEQ ID NO:56)-PEG-(SEQ ID NO:57)-PEG-(SEQ ID NO:83)-3T-3'; ARC366, 5'-(SEQ ID NO:84)-PEG-(SEQ ID NO:57)-PEG-(SEQ ID NO:83)-3T-3'; ARC404, 5'-(SEQ ID NO:73)-PEG-(SEQ ID NO:57)-PEG-(SEQ ID NO:58)-3T-3'; ARC405, 5'-(SEQ ID NO:74)-PEG-(SEQ ID NO:57)-PEG-(SEQ ID NO:58)-3T-3'; ARC406, 5'-(SEQ ID NO:56)-PEG-(SEQ ID NO:75)-PEG-(SEQ ID NO:58)-3T-3'; ARC407, 5'-(SEQ ID NO:56)-PEG-(SEQ ID NO:76)-PEG-(SEQ ID NO:58)-3T-3'; ARC408, 5'-(SEQ ID NO:56)-PEG-(SEQ ID NO:80)-3T-3'; ARC409, 5'-(SEQ ID NO:56)-PEG-(SEQ ID NO:57)-PEG-(SEQ ID NO:81)-3T-3'; ARC410, 5'-(SEQ ID NO:56)-PEG-(SEQ ID NO:57)-PEG-(SEQ ID NO:69)-3T-3'; ARC513 (5'-(SEQ ID NO:86)-

PEG-(SEQ ID NO:57)-PEG-(SEQ ID NO:87)-3' dT-3'), ARC514 (5'-(SEQ ID NO:86)-PEG-(SEQ ID NO:57)-PEG-(SEQ ID NO:88)-3' dT-3'), ARC515 (5'-(SEQ ID NO:86)-PEG-(SEQ ID NO:57)-PEG-(SEQ ID NO:89)-3' dT-3'), and ARC516 (5'-(SEQ ID NO:86)-PEG-(SEQ ID NO:57)-PEG-(SEQ ID NO:90)-3' dT-3'), and finally an all-2'-O-methyl composition (ARC300 (or 300B), 5'-(SEQ ID NO:62)-PEG-(SEQ ID NO:63)-PEG-(SEQ ID NO:64)-3T-3'). Other composition variants include: ARC276, 5'-(SEQ ID NO:99)-PEG-(SEQ ID NO:54)-PEG-(SEQ ID NO:55)-3T-3'; ARC335, 5'-(SEQ ID NO:65)-PEG-(SEQ ID NO:60)-PEG-(SEQ ID NO:66)-3T-3'; ARC336, 5'-(SEQ ID NO:67)-PEG-(SEQ ID NO:60)-PEG-(SEQ ID NO:68)-3T-3'; ARC343, 5'-(SEQ ID NO:70)-PEG-(SEQ ID NO:60)-PEG-(SEQ ID NO:58)-3T-3'.

Table 2 below summarizes the sequence and composition of all ARC126 variants synthesized and tested. Sequences shown are listed 5'→3' from left to right in the table. Table 2 also summarizes the composition identity and mean affinity and activity of all ARC126 variants synthesized and tested in in vitro assays (competitive binding assay and 3T3 proliferation assay) described below in Example 5. In the table, d=deoxy residue; f=2'-fluoro residue; m=2'-O-methyl residue; PEG=polyethylene glycol (PEG-6) spacer; 3T=inverted deoxythymidine.

TABLE 2

Sequence and composition of ARC126 variants.

| SEQ ID No. | ARC # | 5' modif. | Sequence (5' ≥ 3') | Activity | Activity Affinity | Activity |
|---|---|---|---|---|---|---|
| 40K PEG-SEQ ID NO: 1-HEG-SEQ ID NO: 2-127 HEG-SEQ ID NO: 3-[3T] | 127 | PEG40K- | dC dA dG dG dC fU dA fC mG -PEG- dC dG dT dA mG mG dC dA fU fC mA -PEG- dT dG dA dT fC fC fU mG -3T | +++ | 0.123 | 20.66667 |
| SEQ ID NO: 11 | 124 | | dC dA dG dG dC dT dA dC dT dA dA dC dG dG dT dA dG dC dA dG dG dG dG dA dT dC dA dC dG dA dT dG dA dT dC dT dG dT dG -3T | ++++ | 0.21 | 3.45 |
| SEQ ID NO: 99-PEG-SEQ ID NO: 5)-PEG-276 SEQ ID NO: 55-[3T] | 276 | | dC dA dG dG dC dT dA dC mG -PEG- dC dG dT dA mG dA mG dC dA dT dC mA -PEG- dT dG dA dT dC dT mG -3T | +++ | 0.23 | 18 |
| SEQ ID NO: 56-PEG-SEQ ID NO: 57-PEG-277 SEQ ID NO: 58-[3T] | 277 | | dC dA dG dG dC mU dA mC mG -PEG- dC dG dT dA mG dA mG dC dA mU mC mA -PEG- dT dG dA dT dG dT mG -3T | +++ | 0.1 | 8.666667 |
| SEQ ID NO: 59-PEG-SEQ ID NO: 60-PEG-299 SEQ ID NO: 61 | 299 | | dC dA dG dG dC dT dA mC dG -PEG- dC dG dT dA dG dA dG dC dA dT dC dA -PEG- dT dG dA dT dG -3T | – | 2.1 | 1000 |
| SEQ ID NO: 62-PEG-SEQ ID NO: 63-PEG-300 SEQ ID NO: 64-[3T] | 300 | | mC mA mG mG mC mU mA mC mG -PEG- mC mG mU mA mG mU mA mG mC mA mU mC mA -PEG- mU mG mA mU mC mG -3T | – | | 900 |
| SEQ ID NO: 65-PEG-SEQ ID NO: 60-PEG-335 SEQ ID NO: 66-[3T] | 335 | | dA dC dA dG dG dC dT dA dC dG -PEG- dC dG dT dA dG dA dG dC dA dT dC dA -PEG- dT dG dA dT dG dT -3T | ++ | 0.13 | 90 |
| SEQ ID NO: 67-PEG-SEQ ID NO: 60-PEG-336 SEQ ID NO: 68-[3T] | 336 | | dC dA dC dA dG dG dC dT dA dC dG -PEG- dC dG dT dA dG dA dG dC dA dT dC dA -PEG- dT dG dA dT dG -3dT | + | 1.6 | 196.6667 |
| SEQ ID NO: 59-PEG-SEQ ID NO: 60-PEG-337 SEQ ID NO: 69-[3T] | 337 | | dC dA dG dG dC dT dA dC dG -PEG- dC dG dT dA dG dA dG dC dA dT mC mC mU mG -3T | – | 1 | 1000 |
| SEQ ID NO: 70-PEG-SEQ ID NO: 60-PEG-338 SEQ ID NO: 71-[3T] | 338 | | mC mA mG mG dC dT dA dC dG -PEG- dC dG dT dA dG dA dG dC dA dT dC dA -PEG- dT dG dA dT dG -3T | – | 15 | 1000 |
| SEQ ID NO: 65-PEG-SEQ ID NO: 60-PEG-339 SEQ ID NO: 72-[3T] | 339 | | dA dC dA dG dG dC dT dA dC dG -PEG- dC dG dT dA dG dA dG dC dA dT mC mC mU mG -3T | – | 0.67 | 766.6667 |

TABLE 2-continued

Sequence and composition of ARC126 variants.

| SEQ ID No. | ARC # | 5' modif. | Sequence (5' ≥ 3') | Activity | Activity | Affinity | Activity |
|---|---|---|---|---|---|---|---|
| SEQ ID NO: 67-PEG-SEQ ID NO: 69-[3T] | 340 | | dC dA dA dG dT dA dC dG -PEG- dC dG dT dA dG dG dC<br>dA dT dC dA -PEG- dT dG dA dT mC mC mU mG -3T | – | 0.75 | 866.6667 |
| SEQ ID NO: 99-PEG-SEQ ID NO: 58-[3T] | 341 | | dC dA dG dG dC dT dA dC dG -PEG- dC dG dT dA mG dC<br>dA dT mC mA -PEG- dT dG dA dT mC mC mU mG -3T | – | 24 | 1000 |
| SEQ ID NO: 70-PEG-SEQ ID NO: 58-[3T] | 343 | | mC mA mG mG dC dT dA dC dG -PEG- dC dG dT dA dG dC<br>dA dT dC dA -PEG- dT dG dA dT mC mC mU mG -3T | NA | | |
| SEQ ID NO: 73-PEG-SEQ ID NO: 58-[3T] | 342 | | dC dA dG dG dC dT dA dC dG -PEG- dC dG dT dA mG dC<br>dA dT dC dA -PEG- dT dG dA mC mC mC mU mG -3T | – | 3.7 | 1000 |
| SEQ ID NO: 74-PEG-SEQ ID NO: 58-[3T] | 344 | | dC dA dG dG dC mU dA dC mG -PEG- dC dG dT dA mG dC<br>dA dT dC dA -PEG- dT dG dA dT mC mC mU mG -3T | + | 1.7 | 200 |
| SEQ ID NO: 99-PEG-SEQ ID NO: 58-[3T] | 345 | | dC dA dG dG dC dT dA dC mG -PEG- dC dG dT dA mG dC<br>dA dT mC mA -PEG- dT dG dA dT mC mC mU mG -3T | +++ | 0.52 | 13 |
| SEQ ID NO: 99-PEG-SEQ ID NO: 58-[3T] | 346 | | dC dA dG dG dC dT dA dC dG -PEG- dC dG dT dA mG dC<br>dA mU dC mA -PEG- dT dG dA dT mC mC mU mG -3T | +++ | 0.37 | 15 |
| SEQ ID NO: 77-PEG-SEQ ID NO: 79-[3T] | 347 | | dC dA dG dG dC mU dA dC mG -PEG- mC dG dA dT dA mG dC<br>dA mU mC mA -PEG- mU dG dA mU mC mC mU mG -3T | – | >1000 | 1000 |
| SEQ ID NO: 99-PEG-SEQ ID NO: 80-[3T] | 362 | | dC dA dG dG dC dT dA dC mG -PEG- dC dG dT dA mG dC<br>dA dT mC mA -PEG- dT dG dA dT dC mC mU mG -3T | + | | 315 |
| SEQ ID NO: 81-PEG-SEQ ID NO: 82-[3T] | 363 | | dC dA dC dA dG dG dC dT dA dC mG -PEG- dC dG dT dA mG dC<br>dA dT dC dA -PEG- dT dG dA dT dG -3T | ++++ | | 3.923333 |
| SEQ ID NO: 67-PEG-SEQ ID NO: 83-[3T] | 364 | | dC dA dC dA dG dG dC dT dA dC mG -PEG- dC dG dT dA dG dG dC<br>dA dT dC dA -PEG- dT dG dA dT mU mG mG -3T | – | | 1719 |
| SEQ ID NO: 56-PEG-SEQ ID NO: 83-[3T] | 365 | NH2— | dC dA dG dG dG dT dA mC mG -PEG- dC dG dT dA mG dC<br>dA mU mC mA -PEG- dT dG dA dT mC mC mU mG -3T | +++ | | 6.793333 |

TABLE 2-continued

Sequence and composition of ARC126 variants.

| SEQ ID No. | ARC # | 5' modif. | Sequence (5' ≥ 3') | Activity | Affinity | Activity |
|---|---|---|---|---|---|---|
| SEQ ID NO: 84-PEG-SEQ ID NO: 83-[3T] | 366 | 57-PEG- | dC dA dC dA dG dG dC mU dA mC mG -PEG- dC dG dT dA mG dA mG dC dA mU mC mA -PEG- dT dG dA dT dG mG mG -3T | +++ | | 5.535 |
| SEQ ID NO: 73-PEG-SEQ ID NO: 58-[3T] | 404 | 57-PEG- | dC dA dG dG dC dT dA mC mG -PEG- dC dG dT dA mG dA mG dC dA mU mC mA -PEG- dT dG dA dT mG mG -3T | ++++ | | 3.89 |
| SEQ ID NO: 74-PEG-SEQ ID NO: 58-[3T] | 405 | 57-PEG- | dC dA dG dG dC mU dA mC mG -PEG- dC dG dT dA mG dA mG dC dA mU mC mA -PEG- dT dG dA dA mG mG -3T | +++ | | 8.653333 |
| SEQ ID NO: 56-PEG-SEQ ID NO: 58-[3T] | 406 | 75-PEG- | dC dA dG dG dC mU dA mC mG -PEG- dC dG dT dA mG dA mG dC dA dT mC mA -PEG- dT dG dA dT dG mG -3T | +++ | | 17.15 |
| SEQ ID NO: 56-PEG-SEQ ID NO: 58-[3T] | 407 | 76-PEG- | dC dA dG dG dC mU dA mC mG -PEG- dC dG dT dA mG dA mG dC dA mU dC mA -PEG- dT dG dA dT mG mG -3T | +++ | | 16.36 |
| SEQ ID NO: 56-PEG-SEQ ID NO: 58-[3T] | 408 | 57-PEG- | dC dA dG dG dC mU dA mC mG -PEG- dC dG dT dA mG dA mG dC mC mU mC mA -PEG- dT dG dA dT mG mG -3T | +++ | | 28.4 |
| SEQ ID NO: 56-PEG-SEQ ID NO: 80-[3T] | 409 | 57-PEG- | dC dA dG dG dC mU dA mC mG -PEG- dC dG dT dA mG dA mG dC mC mU mC mA -PEG- dT dG dA dT dA mG mG -3T | +++ | | 7.313333 |
| SEQ ID NO: 56-PEG-SEQ ID NO: 81-[3T] | 410 | 57-PEG- | dC dA dG dG dC mU dA mC mG -PEG- dC dG dT dA mG dA mG dC mC mU mC mA -PEG- dT dG dA dT dC mG -3T | +++ | | 6.79 |
| SEQ ID NO: 56-PEG-SEQ ID NO: 69-[3T] | 513 | 57-PEG- | dC dC dA dG dA dG dC dT dA dA mC mG -PEG- dC dG dT dA mG dA mG dC dA mU mC mA -PEG- dT dG dA dT mG mG -3T | ++++ | 0.14 | 2.065 |
| SEQ ID NO: 86-PEG-SEQ ID NO: 87-[3T] | 514 | 57-PEG- | dC dC dA dC dA dG dC dT dA dA mC mG -PEG- dC dG dT dA mG dA mG dC dA mU mC mA -PEG- dT mG mG dA dA mG mG -3T | ++++ | 0.13 | 3.155 |
| SEQ ID NO: 86-PEG-SEQ ID NO: 88-[3T] | 515 | 57-PEG- | dC dC dA dC dA dG dC dT dA dA mC mG -PEG- dC dG dT dA mG dA mG dC dA mU mC mA -PEG- dT mG dG dA dA mG mG -3T | ++++ | 0.22 | 4.655 |
| SEQ ID NO: 86-PEG-SEQ ID NO: 89-[3T] | 515 | 57-PEG- | dC dC dA dC dA dG dC dT dA dA mC mG -PEG- dC dG dT dA mG dA mG dC dA dT dC mA -PEG- dT dG dA dG dA mG dC dG -3T | ++++ | 0.22 | 4.655 |
| SEQ ID NO: 86-PEG-SEQ ID NO: 90-[3T] | 516 | 57-PEG- | dC dC dA dC dA dG dC dT dA dA mC mG -PEG- dC dG dT dA mG dA mG dC dA dT mC mA -PEG- dT dG dA dG dA mG dG -3T | ++++ | 0.14 | 3.045 |

Following synthesis, these composition variants were tested in in vitro biochemical binding and cell-based proliferation assays described herein. These experiments showed a wide range of affinities in in vitro competition binding assays and a similarly wide range of activities in cell-based proliferation assays (results are described below). The composition variants that showed the highest levels of binding affinity and cell-based assay activity are exemplified by the series ARC513-516, shown in FIG. 6B. FIG. 6B shows the optimal composition variants of ARC126: ARC513 (5'-(SEQ ID NO:86)-PEG-(SEQ ID NO:57)-PEG-(SEQ ID NO:87)-3' dT-3'), ARC514 (5'-(SEQ ID NO:86)-PEG-(SEQ ID NO:57)-PEG-(SEQ ID NO:88)-3' dT-3'), ARC515 (5'-(SEQ ID NO:86)-PEG-(SEQ ID NO:57)-PEG-(SEQ ID NO:89)-3' dT-3'), and ARC516 (5'-(SEQ ID NO:86)-PEG-(SEQ ID NO:57)-PEG-(SEQ ID NO:90)-3' dT-3'). From FIG. 6B, all of the optimal composition variants are comprised of an extended stem, relative to ARC126, by two base pairs, and in the upper stems, a common set of point substitutions of 2'-O-methyl for 2'-fluoro residues as well as the pre-existing 2'-O-methyl residues from ARC126. The composition variants ARC513-516 differ only in two aspects: (1) the deoxy or 2'-fluoro identity of the three 3' terminal guanosine residues in the central stem; and (2) the deoxy or 2'-O-methyl identity of the cytosine residue at the top of the central stem on the 3' side.

Figure 7:
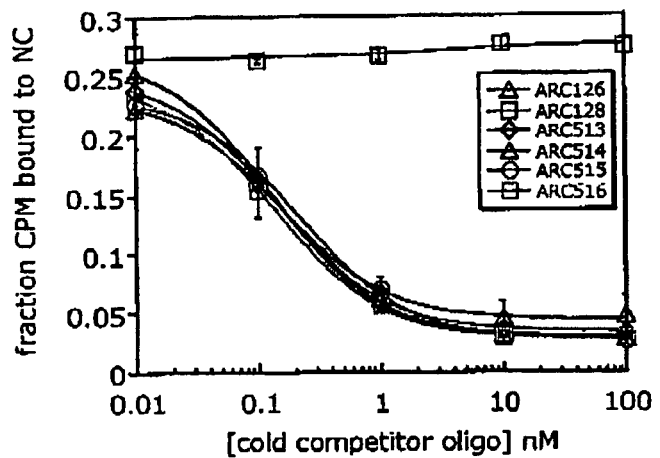
FIG. 7A is a plot of competition binding assay results for ARC126 and composition variants ARC128 (5'-(SEQ ID NO:4)-HEG-(SEQ ID NO:5)-HEG-(SEQ ID NO:6)-3'), ARC513, ARC514, ARC515, ARC516.
FIG. 7B is a plot of in vitro 3T3 cell-based proliferation assay data showing the activity of some composition variants of ARC126.
Figure 7:
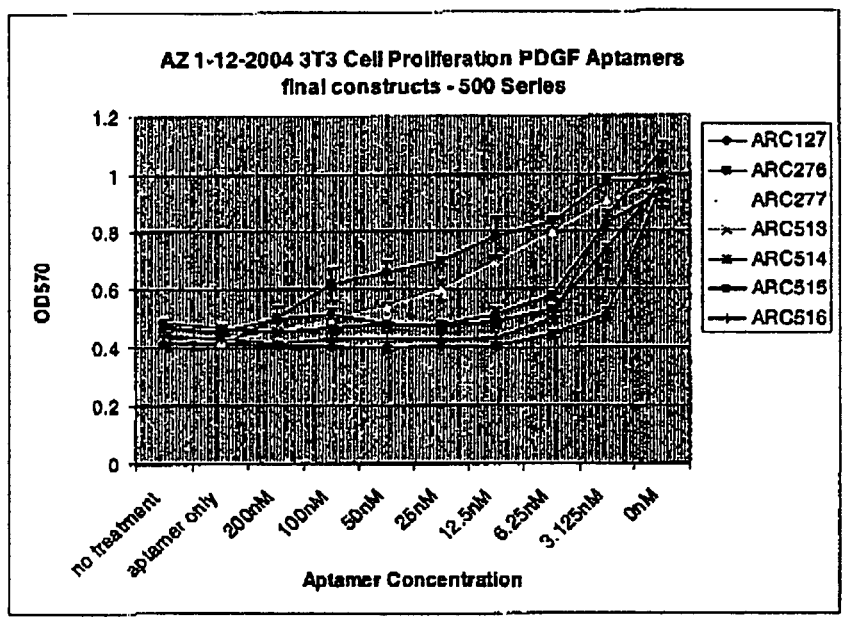

The in vitro binding affinity of the optimal composition variants for PDGF is shown in FIG. 7A. The data shown in the figure was derived from a competitive binding assay in which the indicated concentration of unlabeled, competitor aptamer was titrated in separate reactions against a fixed (<0.1 nM) amount of $^{32}$P-radiolabeled ARC126 aptamer in buffer containing a fixed amount (0.1 nM) of the aptamer's cognate target (PDGF-BB; PeproTech, Rocky Hill, N.J.). ARC126 was radiolabeled at the 5' terminus by incubation with γ-$^{32}$P-ATP (MP Biomedicals, Irvine, Calif.) and polynucleotide kinase (New England Biolabs ("NEB"), Beverly, Mass.). Binding reactions were carried out in phosphate-buffered saline (Cellgro, Herndon, Va.) containing 0.2 mg/mL bovine serum albumin (NEB) and 0.02 mg/mL tRNA (Sigma, St. Louis, Mo.). The reactions were equilibrated for a period of 15-30 minutes at room temperature, then filtered through a sandwich of nitrocellulose (Protran membrane, Perkin-Elmer, Boston, Mass.) and nylon (Hybond membrane, Amersham, Piscataway, N.J.) membranes to separate target bound aptamer from free aptamer. Subsequent auto-radiographic analysis of the filter membranes corresponding to each concentration of unlabeled aptamer revealed the extent of competitive displacement of $^{32}$P-ARC126 by unlabeled aptamer. The data is shown in FIG. 7 wherein ARC128 ((5'-(SEQ ID NO:4)-HEG-(SEQ ID NO:5)-HEG-(SEQ ID NO:6)-3')) represents a sequence-scrambled and therefore inactive variant of ARC126.

FIG. 7B shows in vitro 3T3 cell-based proliferation assay data showing the activity of some composition variants of ARC126. 3T3 cells, a rat fibroblast cell line (ATCC, Manassas, Va.), were plated 3,000 cells/well in a 96 well plate one day prior to the start of the assay in 100 ul DMEM/10% FCS. The following day, cells were washed once with straight DMEM and then 75 ul DMEM/0.8% FCS was added to each well. Then 25 ul of PDGF-BB (PeproTech, Rocky Hill, N.J.) at a final concentration of 50 ng/ml+/− ARC126 variants (6 points, final concentration 0-200 nM) were added to each well. Cells were incubated for 3 days. Following incubation 10 ul MTT (Promega, Madison, Wis.) was added to each well and incubated for an additional 1.5 hours. Media was then removed, 200 ul Isopropanol (2-propanol) was added to each well, cells were re-suspended thoroughly and absorbance at 570 nm was read on a 96 well plate reader. As shown in FIG. 7B, it is clear that (1) all composition variants shown are active; and (2) the relative activity ranking of ARC513 (5'-(SEQ ID NO:86)-PEG-(SEQ ID NO:57)-PEG-(SEQ ID NO:87)-3' dT-3'), ARC514 (5'-(SEQ ID NO:86)-PEG-(SEQ ID NO:57)-PEG-(SEQ ID NO:88)-3' dT-3'), ARC515 (5'-(SEQ ID NO:86)-PEG-(SEQ ID NO:57)-PEG-(SEQ ID NO:89)-3' dT-3'), and ARC516 (5'-(SEQ ID NO:86)-PEG-(SEQ ID NO:57)-PEG-(SEQ ID NO:90)-3' dT-3') is similar.

Optimization of In Vivo Pharmacokinetic and Biodistribution Properties.

In addition to optimization of the sequence composition of ARC126 with respect to target binding affinity and in vitro cell-based assay activity, it is desirable to optimize the in vivo pharmacokinetic (PK) half-life, $t_{1/2}$, and biodistribution properties of the optimal sequence composition(s) for the anti-PDGF aptamers described previously. This modulation of the pharmacokinetic and biodistribution properties of an aptamer composition can be accomplished (see U.S. Ser. No. 10/718,833, filed Nov. 21, 2003, and U.S. Ser. No. 60/550,790, filed Mar. 5, 2004) via conjugation of the 3' or 5' terminus, or an internal site or sites, of the molecule with a polyethylene glycol (PEG) chain or chains, i.e., PEGylation (range is ~2 kD to 100 kD, with typical PEGs having molecular weights of 2 kD, 10 kD, 20 kD, 30 kD, 40 kD, 50 kD).

Figure 8:
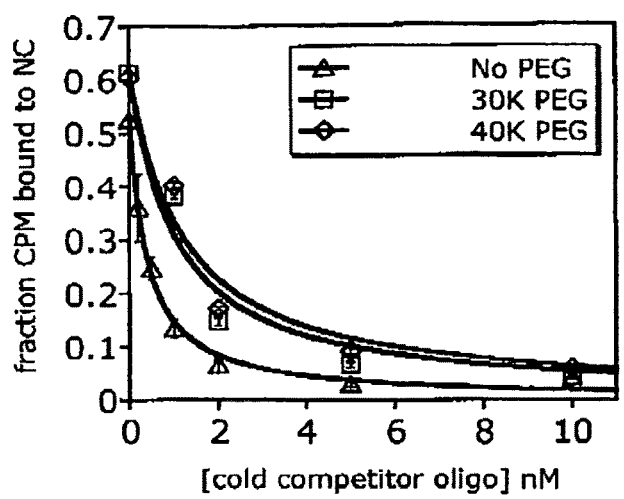
FIG. 8A is a plot of a competition binding assay for ARC126 and two variants that are 5' conjugated to 30 kD (ARC308, 5'-[30K PEG]-(SEQ ID NO:1)-HEG-(SEQ ID NO:2)-HEG-(SEQ ID NO:3)-3' dT-3') and 40 kD (ARC127) PEG groups.
FIG. 8B is a plot of in vitro 3T3 cell-based proliferation assay data for ARC126 as a function of 5' PEG group conjugation (ARC126+30 kD=ARC308, and ARC126+40 kD PEG=ARC127).
Figure 8:
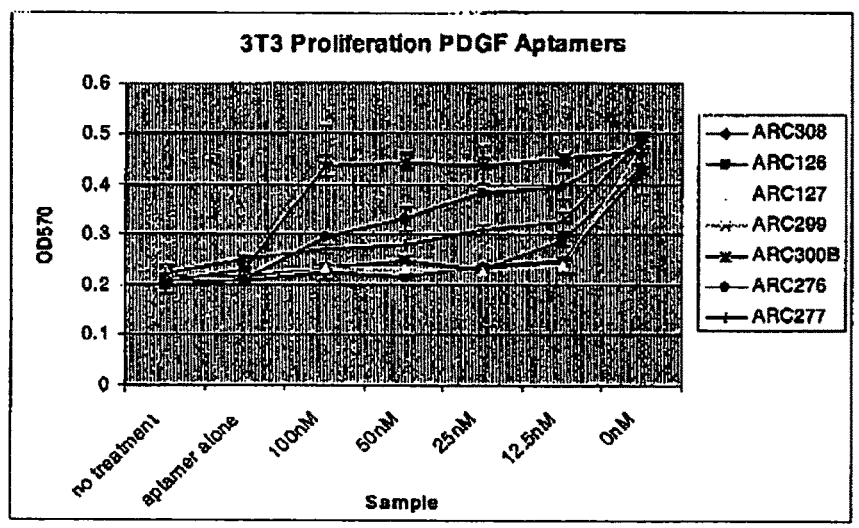

In order to establish the feasibility of using a given PEGylated aptamer sequence composition, it was necessary to confirm that the putative PEGylation does not significantly interfere with the activity of the aptamer in in vitro binding and cell-based proliferation assays. FIG. 8A shows competition binding assay curves for NH$_2$-ARC126 (5'-amine-modified ARC126, no PEG) and two variants that are 5' conjugated to 30 kD (ARC308) and 40 kD (ARC127) PEG groups, respectively. Competitive binding assays were performed and analyzed as described herein except that 3'-$^{32}$P-labeled NH$_2$-ARC126 was used rather than 5'-$^{32}$P-ARC126 (the ARC126 nucleotide sequence incorporates a reverse thymidine at the 3'-terminus, which is a substrate for the radiolabeling reaction catalyzed by polynucleotide kinase).

FIG. 8A is a plot of competition binding assay data for ARC126 and two variants that are 5' conjugated to 30 kD (ARC308) and 40 kD (ARC127) PEG groups. FIG. 8B shows in vitro 3T3 cell-based proliferation assay data for ARC126 as a function of 5' PEG group conjugation (ARC126+30 kD=ARC308, and ARC126+40 kD PEG=ARC127). The data shown in FIG. 8B demonstrate the 5' conjugation of ARC126 to 30 kD and 40 kD PEG groups appears to lead to a slight decrease in the in vitro activity of the aptamer, the effect of the presence of the PEG groups is less than two-fold relative to the unPEGylated aptamer, ARC126. The data shown in FIG. 8B also demonstrate that the 5' conjugation of ARC126 to 30 kD and 40 kD PEG groups does not significantly reduce the in vitro activity of the aptamer relative to the composition of ARC126.

Figure 9:
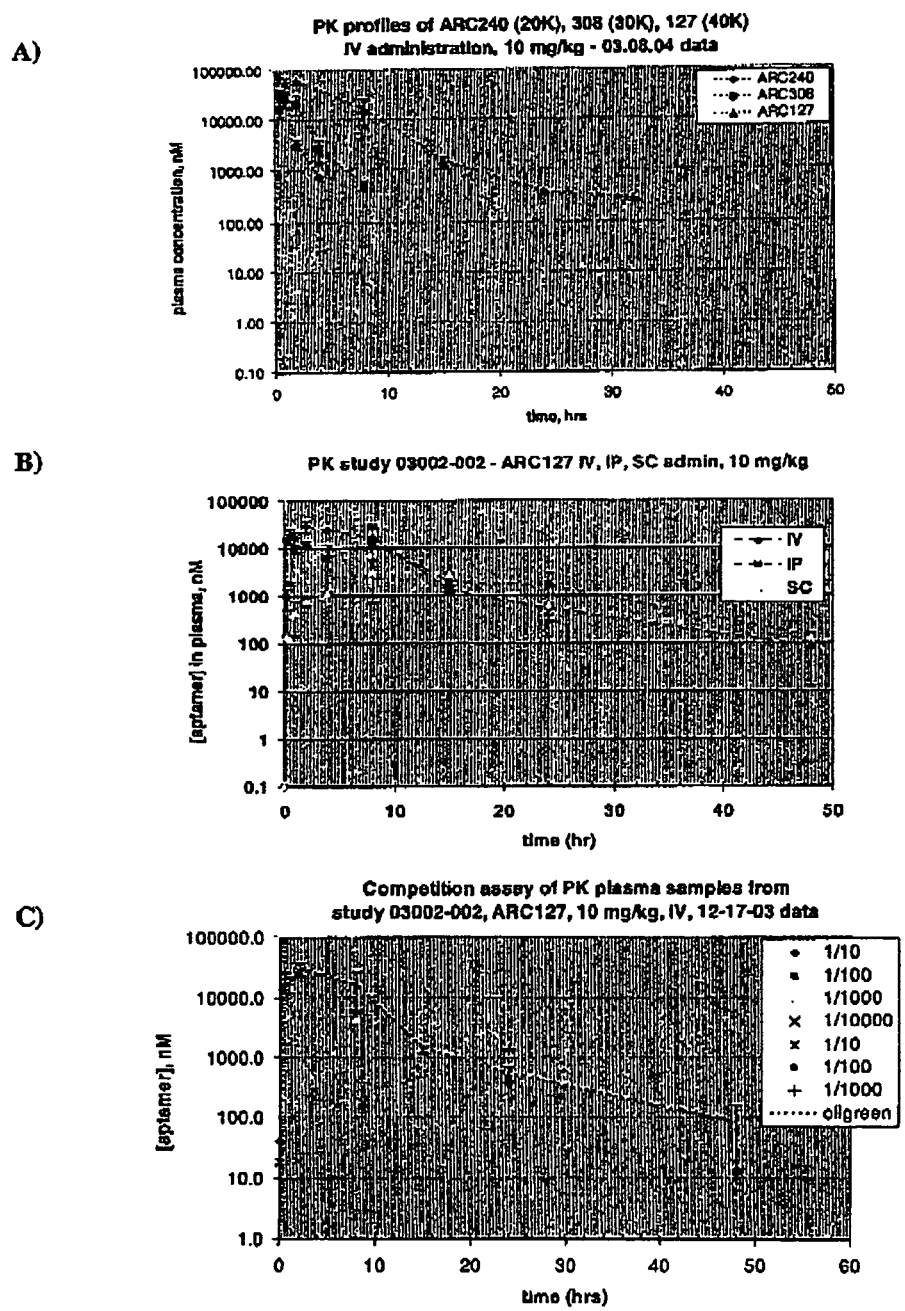
FIG. 9A is a plot of a pharmacokinetic profile of 5' conjugates of ARC126 after IV administration at 10 mg/kg in mice.
FIG. 9B is a plot of the in vivo pharmacokinetic profile of ARC127 (ARC126+40 kD PEG) after intravenous (IV), intraperitoneal (IP), and subcutaneous (SC) administration at a dose level of 10 mg/kg in mice.
FIG. 9C is a plot of the bioactivity profile of ARC126+40 kD PEG (i.e., ARC127) after intravenous (IV) administration at a dose level of 10 mg/kg in mice.

FIG. 9A shows the in vivo pharmacokinetic profile of ARC126 as a function of 5' PEG group conjugation. Studies were done in CD-1 mice as described in Example 10 (Charles River Labs, Wilmington, Mass.). From the figure, it is clear that the terminal clearance half-life, $t_{1/2}$, is strongly affected by the size of the 5' PEG group conjugated to the aptamer.

The pharmacokinetic (PK) data shown in FIG. 9A was subjected to noncompartmental analysis (NCA) using the industry-standard software package WinNonLin™ v.4.0 (Pharsight Corp., Mountain View, Calif.). Table 3 below lists the primary NCA-derived in vivo pharmacokinetic (PK) parameters for ARC126+20 kD (ARC240), +30 kD (ARC308), and +40 kD (ARC127) PEG groups after intravenous (IV) administration at 10 mg/kg in mice. The data shown in Table 3 demonstrate that the in vivo pharmacokinetic clearance half-life, $t_{1/2}$, of ARC126 is modulated ≥4-fold by changing the size of the 5' PEG group conjugated to the aptamer affected by the size of the 5' PEG group conjugated to the aptamer from 20 kD to 40 kD. FIG. 9B shows the in vivo pharmacokinetic profile of ARC127 (ARC126+40 kD PEG) after intravenous (IV), intraperitoneal (IP), and subcutaneous (SC) administration at a dose level of 10 mg/kg in mice. The pharmacokinetic (PK) data shown in FIG. 9B was subjected to noncompartmental analysis (NCA) using the industry-standard software package WinNonLin™ v.4.0 (Pharsight Corp., Mountain View, Calif.).

TABLE 3

Pharmacokinetic non-compartmental analysis of 5' conjugates of ARC126.

|  | PEG | Cmax, nM | AUC, nM · hr | $t_{max}$ (hr) | MRT (hr) | $t_{1/2}$ (hr) | $V_{ss}$ (mL/kg) |
|---|---|---|---|---|---|---|---|
| ARC240 | 20K | 34317 | 0.5 | 39277 | 1.16 | 0.94 | 0.3 |
| ARC308 | 30K | 27659 | 1.0 | 64867 | 2.14 | 1.67 | 0.3 |
| ARC127 | 40K | 60964 | 2.0 | 344356 | 5.08 | 6.84 | 0.1 |

Pharmacokinetic parameters (noncompartmental analysis) of 5' conjugates of ARC126: ARC240 = ARC126 + 20 kD PEG; ARC308 = ARC126 + 30 kD PEG; and ARC127 = ARC126 + 40 kD PEG after IV administration at 10 mg/kg in mice.

Table 4 below lists the primary NCA-derived in vivo pharmacokinetic (PK) parameters for ARC126+40 kD PEG as a function of the route of administration at 10 mg/kg in mice. The pharmacokinetic (PK) data shown in FIG. 9B was subjected to noncompartmental analysis (NCA) using the industry-standard software package WinNonLin™ v.4.0 (Pharsight Corp., Mountain View, Calif.).

TABLE 4

Pharmacokinetic profile of ARC127 (ARC126 + 40 kD PEG)

|  | Cmax, nM | $t_{max}$ (hr) | AUC (hr · nM) | MRT (hr) | $t_{1/2}$ (hr) | $V_z$ (L/kg) | bioavailability, F |
|---|---|---|---|---|---|---|---|
| IV | 29711.6 | 2 | 229686.8 | 6.573 | 8.602 | 0.053 | 1.000 |
| IP | 12756.0 | 8 | 143605.5 | 11.231 | 7.856 | 0.078 | 0.625 |
| SC | 3176.7 | 8 | 55030.91 | 16.632 | 9.176 | 0.238 | 0.240 |

Post-intravenous (IV), intraperitoneal (IP), and subcutaneous (SC) administration at a dose level of 10 mg/kg in mice.

From data shown in FIG. 9B, two primary points are clear: (1) the pharmacokinetics of ARC127 (ARC126+40 kD PEG) after intravenous (IV), intraperitoneal (IP), or subcutaneous (SC) administration at a dose level of 10 mg/kg in mice a plasma concentration of ~1 µM is present at 24 hrs post-dose; and (2) the systemic bioavailability, F, of ARC127 after intraperitoneal (IP) administration is quite high (~63%), while for subcutaneous (SC) administration the bioavailability is still high enough (~24%) to warrant consideration for clinical applications.

As a secondary test of both the plasma pharmacokinetics and the in vivo bioactivity of ARC127 (ARC126+40 kD PEG), the competition binding assay described above in reference to FIG. 7 was used to assay the same plasma samples used to generate the data shown in FIG. 9B. Serial 1:10 dilutions of plasma sample were prepared in phosphate-buffered saline (1×PBS) and mixed with a fixed concentration of $^{32}$P-ARC126, then added to human PDGF-BB. The final concentration of PDGF in each assay was 0.1 nM, and the final concentration of $^{32}$P-ARC126<0.1 nM. In this experiment, the plasma samples were analyzed by comparison with a standard curve generated with samples of known ARC127 concentrations in 1×PBS. By comparison with the reference standards, the effective concentration of active aptamer in each plasma sample could be calculated. The effective concentration of active aptamer, as calculated using the results of the competition binding assay analysis of the plasma PK samples, is shown in FIG. 9C. FIG. 9C shows the bioactivity profile of ARC126+40 kD PEG after intravenous (IV) administration at a dose level of 10 mg/kg in mice. This ex vivo analysis thus provides verification that (1) the aptamer was present and active in the plasma of the mouse model at t=48 hrs post-dose; and (2) the plasma concentrations calculated from the fluorescence-based pharmacokinetic assay are correct.

Example 4

Species Cross Reactivity of ARC126 and ARC127

Figure 10:
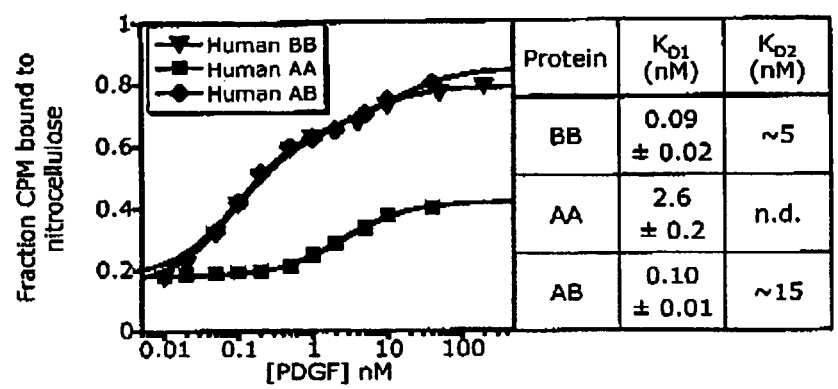
FIG. 10A is a plot of a competition binding assay showing that ARC126 binds to PDGF-BB with a $K_d$ of approximately 100 pM, and PDGF-AB with a $K_d$ of approximately 100 pM, but does not bind to PDGF-AA.
FIG. 10B is a plot of a competition binding assay showing that ARC126 binds to human, rat and mouse PDGF-BB with an equal affinity of approximately 100 pM.
Figure 10:
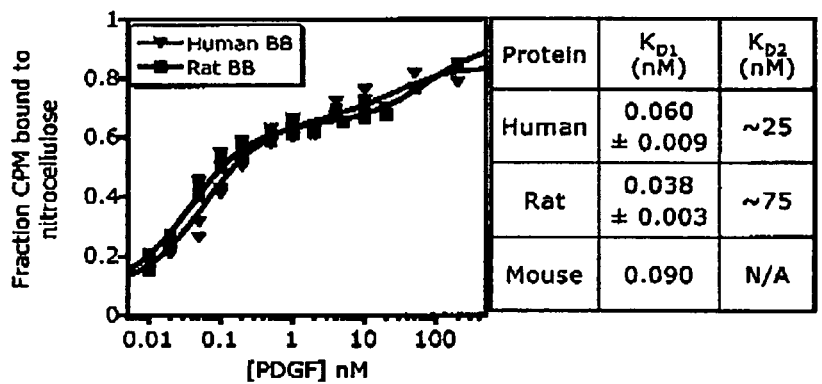

Studies were performed to determine which isoforms of PDGF ARC126 would bind to. Competition binding assays were set up using the dot blot analysis previously described, to test ARC126 for binding to human PDGF-AA, PDGF-BB and PDGF-AB (all from PeproTech, Rocky Hill, N.J.). The results of the competition binding assay show that ARC126 (SEQ ID No. 4) binds to PDGF-BB with a $K_d$ of approximately 100 pM, and PDGF-AB with a $K_d$ of approximately 100 pM, but does not bind to PDGF-AA (FIG. 10A). Next, a study was done to determine whether ARC126 cross reacted with PDGF-BB of species other than human. Competition binding assays were set up by dot blot analysis, as previously described, using human, rat, and mouse PDGF-BB (PeproTech, Rocky Hill, N.J.). The results of the competition binding assay show that ARC126 binds to human, rat and mouse PDGF-BB with equal affinity (FIG. 10B).

Example 5

3T3 Cell Proliferation Assay

Since ARC126 was shown to cross react with human, rat and mouse PDGF-BB, 3T3 cells, which are derived from a rat fibroblast cell line (ATCC, Manassas, Va.), could be used in a proliferation assay to test potency of all PDGF aptamers, including aptamers that were obtained as part of the defluorination efforts. 3T3 fibroblast cells have PDGF receptors on their cell-surface and respond to mitogen, e.g., PDGF stimulation by proliferation. The assay was performed as follows: 3T3 cells were plated 3,000 cells/well in a 96 well plate one day prior to the start of the assay in 100 ul DMEM/10% FCS. The following day, cells were washed once with straight DMEM and then 75 ul DMEM/0.8% FCS was added to each well. Then 25 ul of PDGF-BB (Pepro-Tech, Rocky Hill, N.J.) at a 50 ng/ml final concentration was added to each well+/−aptamer condition to be tested. Each plate included the following conditions in triplicate: no PDGF which corresponds to growth without mitogen (negative control), a scrambled aptamer control (ARC128) where no effect on growth rate is observed (negative control), a positive control where maximal growth is observed in the absence of PDGF aptamer, and a series of functional PDGF aptamer dilutions from which a good IC50 curve could be calculated. The functional PDGF aptamer dilutions usually consists of 6 points in 2-fold serial dilutions.

Figure 11:
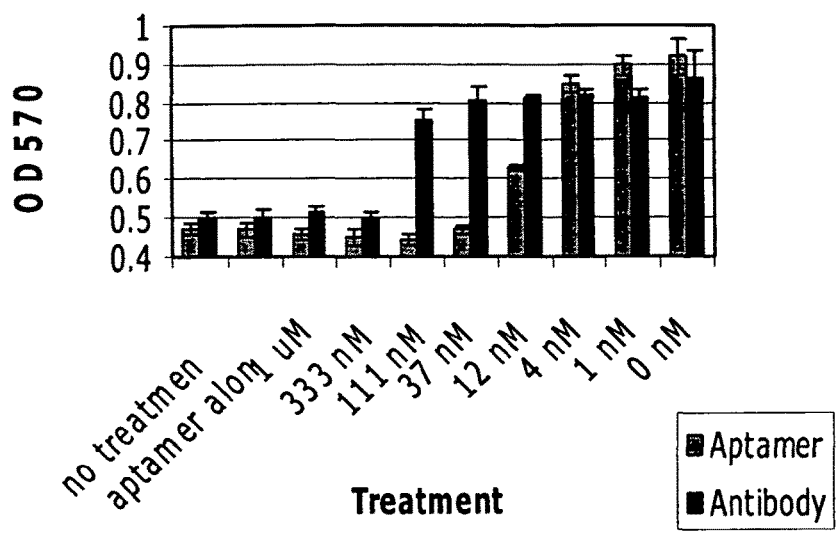
FIG. 11A is a plot of the results of a 3T3 cell proliferation assay showing that ARC127 inhibits 3T3 cell proliferation better than PDGF Neutralizing antibody.
FIG. 11B is a plot of the results of a 3T3 cell proliferation assay showing that ARC127 inhibits 3T3 cell proliferation better than known tyrosine kinase inhibitors tested.
Figure 11:
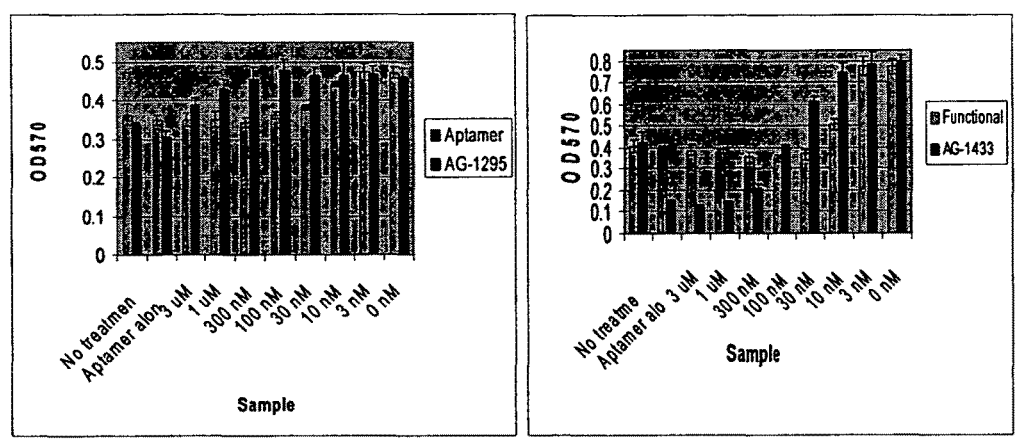

Cells were incubated for 3 days. Following incubation 10 ul MTT (Promega, Madison, Wis.) was added to each well and incubated for an additional 1.5 hours. Media was removed, 200 μl Isopropanol (2-propanol) was added to each well, cells were re-suspended thoroughly and absorbance at 570 nm was read on a 96 well plate reader. The present example depicts the potency comparison of PDGF aptamer ARC 127 to that of a PDGF neutralizing polyclonal antibody as shown in FIG. 11A (R&D Systems, Minneapolis, Minn.). The data shown in FIG. 11A demonstrate that the aptamer displays better potency than the polyclonal antibody.

The 3T3 cell proliferation assay was performed with ARC126, ARC127, ARC128 and with all the other PDGF aptamer derivatives that were obtained as described in Example 1 above. ARC126 and ARC127 routinely display $IC_{50}$ values<20 nM where scrambled control ARC128 never displays an effect of 3T3 cell proliferation. Table 5 below shows the $IC_{50}$s of ARC126 variants in 3T3 proliferation assay.

TABLE 5

IC50's of defluorinated ARC126 variants in 3T3 proliferation assay.

| ARC # | Mean IC50 |
|---|---|
| 124 | 20.67 |
| 126 | 3.40 |
| 127 | 3.45 |
| 276 | 18.00 |
| 277 | 8.67 |
| 299 | 1000.00 |
| 300 | 900.00 |
| 335 | 90.00 |
| 336 | 196.67 |
| 337 | 1000.00 |
| 338 | 1000.00 |
| 339 | 766.67 |
| 340 | 866.67 |
| 341 | 1000.00 |
| 343 | |
| 342 | 1000.00 |
| 344 | 200.00 |
| 345 | 13.00 |
| 346 | 15.00 |
| 347 | 1000.00 |
| 362 | 315.00 |
| 363 | 3.92 |
| 364 | 1719.00 |
| 365 | 6.79 |
| 366 | 5.54 |
| 404 | 3.89 |
| 405 | 8.65 |
| 406 | 17.15 |
| 407 | 16.36 |

TABLE 5-continued

IC50's of defluorinated ARC126 variants in 3T3 proliferation assay.

| ARC # | Mean IC50 |
|---|---|
| 408 | 28.40 |
| 409 | 7.31 |
| 410 | 6.79 |
| 513 | 2.07 |
| 514 | 3.16 |
| 515 | 4.66 |
| 516 | 3.05 |
| 127 | 3.45 |

The ARC 127 PDGF aptamer also blocks proliferation of 3T3 cells better than known tyrosine kinase inhibitors such as AG 1295 and AG 1433 compounds (Sigma Aldrich Biochemicals, St Louis, Mo.). The assay conditions were exactly the same as described above. ARC127 reduced the PDGF driven increase in proliferation to background levels at a concentration as low as 30 nM. Both of the AG compounds displayed much worse potencies compared to ARC127. AG-1433 seemed to have unspecific toxic effects at micromolar levels. This effect is visible starting from 300 nM where signal levels are lower than no treatment alone samples corresponding to loss of signal due to lethality of cells only in the presence of AG compound (FIG. 11B).

Example 6

3T3 Cell Viability Assay

Figure 12:
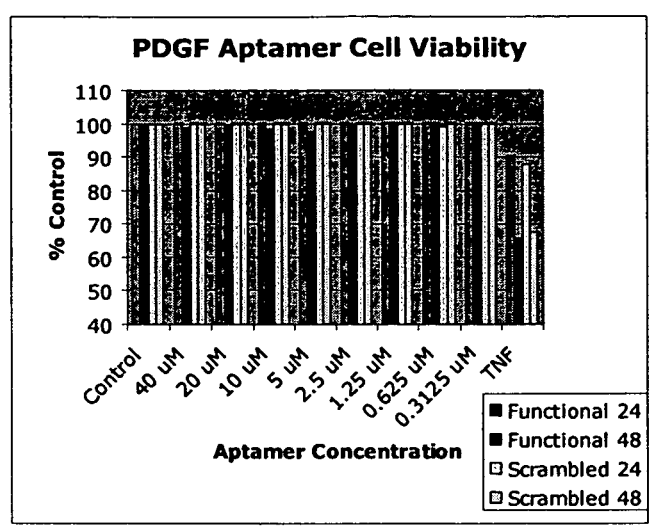
FIG. 12 is a plot of a cell viability assay results showing that ARC127 alone does not have any toxic effect on 3T3 cells.

The reduction of growth in 3T3 cells observed in the cell proliferation assay described in Example 5 upon addition of ARC126, ARC127 and other active PDGF aptamer derivatives might potentially be due to toxic effects of aptamer. To test this possibility a Calcein AM cell viability assay (Molecular Probes, Eugene, Oreg.) was performed. 3T3 cells were plated 3,000 cells/well were treated with various concentrations of PDGF aptamer up to 40 μM were tested for 24 and 48 hours. TNF alpha (100 pg/ml) was provided and used as a positive control to induce apoptosis. Following incubation cells were washed with 1×PBS. Calcein AM was prepared according to manufacturer's recommended instructions, incubated for 30 minutes and fluorescence signal intensity was determined on a 96-well plate reader. No increase in the apoptosis rate of 3T3 cells due to ARC127 was observed (FIG. 12).

Example 7

3T3 or RPE Cell Migration Assay

PDGF is a strong mitogen as well as a chemoattractant. A migration assay performed both in 24 and 96-well format was chosen as an additional functional assay to test the potency of ARC127. In the cell migration assay 80,000 cells 3T3 rat fibroblasts (ATCC, Manassas, Va.) or RPE (retinal pigmented epithelial) cells (ATCC, Manassas, Va.) were plated per well into a 24 well plate with 8 micron filters (BD Biosciences, Discovery Labware, Bedford, Mass.). 0.5 ml DMEM/0.2% FCS was added to the top chamber and 0.8 ml DMEM/0.2% FCS was added to the bottom chamber. The system was equilibrated by incubating for 4 hours at 37 degrees. Human PDGF-BB (PeproTech, Rocky Hill, N.J.) (for RPE cells) or rat PDGF-BB (PeproTech) (for 3T3 cells)

was added to the bottom chamber (0 ng/ml-100 ng/ml final concentration). The system was incubated 4 hours to 12 hours. Cells were scraped off on the top of filter with a Q-tip. The cells that migrated to the bottom of the filter were fixed with a mixture of cold 50% Methanol/50% Acetone for 3 minutes.

Following incubation filters were washed with 1×PBS and stained with Giemsa Stain (Matheson Coleman and Bell) for 1-2 hours and migration was visualized by taking pictures on a Zeiss Axiovert 200M microscope. Specifically, migration under four different conditions was visualized: (1) background migration observed in the absence of PDGF; (2) migration observed in the presence of 5 nM PDGF BB; (3) migration observed in the presence of 5 nM PDGF BB and 100 nM functional aptamer ARC127; and (4) migration observed in the presence of 5 nM of PDGF BB and 100 nM ARC128 scrambled control aptamer. The visualized migration results show that the presence of 100 nM ARC127 inhibits the effects of 5 nM PDGF-BB, shown by the migration of 3T3 or RPE cells at background levels. ARC128 scrambled control displays no activity and the migration observed at this condition is equal to the one observed with 5 nM PDGF BB alone.

Figure 13:
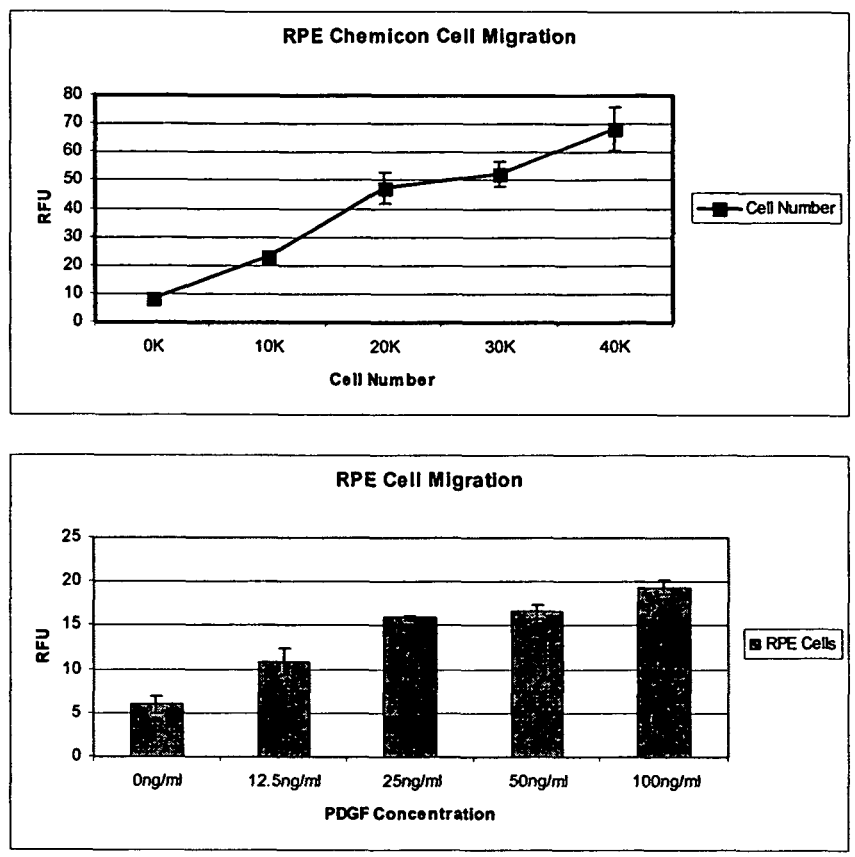
FIG. 13 is a plot of cell migration assay data performed in 96 well format using QCM Chemotaxis 96 Well Migration Assay (#ECM 510) (Chemicon, Temecula, Calif.) showing that the migration signal observed increases as a function of the number of cells plated or increasing PDGF concentration.

FIG. 13 shows the results of a cell migration experiment performed in 96 well format using QCM Chemotaxis 96 Well Migration Assay (#ECM 510) (Chemicon, Temecula, Calif.). The 96 well format allowed for a more quantitative analysis of cell migration than the 24 well format, which was more qualitative. The 96 well assay starts by bringing plates and reagents to room temperature. 150 ul of DMEM/0.2% FBS was added with or without chemoattractant to the wells of the feeder tray. 200,000 cells RPE cells in 100 ul media DMEM/0.2 FBS were added into migration chamber and incubated for 1-24 hours at 37 degrees.

Following incubation, the migration chamber plate was removed and the non-migratory cells were discarded. The number of migratory cells was quantitated according to manufacturer's recommended instructions. In brief, media from the top side was removed by flipping out the remaining cell suspension, and was placed onto a new feeder tray that contains 150 ul of pre-warmed Cell Detachment Solution. This mixture was incubated for 30 minutes at 37 degrees. CyQuant GR Dye 1:75 was diluted with 4× Lysis Buffer and 50 ul of the Lysis Buffer/Dye Solution was added to each well containing 150 ul of the solution containing migratory cells. This mixture was further incubated for 15 minutes at room temperature then transferred to a fresh 96 well plate and read at 480/520 nm absorbance on a 96 well plate reader.

The results obtained in this 96 well format cell migration experiment (FIG. 13) confirmed the cell migration experiments done in 24 well format. ARC127 reduced migration levels to background and ARC128 scrambled aptamer did not affect migration. FIG. 13 also shows that the migration observed increases linearly as a function of cell number or concentration of mitogen added.

Example 8

Clonogenic Growth Assay

U87 glioblastoma cells (ATCC) were grown in the presence or absence of mitogen as well as aptamer as shown in the panels. U87 cells were plated in DMEM/10% FBS to 50% confluency in 100 mm dishes. Cells were incubated with PDGF-BB (PeproTech)+/−ARC127 until cells appeared confluent (1-2 days). The addition of a final concentration of 50 ng/ml PDGF BB alone caused the appearance of highly connected three dimensional cell clusters. Addition of 50 ng/ml PDGF-BB plus 10 nM to 100 nM functional aptamer ARC127 reduced the occurrence of clusters to background level. The presence of aptamer had no effect on proliferation rate of the cells determined by MTT assay. Thus, the aptamer blocks cell to cell adhesion of U87 cells which are known to have PDGF driven autocrine loops. ARC127 seems to be blocking the cell surface displayed ligand binding to another cell's receptor as displayed by cell to cell adhesion.

Example 9

PDGF-Drive ELK Luciferase Assay

Figure 14:
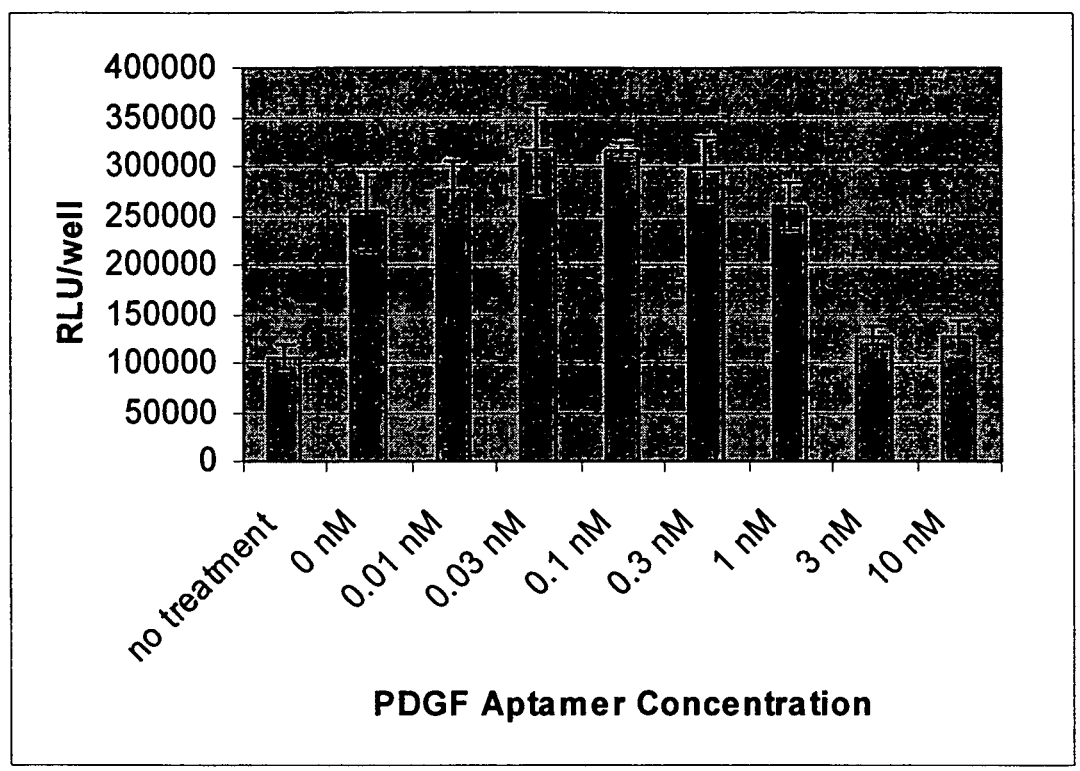
FIG. 14 is a plot of the results of a PDGF-driven Elk Luciferase assay showing the ARC127 displays an $IC_{50}$ of 2 nM.

To further prove the activity of ARC127 PDGF aptamer, a mechanistic Elk Luciferase reporter gene assays was setup. 10,000 3T3 cells/well were plated in DMEM/10% FBS in a 96 well plate. They were transfected using FuGene (Roche, Indianapolis, Ind.) at 3:1 ratio with 5 ng of ELK-1 (Stratagene, La Jolla, Calif.) and 20 ng of pFR-Luciferase plasmids (Stratagene, La Jolla, Calif.). When PDGF is added at a final concentration of 50 ng/ml to 3T3 cells, an increase in the Luciferase signal can be observed which corresponds to the effect of the mitogen on the reporter gene. Steady Glo Luciferase assay (Promega, Madison, Wis.) was used to detect luciferase. The results indicate that a concentration of ARC127 as low as 3 nM reduces the Luciferase signal to no mitogen levels. IC50 of ARC127 deduced from this analysis is <2 nM. FIG. 14.

Example 10

In Vivo Data in HT-29 and LS174T Colon Cancer Xenograft Models

In vivo efficacy studies were established to test the hypothesis that inhibition of PDGF-BB and/or its receptor with ARC127 and ARC308 (increase the efficacy of cytotoxic drugs.

Experimental Overview.

Human HT-29 or LS174T colon cancer xenotransplants were established in athymic nude mice (Nu/Nu mice, Charles River Labs, Wilmington, Mass.) by injecting mice with $1 \times 10^7$ HT29 cells (ATCC, Manassas, Va.), or $2 \times 10^6$ LS174T cells (ATCC Manassas, Va.) sub-cutaneously and allowing the tumors to grow for 5 days. On day 5, two dimensional measurements of the established tumors were taken using a digital caliper. Once tumor measurements were taken, the mice were randomized into groups such that the average tumor size was the same in each group. Once randomized, the mice were treated with irinotecan (Pfizer, NY, N.Y.) which is a cytotoxic drug shown to have efficacy against colon cancer in the presence or absence of PDGF blockade using a PDGF specific aptamer or other small molecule inhibitor, to determine if PDGF blockade increases the efficacy of the cytotoxic drug.

Materials and Methods.

Figure 15:
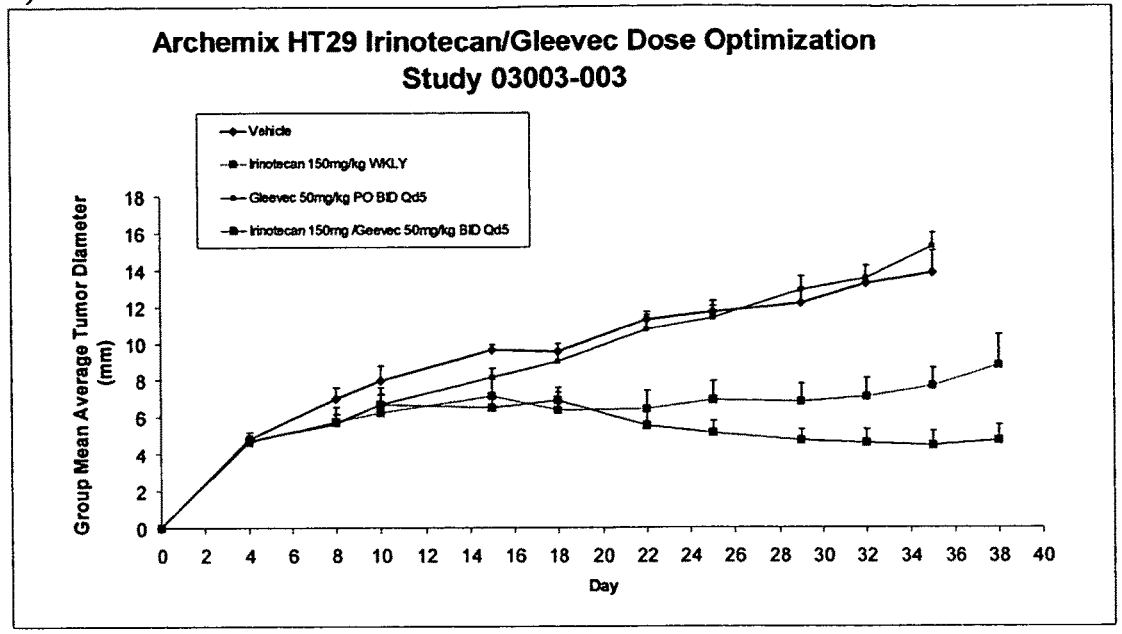
FIG. 15A is a plot of tumor diameter versus time in Nu/Nu nude mice under a GLEEVEC™/irinotecan dose optimization study in HT29 colon cancer xenograft model.
FIG. 15B is a of plot tumor diameter versus time in Nu/Nu nude mice under ARC127/irinotecan study in LS174T colon cancer xenograft model.
Figure 15:
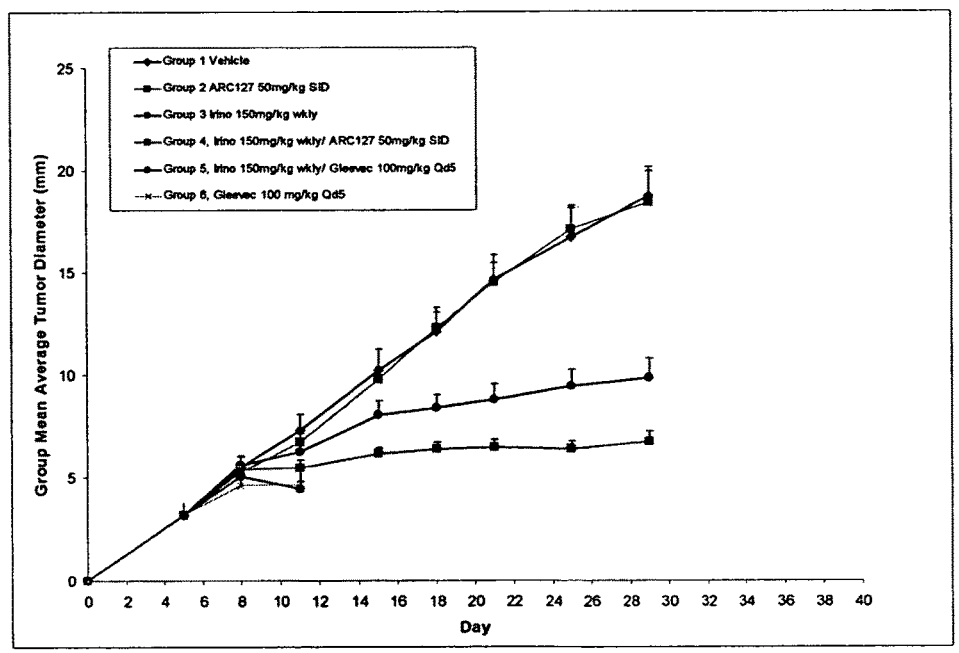

An experiment (Experiment 1) was designed to test a combination of known chemotherapeutic agents GLEEVEC™ and irinotecan in a dose optimization study in an HT29 colon cancer xenograft model. Table 6 below summarizes the experimental design of Experiment 1 using a human colon carcinoma cell line HT29 (ATCC, Manassas, Va.), with a cytotoxic drug, irinotecan (Pfizer, NY, N.Y.) administered at 150 mg/kg via intra-peritoneal injection once weekly, as well as a drug to block PDGF signaling, GLEEVEC™ (Novartis, Basel, Switzerland) dosed orally at 50 mg/kg twice daily (Monday through Friday). Though the mode of action of GLEEVEC™ is known to block the PDGF receptor function as well as other receptors for other growth factors, the effect is not necessarily PDGF specific. The results of this experiment are shown in FIG. 15A showing a plot of group mean average tumor diameter in mm as a function of time for each of the treatment regimens irinotecan 150 mg/kg weekly, GLEEVEC™ 50 mg/kg orally BID Qd5, and irinotecan 150 mg/GLEEVEC™ 50 mg/kg BID Qd5 combination therapies. These data show that GLEEVEC™ increases the efficacy of irinotecan alone in HT29 colon cancer xenotransplant model. GLEEVEC™-mediated PDGF blockade enhanced the efficacy of irinotecan treatment as demonstrated by the decreased rate of tumor growth as compared to animals treated with irinotecan alone. The results are statistically significant (two tailed students T-test).

N.Y.) was dosed once weekly at 150 mg/kg) via intraperitoneal delivery. ARC127 used to block PDGF signaling, was dosed at 50 mg/kg via intra-peritoneal delivery once daily, and GLEEVEC™ (Novartis, Basel, Switzerland) was dosed orally at 100 mg/kg once daily, Monday through Friday. ARC127 prevents PDGF-BB from binding the PDGF receptor; and has a 40K PEG attached. Table 7 below summarizes the experimental design for Experiment 2. The results from Experiment 2 are shown in FIG. 15B demonstrating that ARC127 enhanced the efficacy of irinotecan treatment as demonstrated by the decreased rate of tumor growth as compared to animals treated with irinotecan alone. The results are statistically significant (two tailed students T-test). The data clearly show that ARC127 increases the efficacy of irinotecan better than both GLEEVEC™/irinotecan combination treatment and irinotecan alone in LS174T

TABLE 6

Experiment 1 HT29 irinotecan/GLEEVEC Dose Optimization Study
Animal Study Number: 03003-005
Proposed Start Date: Jan. 13, 2003

| | | Tumor Inoculation | | | | Test Article Administration | | | | Combination Therapy Administration (PLEASE DOSE AFTER TEST ARTICLE) | | | | |
|---|---|---|---|---|---|---|---|---|---|---|---|---|---|---|
| Group | No. of Animals | Test Material | Dose | Route | Day | Test Material | Dose (mg/kg) | Route | Day | Test Material | Dose (mg/kg) | Route | Day | Day of Euthanasia |
| 1 | 10 | HT-29 | $1 \times 10^7$ cells | SC | Day 0 | Diluent | DVE | IP | Days 7, 14, 21 | NA | NA | IP | SID Days 4-21 | TBD |
| 2 | 10 | | | | | Diluent | DVE | | | ARC 127 | 50 | | | |
| 3 | 10 | | | | | Irinotecan | 150 | | | NA | NA | | | |
| 4 | 10 | | | | | Irinotecan | 50 | | | NA | NA | | | |
| 5 | 10 | | | | | Irinotecan | 150 | | | ARC 127 | 50 | | | |
| 6 | 10 | | | | | Irinotecan | 50 | | | ARC 127 | 50 | | | |
| 7 | 10 | | | | | Irinotecan | 150 | | | Gleevec | 100 | PO | | |
| 8 | 10 | | | | | Irinotecan | 50 | | | Gleevec | 100 | | | |
| 9 | | | | | | Diluent | DVE | | | Gleevec | 100 | | | |

1. Cageside and clinical observations - daily
2. Body weights - biweekly
3. Tumor measurements - biweekly starting approximately on Day 7
4. Total irinotecan needed - 450 mg (for 3 doses)
5. Total Gleevec needed - 1350 mg (for 36 doses)
6. Total PDGF aptamer needed - 675 mg (for 18 doses)
DVE = Dose Volume Equivalent of buffer
HT29 = human colon carcinoma; ATCC #HTB-38
IP = Intraperitoneal
PO = orally Another experiment (Experiment 2) was designed to test ARC127 and irinotecan in a colon cancer xenograft model using human colon carcinoma cell line LS174T (ATCC, Manassas, Va.). Cytotoxic drug, irinotecan (Pfizer, NY, colon cancer xenotransplant model. The GLEEVEC™ dosing regimen (100 mg/kg once daily, Monday through Friday, P.O.) made the animals moribund and these groups were terminated early in the experiment (FIG. 15B).

TABLE 7

ARC127/irinotecan dosing study in LS174T colon
cancer xenograft model
Experimental Design:
Animal Study Number: 03003-007
Proposed Start Date: Feb. 5, 2003

| | | Tumor Inoculation | | | | Test Article Administration | | | | Combination Therapy Administration (PLEASE DOSE AFTER TEST ARTICLE) | | | | |
|---|---|---|---|---|---|---|---|---|---|---|---|---|---|---|
| Group | No. of Animals | Test Material | Dose | Route | Day | Test Material | Dose (mg/kg) | Route | Day | Test Material | Dose (mg/kg) | Route | Day | Day of Euthanasia |
| 1 | 10 | LS174T | $2 \times 10^6$ cells | SC | Day 0 | Diluent | DVE | IP | Days 8, 15, | NA | NA | IP | SID Days | TBD |
| 2 | 10 | | | | | Diluent | DVE | | | ARC 127 | 50 | | | |

TABLE 7-continued

ARC127/irinotecan dosing study in LS174T colon
cancer xenograft model
Experimental Design:
Animal Study Number: 03003-007
Proposed Start Date: Feb. 5, 2003

| Group | No. of Animals | Tumor Inoculation Test Material | Dose | Route | Day | Test Article Administration Test Material | Dose (mg/kg) | Route | Day | Combination Therapy Administration (PLEASE DOSE AFTER TEST ARTICLE) Test Material | Dose (mg/kg) | Route | Day | Day of Euthanasia |
|---|---|---|---|---|---|---|---|---|---|---|---|---|---|---|
| 3 | 10 | | | | | Irinotecan | 150 | | 22 | NA | NA | | 4-21 | |
| 4 | 10 | | | | | Irinotecan | 150 | | | ARC 127 | 50 | | | |
| 5 | 10 | | | | | Irinotecan | 150 | | | Gleevec | 100 | PO | | |
| 6 | 10 | | | | | Diluent | DVE | | | Gleevec | 100 | | | |

Figure 16:
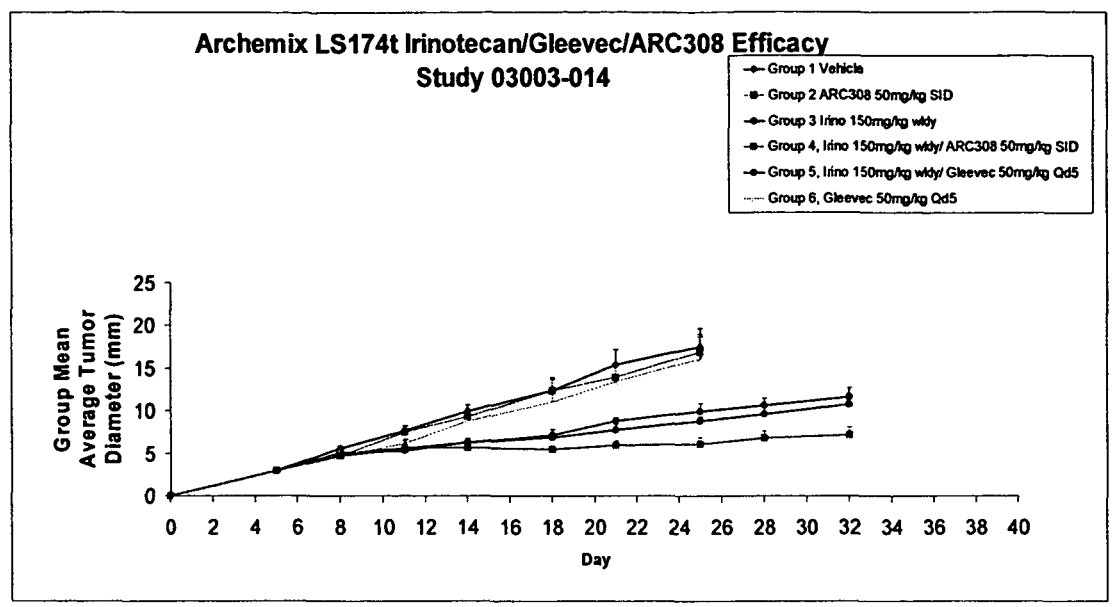
FIG. 16 is a plot of tumor diameter versus time in Nu/Nu nude mice under irinotecan, and GLEEVEC/ARC308 dosing regimens in an efficacy study in LS174T colon cancer xenotransplant model.

1. Cageside and clinical observations - daily
2. Body weights - biweekly
3. Tumor measurements - biweekly starting approximately on Day 4
4. Total irinotecan needed - 337.5 mg (for 3 doses)
5. Total Gleevec needed - 360 mg (for 18 doses)
6. Total PDGF aptamer needed - 450 mg (for 18 doses)
DVE = Dose Volume Equivalent of buffer
LS174T = human colon carcinoma
IP = Intraperitoneal A third experiment (Experiment 3) was designed to test ARC308/irinotecan and GLEEVEC™/irinotecan dosing regimens in a colon cancer xenotransplant model using human colon carcinoma cell line LS174T (ATCC). Cytotoxic drug irinotecan (Pfizer, NY, N.Y.) was dosed via intraperitoneal delivery at 150 mg/kg once weekly. ARC308 was dosed via intraperitoneal delivery at 50 mg/kg once daily, and GLEEVEC™ was dosed at 50 mg/kg once daily, Monday through Friday. ARC308 prevents PDGF-BB from binding the PDGF receptor; this molecule has a 30K PEG attached. The results from Experiment 3 are shown in FIG. 16 showing that ARC 308 enhanced the efficacy of irinotecan treatment as demonstrated by the decreased rate of tumor growth as compared to animals treated with irinotecan alone (FIG. 16). In contrast the GLEEVEC™ dosing regimen (50 mg/kg once daily, Monday through Friday, P.O) did not enhance the efficacy of Irinotecan. The results are statistically significant (two tailed students T-test). Table 8 summarizes the experimental design for Experiment 3.

TABLE 8

ARC308/irinotecan and GLEEVEC/irinotecan study
LS174T colon cancer
xenograft model.
Animal Study Number: 03003-014
Proposed Start Date: Mar. 4, 2004

| Group | No. of Animals | Tumor Inoculation Test Material | Dose | Route | Day | Test Article Administration Test Material | Dose (mg/kg) | Route | Day | Combination Therapy Administration (PLEASE DOSE AFTER TEST ARTICLE) Test Material | Dose (mg/kg) | Route | Day | Day of Euthanasia |
|---|---|---|---|---|---|---|---|---|---|---|---|---|---|---|
| 1 | 10 | LS174T | 2 × 10$^6$ | SC | Day | Diluent | DVE | IP | Days | NA | NA | IP | SID | TBD |
| 2 | 10 | cells | | | 0 | Diluent | DVE | | 8, 15, | ARC 308 | 50 | | Days | |
| 3 | 10 | | | | | Irinotecan | 150 | | 22 | NA | NA | | 5-22 | |
| 4 | 10 | | | | | Irinotecan | 150 | | | ARC 308 | 50 | | | |
| 5 | 10 | | | | | Irinotecan | 150 | | | Gleevec | 50 | PO | M-F | |
| 6 | 10 | | | | | Diluent | DVE | | | Gleevec | 50 | | | |

1. Cageside and clinical observations - daily
2. Body weights - biweekly
3. Tumor measurements - biweekly starting approximately on Day 4
4. Total irinotecan needed - 337.5 mg (for 3 doses)
5. Total Gleevec needed - 360 mg (for 18 doses)
6. Total PDGF aptamer needed - 450 mg (for 18 doses)
DVE = Dose Volume Equivalent of buffer
LS174T = human colon carcinoma
IP = Intraperitoneal In summary, these in vivo studies in HT-29 and LS174T colon cancer xenograft models confirm that PDGF blockade effected by the therapeutic aptamers of the present invention can increase the efficacy of irinotecan treatment.

Example 11

PDGF/VEGF Bi-Functional Aptamers as Oncology Therapeutics

Combination therapies have advantages over single-agent therapies in the treatment of solid tumors as shown in the colon cancer xenograft models with the aptamers of the present invention (Example 10). Similarly, aptamers that are able to bind to more than one of the targets that are implicated in solid tumor cancers are also effective in potentiating the therapeutic effects of individual therapeutic agents. Aptamers such as these can inhibit multiple proteins (or other targets) and therefore provide a single compound that acts in a manner that is substantially equivalent to a combination of compounds. Multi-functional aptamers can be engineered, e.g., from combinations of known aptamers. These multifunctional aptamers can be shown to bind to multiple targets, and can be generated either directly by solid-phase chemical synthesis, or by transcription from a corresponding DNA template. Examples of such multi-functional aptamers include aptamers capable of binding to VEGF and PDGF for cancer indications.

In order to design multifunctional aptamers from previously identified aptamers (or regions of aptamers) it is important to conjoin the individual aptamers via regions of the individual aptamer that do not make contact with the target. This can typically be accomplished by identifying regions of the secondary structure which tolerate substitution of individual nucleotides at most or all positions. If structural units are required, such as a stem, then these can be preserved in the final design. Additionally, it is important that the structural integrity of each of the individual aptamers is preserved in the final folded structure. This can most easily be achieved by predicting the secondary structures of the original aptamer sequences using an algorithm such as mfold, and then ensuring that these predicted secondary structures are preserved, according to the same algorithm, when they are part of the conjoined structure. The general mfold algorithm for determining multiple optimal and suboptimal secondary structures is described by the author of the program, Dr. Michael Zuker (Science 244, 48-52 (1989)). A description of the folding parameters used in the algorithm is presented in Jaeger, Turner, and Zuker, Proc. Natl. Acad. Sci. USA, (1989) 86, 7706-7710 (see also M. Zuker, et al., Algorithms and Thermodynamics for RNA Secondary Structure Prediction: A Practical Guide in RNA Biochemistry and Biotechnology, J. Barciszewski and B. F. C. Clark, eds., NATO ASI Series, Kluwer Academic Publishers, (1999)). Other programs that can be used according to the methods of the present invention to obtain secondary structures of nucleic acid sequences include, without limitation, RNAStructure (Mathews, D. H.; Sabina, J.; Zuker, M.; and Turner, D. H., "Expanded Sequence Dependence of Thermodynamic Parameters Improves Prediction of RNA Secondary Structure," Journal of Molecular Biology, 288, 911-940(1999), and RnaViz (Nucleic Acids Res., November 15; 25(22):4679-84 (1997).

Having determined the secondary structural motifs and units of the component aptamers, these are combined into a single oligonucleotide that folds in a manner that preserves the functionalities of each of the constituent aptamers. As a result, multifunctional aptamers are capable of binding to multiple targets, and can be generated either directly by solid phase chemical synthesis, or by transcription from a corresponding DNA template.

VEGF and PDGF Bifunctional Aptamers.

Figures 17A, 17B:
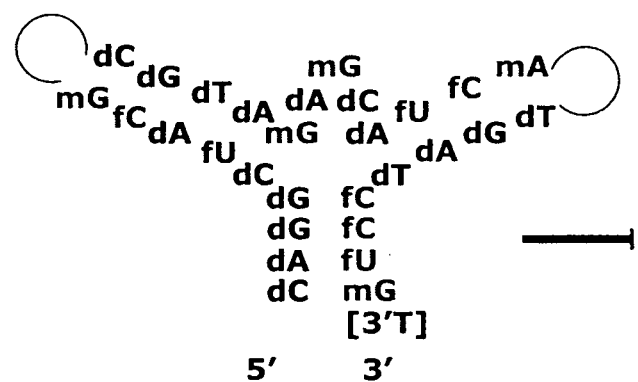
FIG. 17A is a schematic of the sequence and secondary structure of an aptamer that binds to VEGF but not PDGF-ARC245 (SEQ ID NO:7)
FIG. 17B is a schematic of the sequence and secondary structure of an aptamer that binds to PDGF but not VEGF—referred to herein as ARC126.

The methods of the present invention were applied to generate an aptamer having binding specificity to PDGF BB and to VEGF. This multi-functional aptamer was generated by joining two aptamers individually identified using SELEX-one (ARC 245, SEQ ID No. 7) which recognized VEGF but not PDGF (see FIG. 17A) and one (ARC 126, 5'-(SEQ ID NO:1)-HEG-(SEQ ID NO:2)-HEG-(SEQ ID NO:3)-3' dT-3') which recognized PDGF but not VEGF (see FIG. 17B). ARC245 (SEQ ID No. 7) is a fully 2'O methylated (2'-OMe) aptamer with binding specificity to VEGF with a $K_D$ of about 2 nM. The ARC126 used in the multivalent aptamer is entirely DNA with binding specificity to PDGF with a $K_D$ of about 100 pM.

Figure 18:
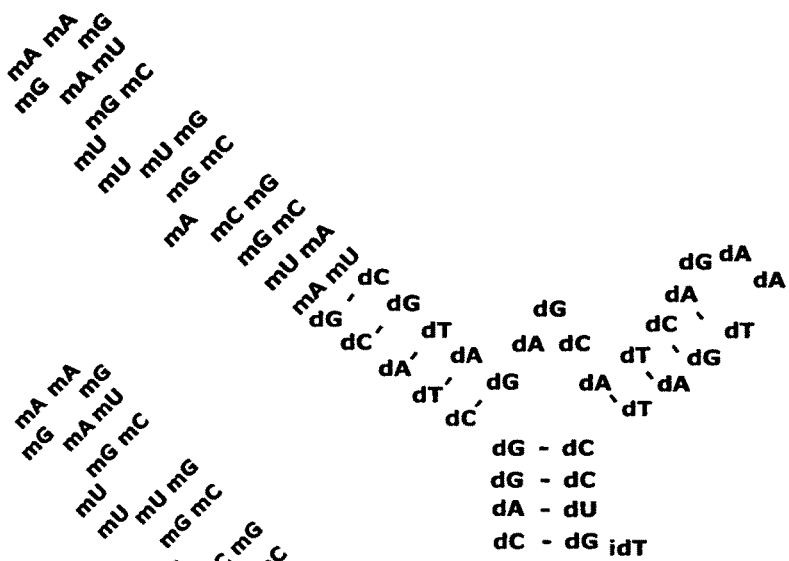
FIG. 18A is a schematic of the sequence and secondary structure of a bivalent aptamer that binds to PDGF and VEGF (sequence TK.131.012.A, SEQ ID NO:9)
FIG. 18B is a schematic of the sequence and secondary structure of a second bivalent aptamer that binds to PDGF and VEGF (sequence TK.131.012B, SEQ ID NO:10).
Figure 18:
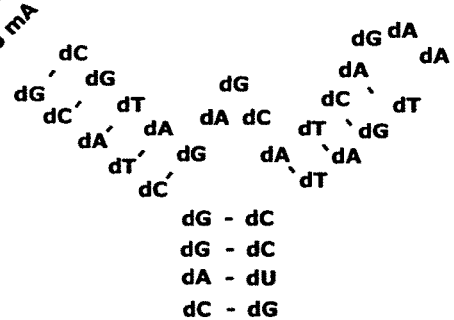

A schematic of the structure and sequence of the multivalent aptamer capable of binding to PDGF and VEGF resulting from this combination, sequence TK.131.012.A (SEQ ID No. 9), is shown in FIG. 18A. A second multivalent aptamer capable of binding to VEGF and PDGF, sequence TK.131.012.B (SEQ ID No. 10), was also formed by combining ARC245 (SEQ ID No. 7) and ARC 126. As shown in FIG. 18B, in this VEGF-PDGF multivalent aptamer the first mA-mU pair of the stem of ARC245 was removed before joining ARC245 and all deoxy-ARC126. In each case, as shown in FIG. 18, one of the ARC126 PEG linkers was removed for the addition of the VEGF specific aptamer and the other was substituted with an oligonucleotide linker having the sequence dGdAdAdA.

Figure 19:
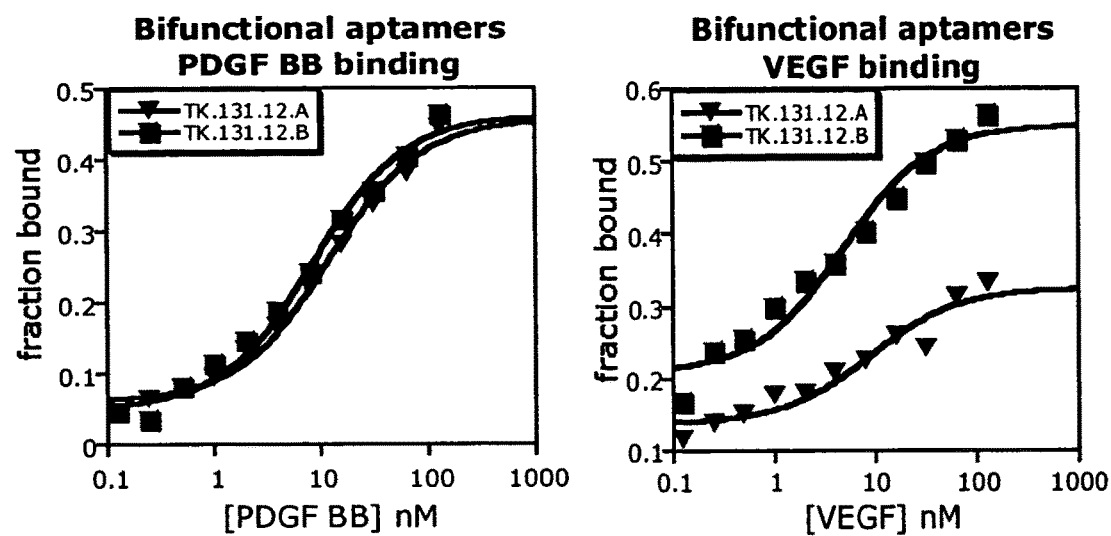
FIG. 19 is a plot of dot-blot assay binding data for the constituent aptamers and the multivalent aptamers to PDGF BB (Panel 1) and VEGF (Panel 2).

Binding data for the constituent aptamers and the multivalent aptamers were collected by dot-blot assays in which radio-labeled aptamer is incubated with protein target and then forced through a sandwich of nitrocellulose over nylon and the results shown in FIG. 19. Protein-associated radio-label is captured on the nitrocellulose membrane while the balance of the radio-label is captured on the nylon membrane. The radio-label data is collected on a phosphorimaging plate. This data is then used to calculate the binding coefficients. The multivalent aptamers TK.131.012.A (SEQ ID No. 9) and TK.131.012.B (SEQ ID No. 10) were made synthetically.

The multivalent aptamers with the sequence TK.131.012.A (SEQ ID No.9) shows a $K_D$ of about 10 nM for PDGF and about 10 nM for VEGF. The multivalent aptamer with the sequence TK.131.012.B (SEQ ID No. 10) shows a $K_D$ of about 10 nM for PDGF and about 5 nM for VEGF.

Example 12

PDGF and VEGF Aptamers Containing Immunostimulatory Motifs

To test the ability of aptamers comprising CpG motif(s) to stimulate the innate immune response, a murine CpG motif was engineered into an aptamer specific for PDGF-B. These aptamers were then used in in vitro mouse cell-based assays to confirm functionality of the CpG motifs (e.g., stimulation of the release of IL-6 and TNF-alpha). These aptamers were also used in aptamer mechanism-based biological activity assays (PDGF-B signaling through the MAPK pathway as measured by the effect of the CpG-PDGF-B-aptamer on PDGF-B activation of ERK Phosphorylation) to confirm functionality of the CpG motif comprising aptamer upon binding of the aptamer to its target, in this case PDGF-B.

To generate the aptamers disclosed herein with an embedded or appended CpG motif, the sequence of previously identified immunostimulatory oligonucleotides comprising CpG motifs ("ISS-ODN" or "ODN") or fragments thereof were engineered into ARC124, an aptamer identified through the SELEX process that binds to PDGF AB and BB with a $K_d$ of approximately 100 pm. The sequence of ARC124 is shown below.

```
ARC124                                       (SEQ ID NO.: 11)
5'
CACAGGCTACGGCACGTAGAGCATCACCATGATCCTGTG3'InvdT
```

The various ODN sequences, both full length and fragments or derivatives thereof are shown below 5'→3' from left to right (wherein an * indicates a phosphorothioate bond and 3InvdT indicates an inverted T at the 3' end). In addition to these ODN sequences or fragments thereof being engineered into PDGF aptamers, they were also used for controls in assaying the ability of these aptamers to stimulate the immune response.

```
ISS-ODN (SEQ ID NO.: 12)
T*G*A* C*T*G* T*G*A* A*C*G* T*T*C* G*A*G* A*T*G* A

ISS-ODN2 (SEQ ID NO.: 13)
T*G*A* A*C*G* T*T*C* G*A*G* A*T*

ISS-ODN3 (SEQ ID NO.: 14)
A* A*C*G* T*T*C* G*A*G* A*T*

ISS-ODN4 (SEQ ID NO. 15)
A* A*C*G* T*T*C* G*A*G

ISS-ODN5 (SEQ ID NO.: 16)
G*T*G* A*A*C* G*T*T* C*G*A* G

ODN 2006 (SEQ ID NO.: 17)
T*C*G* T*C*G* T*T*T* T*G*T* C*G*T* T*T*T* G*T*C* G*T*T

ODN 2006.2 (SEQ ID NO.: 18)
G* T*C*G* T*T*T* T*G*T* C*G*T* T*T*T* G*T

ODN 2006.3 (SEQ ID NO.: 19)
G* T*C*G* T*T*T* T*G*T* C*G*T* T
```

ISS-ODN was identified from Martin-Orzco et al., Int. Immunol., 1999. 11(7): 1111-1118. ISS-ODN 2-5 are fragments of ISS-ODN. ODN 2006 was identified from Hartmann et al., Eur. J. Immunol. 2003. 33:1633-1641. ODN 2006.2 and 2006.3 are fragments of ODN 2006.

Figure 20:
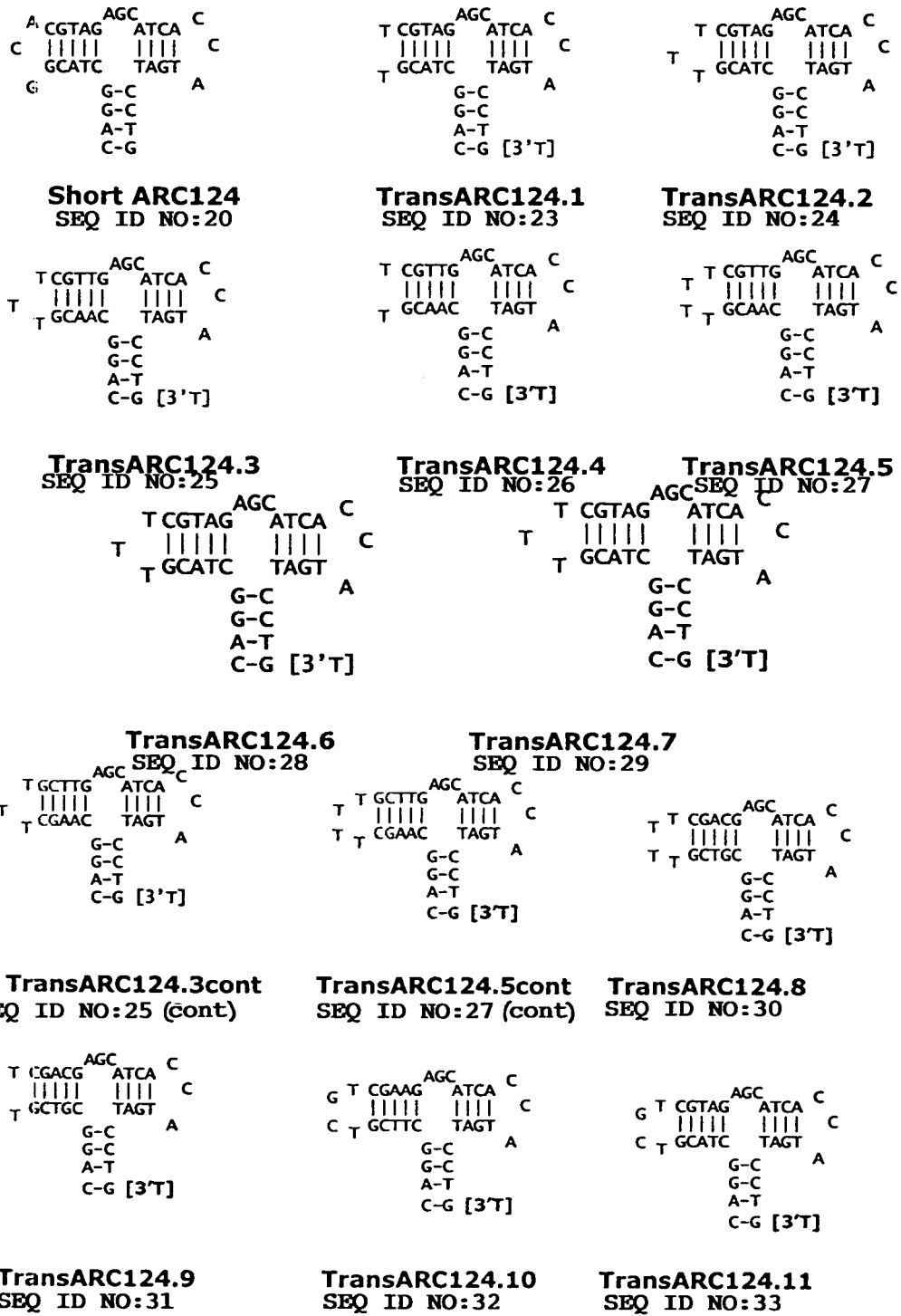
FIG. 20 is a schematic of the sequence and secondary structures (absent an indication of the phosphorothioate bonds) of PDGF aptamers having CpG islands or motifs incorporated or embedded therein.

The sequences of the PDGF aptamers comprising a CpG motif are shown below 5'→3' from left to right (wherein an * indicates a phosphorothioate bond and 3InvdT indicates an inverted T at the 3' end). A schematic of the sequence and secondary structure of these aptamers is shown in FIG. 20.

```
CpGARC124short a.k.a. shortARC124 (SEQ ID NO.: 20)
A*A*C* G*T*T* C*G*A* G* CA GGC TAC GGC ACG TAG AGC ATC ACC ATG ATC
CT*G* C/3InvdT/

LongCpGARC124 a.k.a. longARC124 (SEQ ID NO.: 21)
G*T*G* A*A*C* G*T*T* C*G*A* G* CA GGC TAC GGC ACG TAG AGC ATC ACC
ATG ATC CT*G* C/3InvdT/

FullCpGARC124 also referred to herein as fullARC124 (SEQ ID NO.: 22)
T*G*A* C*T*G* T*G*A* A*C*G* T*T*C* G*A*G* A*T*G* A* CA GGC TAC GGC
ACG TAG AGC ATC ACC ATG ATC CT*G* T*T*T* T*T*T* T TransARC124.1 (SEQ ID NO.: 23)
C*A*G*GCTAC*G*T*T*C*GTAGAGCATCACCATGATC*C*T*G*/3InvdT/

TransARC124.2 (SEQ ID NO.: 24)
C*A*G*GCTAC*G*T*T*T*C*GTAGAGCATCACCATGATC*C*T*G*/3InvdT/

TransARC124.3 (SEQ ID NO.: 25)
C*A*G*GCAAC*G*T*T*T*C*GTTGAGCATCACCATGATC*C*T*G*/3InvdT/

TransARC124.4 (SEQ ID NO.: 26)
C*A*G*GCAAC*G*T*T*C*GTTGAGCATCACCATGATC*C*T*G*/3InvdT/

TransARC124.5 (SEQ ID NO.: 27)
C*A*G*GCAAC*G*T*T*T*T*C*GTTGAGCATCACCATGATC*C*T*G*/3InvdT/
```

-continued

```
TransARC124.6 (SEQ ID NO.: 28)
C*A*G*GCTACGTTTCGTAGAGCATCACCATGATC*C*T*G*/3InvdT/

TransARC124.7 (SEQ ID NO.: 29)
C*A*GGCTACGTTTCGTAGAGCATCACCATGATCC*T*G*/3InvdT/

TransARC124.8 (SEQ ID NO.: 30)
C*A*G*GCGTCGTTTTCGACGAGCATCACCATGATC*C*T*G*/3InvdT/

TransARC124.9 (SEQ ID NO.: 31)
C*A*G*GCGTCGTCGTCGACGAGCATCACCATGATC*C*T*G*/3InvdT/

TransARC124.10 (SEQ ID NO.: 32)
C*A*G*GCTTCGTCGTCGAAGAGCATCACCATGATC*C*T*G*/3InvdT/

TransARC124.11 (SEQ ID NO.: 33)
C*A*G*GCTACGTCGTCGTAGAGCATCACCATGATC*C*T*G*/3InvdT/
```

As indicated above, ISS-ODN and ODN 2006 are phosphorothioated oligonucleotides that are reported to be immunostimulatory and their sequences are derived from the literature. Truncated versions of these oligonucleotides were designed by shortening them from both their 5' and 3' ends. The resulting constructs are ISS-ODN2 through 5 and ODN 2006.2 through 3. Each of the newly designed constructs was tested in IL-6 release assay to assess the effect on immunostimulatory ability. The shortest construct that still retained the ability to induce IL-6 release was picked for the sequence appended either to the 5' or 3' end of ARC124. Constructs that are labeled as CpGARC124short a.k.a. shortARC124, LongCpGARC124 a.k.a. longARC124, and Full-CpGARC124 a.k.a. fullARC124 correspond to constructs where ISS-ODN4 is appended to the 5'-end of ARC124. These constructs carry phosphorothioated bonds at their 5' and 3' ends in addition to inverted T at their 3'-end to assure the adequate stability in the cell-based assay but the core middle part corresponding to ARC124 is free of phosphorothioate bonds.

ARC124 at position 8-9 and 13-14 has two naturally occurring CpG islands. Constructs with the nomenclature of TransARC124.1 through TransARC124.11 correspond to constructs that made use of these two naturally occurring CpG sequences to create an immunostimulatory sequence that would maximize the CpG response based on reports in the literature that CpG motifs that are embedded in varying lengths of Ts create maximal immunostimulatory effect. Thus, the changes that were performed on ARC124 consisted of substituting the non-essential GCA bulge at position 10-12 with various T residues. The effect of varying the T bulge on the immunostimulatory effect as well as addition of phosphorothioated bonds on the stability of the construct are assessed with IL-6 release assay and phosphorylation of ERK as described herein.

For negative controls, ARC124 was engineered to remove the CpG motifs. These control sequences are shown below.

```
TransARC124.3control (CpG-Scrambled Aptamer) (SEQ ID NO.: 34)
C*A*G*GCAAG*C*T*T*T*G*CTTGAGCATCACCATGATC*C*T*G*/3InvdT/

TransARC124.5control (CpG-Scrambled Aptamer) (SEQ ID NO.: 35)
C*A*G*GCAAG*C*T*T*T*T*G*CTTGAGCATCACCATGATC*C*T*G*/3InvdT
```

The activity of PDGF aptamers containing CpG islands of the present invention were tested in cell based assays. Supernatants of J774A.1 cells (TIB cells), a mouse macrophage cell line (ATCC #TIB-67) in the presence of CpG motifs will contain more IL-6 and TNF-alpha than cells not in the presence of CpG islands. Thus, an IL-6 and TNF-alpha solid phase ELISA was used to quantify the levels of IL-6 and TNF-alpha released into the supernatants (both from R&D System, Minneapolis, Minn.) upon exposure to various oligonucleotides comprising CpG sequences. For the IL-6 ELISA, a monoclonal antibody specific for mouse IL-6 was pre-coated onto a 96 well microplate. An enzyme-linked polyclonal antibody specific for mouse IL-6 was used to detect any bound IL-6 from the cell supernatants. For the TNF-alpha ELISA, an affinity purified polyclonal antibody specific for mouse TNF-alpha was pre-coated onto a 96 well microplate. An enzyme-linked polyclonal antibody specific for mouse TNF-alpha was used to detect any bound TNF-alpha from the cell supernatants. Both ELISAs used a colorimetric readout quantified by spectrophotometry.

Figure 21:
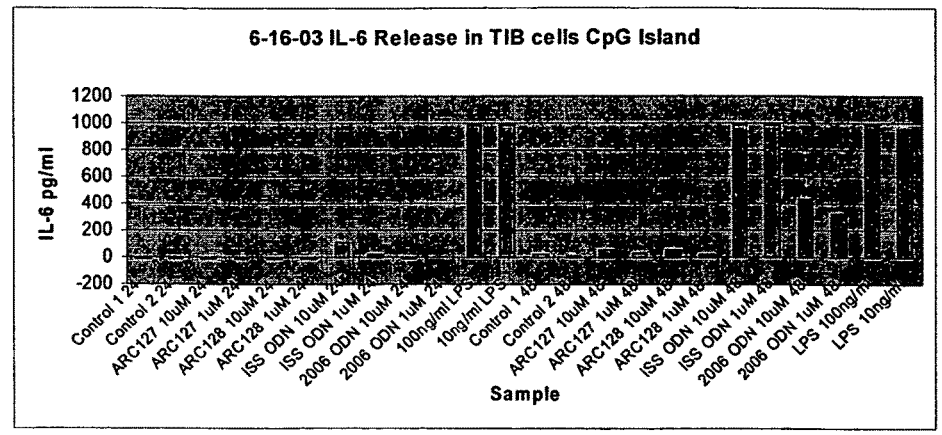
FIG. 21A is a plot of the results of an IL-6 ELISA assay measuring IL-6 release in TIB cells using known immunostimulatory ODN's as positive controls, and aptamers which contain no CpG islands as negative controls in the assay.
FIG. 21B is a plot of the results of an IL-6 ELISA assay measuring IL-6 release in TIB cells using the ISS ODN and shortened versions of the ISS ODN.
FIG. 21C is a plot of the results of an IL-6 ELISA assay measuring IL-6 release in TIB cells using PDGF aptamers in which CpG motifs have been incorporated.
FIG. 21D is a plot of the results of an IL-6 ELISA assay measuring IL-6 release in TIB cells using additional PDGF aptamers in which CpG motifs have been incorporated.
FIG. 21E is a plot of the results of an TNFa ELISA assay measuring TNFA release in TIB cells using the same PDGF aptamers as in FIG. 21D in which CpG motifs have been incorporated.
Figure 21:
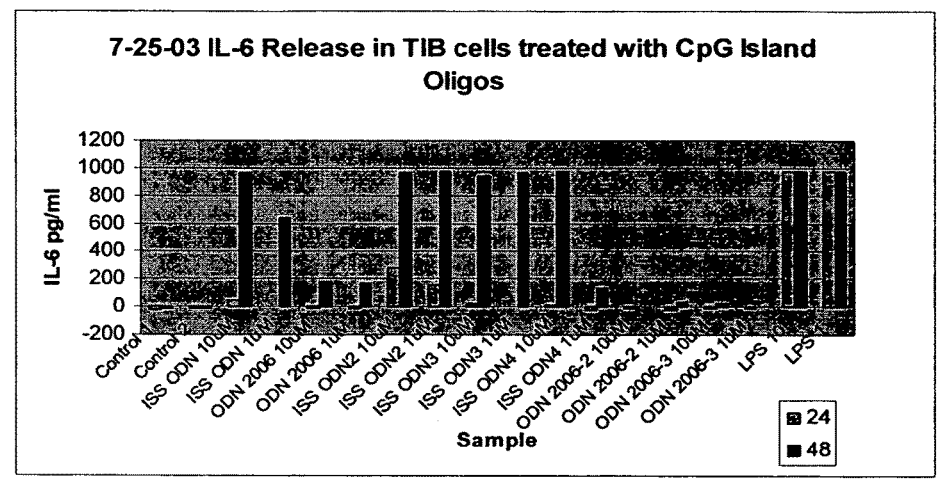
Figure 21:
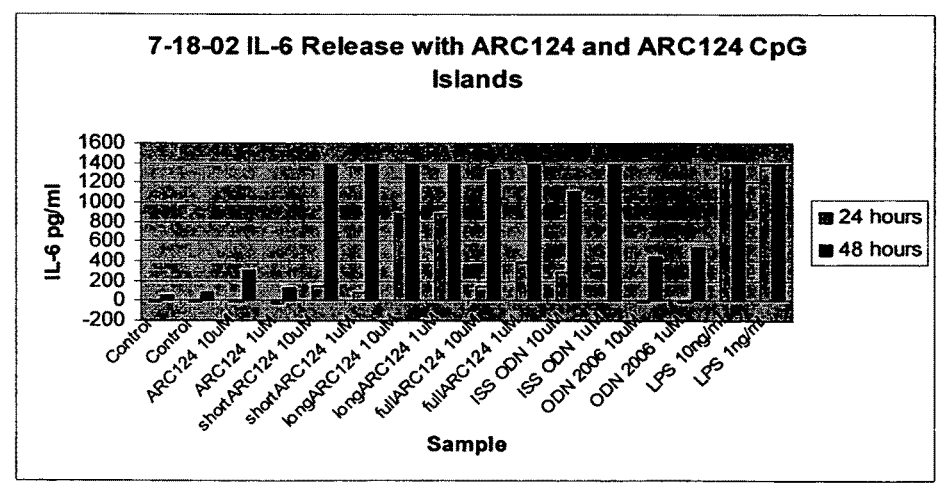
Figure 21:
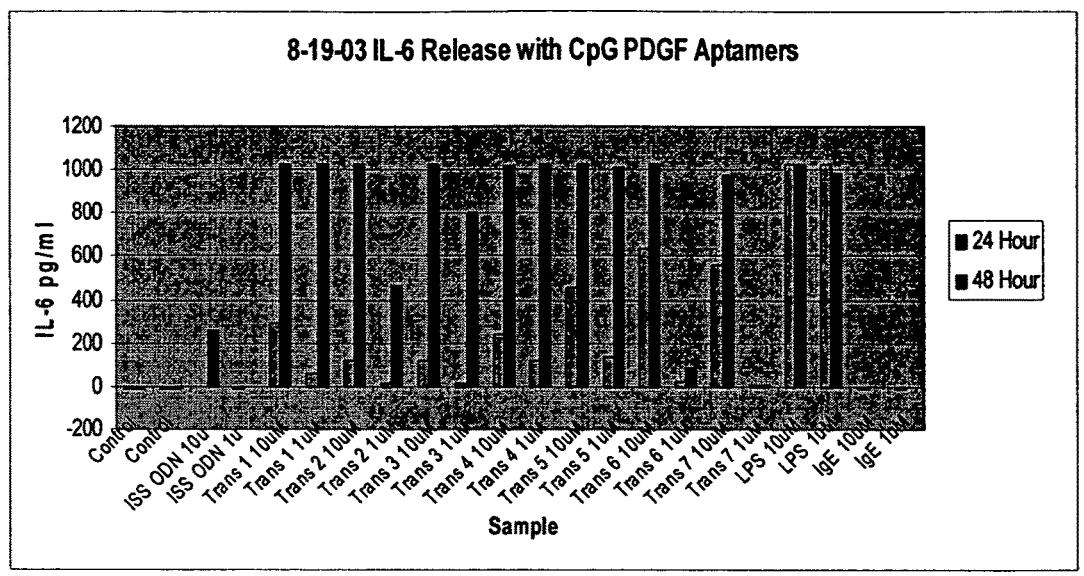
Figure 21:
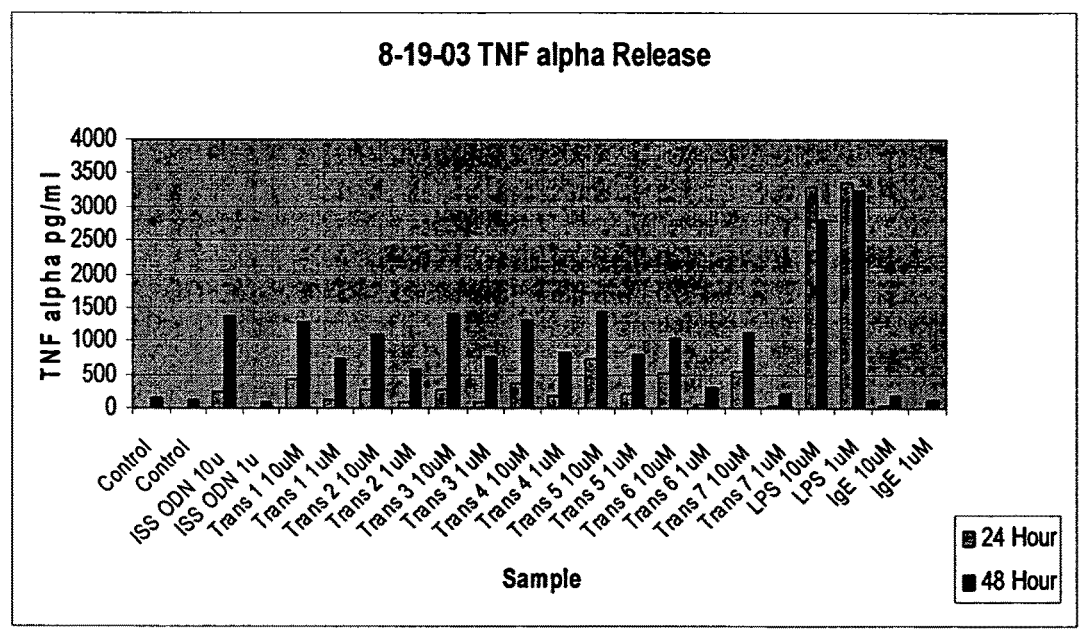

J774A.1 cells (TIB cells) were cultured in Dulbecco's Modified Eagle Media (DMEM) with 10% fetal bovine serum (FBS) (Invitrogen, Carlsbad, Calif.) at 37° C., 5% $CO_2$. 100,000 cells were plated into an appropriate number of wells on a 24 well plate one day prior to the experiment. The CpG embedded PDGF aptamers were incubated with the cells for 24 and 48 hours at 37° C., 5% COY. Final aptamer concentrations were 1 uM and 10 uM. Supernatants were collected at the indicated time-points and centrifuged for 8 minutes at 5,000 rpm at 4° C. Centrifuged supernatants were frozen at −20° C. until use in the IL-6 or TNF-alpha ELISA. Both ELISAs were used according to manufacturer's recommendations. CpG motif containing oligonucleotides previously reported to be immunostimulatory, (ISS ODN and ODN2006) and LPS (Sigma), were used as positive controls and non-CpG containing aptamers were used as negative controls. FIG. 21A shows the results of an IL-6 ELISA measuring IL-6 release in TIB cells using only the standard ODN's as positive controls, and aptamers which contain no CpG islands as negative controls in the assay. Positive and negative controls only were used in this experiment to establish whether this assay was robust enough to measure CpG induced IL-6 release. The data shown in FIG. 21B demonstrate that the ISS ODN and shortened versions of the ISS ODN induce IL-6 release in TIB cells better than ODN2006 and shortened versions thereof. FIG. 21C shows the short, long, and full versions of ARC 124 embedded with CpG motifs induces IL-6 release in TIB cells as well as the ISS ODN. The data shown in FIG.

21D shows that TransARC124.1-TransARC124.7 (SEQ ID NO:23-SEQ ID NO:29) induce IL-6 release in TIB cells. The data shown in FIG. 21E shows TransARC124.1-TransARC124.7 induce TNF-alpha release in TIB cells.

The results of the IL-6 release and TNF-alpha release assays show that when CpG motifs are incorporated into existing aptamers, in this case ARC124 (SEQ ID NO:11), the aptamer is capable of eliciting a CpG response.

Example 13

CpG Island Containing PDGF Aptamers in ERK Phosphorylation Assay

ERK phosphorylation was used to test whether ARC124 (SEQ ID NO:11) retained its functionality after the incorporation of CpG motifs into the aptamer sequence. One hundred and fifty thousand 3T3 cells (a mouse fibroblast cell line which contains PDGF-R) were plated into an appropriate number of wells on a 12 well plate one day prior to the experiment and serum starved in 0.5% FBS overnight. Cells were treated with 19 ng/ml PDGF-BB (R&D Systems, Minneapolis, Minn.) in the presence or absence of CpG-island containing PDGF aptamers for 30 minutes. Cells were collected and lysed with lysis buffer containing 10 mM Tris pH 7.5, 100 mM NaCl, 0.125% NP-40, 0.875% Brij 97, 1.5 mM sodium vanadate, and 1 mini-EDTA free protease inhibitor tablet. Protein concentration in cell lysates was determined using BIO-RAD protein assay reagent according to manufacturer's recommendations (Bio-Rad, Hercules, Calif.). Lysates were prepared by adding NuPage LDS Sample Buffer 4× with 0.1M DTT to a final concentration of 1× (Invitrogen, Carlsbad, Calif.) and incubated at 70° C. for 7 minutes. Forty micrograms of total protein was loaded into each well of a NuPage 10% Bis-Tris gel (Invitrogen, Carlsbad, Calif.). The gel was run at 100 mAmp for 1 hour. Gel was then transferred to a HyBond ECL nitrocellulose membrane (Amersham, Piscataway, N.J.) at 250 mAmp for 3 hours. After transfer, the nitrocellulose was blocked with 5% BSA (Sigma, St. Louis, Mo.) in PBS for one hour at room temperature. The nitrocellulose membrane was incubated with a p44/42 MAP Kinase antibody overnight at 4° C. (Cell Signaling Technology, Beverly, Mass.). The nitrocellulose membrane was washed 3× with PBS containing 1% Tween 20 and then incubated with an anti-rabbit IgG, HRP-conjugated antibody for 1 hour (Amersham, Piscataway, N.J.). After the one hour incubation, the nitrocellulose membrane was washed 3× with PBS containing Tween-20. Membrane was developed using an ECL+Western Blotting Detection System according to manufacturer's recommendations (Amersham, Piscataway, N.J.) and scanned using a STORM 860 (Amersham). 3T3 cells in the presence of PDGF-BB without aptamer was used as a positive control.

The results show that shortARC124 and longARC124, both PDGF aptamers carrying known CpG motifs, are still functionally active and can block phosphorylation of ERK upon binding to PDGF.

Collectively, the data show that when CpG motifs are incorporated into existing aptamers, the aptamer is capable of eliciting a CpG response and still maintain the ability to block non-CpG target (e.g., PDGF) driven effects (e.g., ERK-MAPK phosphorylation) with the same potency as native aptamers.

Example 14

PDGF-AA Selection

PDGF-AA Selection Summary

One selection for the short form of PDGF-AA (Roche Biomedical) was completed using a 2-fluoro pyrimidine containing pool. Round 1 of the selection began with incubation of $2 \times 10^{14}$ molecules of 2° F. pyrimidine modified ARC 212 pool (5' GGGAAAAGCGAAUCAUACA-CAAGA-N40-GCUCCGCCAGAGACCAACCGAGAA 3') (SEQ ID NO:91), including a spike of $\alpha^{32}$P ATP body labeled pool, with 50 pmoles of PDGF-AA protein in a final volume of 100 µL for 1 hr at room temperature. The selection was performed in 1×SHMCK buffer, pH 7.4 (20 mM Hepes pH 7.4, 120 mM NaCl, 5 mM KCl, 1 mM MgCl$_2$, 1 mM CaCl$_2$). RNA:PDGF-AA complexes and free RNA molecules were separated using 0.45 um nitrocellulose spin columns from Schleicher & Schuell (Keene, N.H.). The column was pre-washed with 1 ml 1×SHMCK, and then the RNA:protein-containing solution was added to the column and spun in a centrifuge at 1500 g for 2 min. Buffer washes were performed to remove nonspecific binders from the filters (Round 1, 2×500 µL 1×SHMCK; in later rounds, more stringent washes (increased number of washes and volume) were used to enrich for specific binders, then the RNA:protein complexes attached to the filters were eluted with 2×200 ul washes (2×100 µL washes in later rounds) of elution buffer (7M urea, 100 mM sodium acetate, 3 mM EDTA, pre-heated to 95° C.). The eluted RNA was phenol:chloroform extracted, then precipitated (40 µg glycogen, 1 volume isopropanol). The RNA was reverse transcribed with the ThermoScript RT-PCR™ system according to their instructions, using the primers KMT.108.38.C (5' TAATAC-GACTCACTATAGGGAAAAGCGAATCATACACAAGA 3') (SEQ ID NO:92) and KMT.108.38.D (5' TTCTCGGT-TGGTCTCTGGCGGAGC 3') (SEQ ID NO:93), followed by amplification by PCR (20 mM Tris pH 8.4, 50 mM KCl, 2 mM MgCl$_2$, 0.5 µM KMT.108.38.C, 0.5 µM KMT.108.38.D, 0.5 mM each dNTP, 0.05 units/µL Taq polymerase (New England Biolabs)). The PCR template was purified using the QIAquick PCR purification kit (Qiagen). Templates were transcribed using $\alpha^{32}$P ATP body labeling overnight at 37° C. (4% PEG-8000, 40 mM Tris pH 8.0, 12 mM MgCl$_2$, 1 mM spermidine, 0.002% Triton x-100, 3 mM 2'OH purines, 3 mM 2° F. pyrimidines, 25 mM DTT, inorganic pyrophosphatase, T7 Y639F single mutant RNA polymerase, 5 uCi $\alpha^{32}$P ATP). The reactions were desalted using Bio Spin columns (Bio-Rad) according to the manufacturer's instructions.

Subsequent rounds were repeated using the same method as for round 1, but with the addition of a negative selection step. Prior to incubation with protein target, the pool RNA was passed through 0.45 micron nitrocellulose to remove filter binding sequences, then the filtrate was carried on into the positive selection step. In alternating rounds, the pool RNA was gel purified. Transcription reactions were quenched with 50 mM EDTA and ethanol precipitated then purified on a 1.5 mm denaturing polyacrylamide gels (8 M urea, 10% acrylamide; 19:1 acrylamide:bisacrylamide). Pool RNA was removed from the gel by electroelution in an Elutrap® apparatus (Schleicher and Schuell, Keene, N.H.) at 225V for 1 hour in 1×TBE (90 mM Tris, 90 mM boric acid, 0.2 mM EDTA). The eluted material was precipitated by the addition of 300 mM sodium acetate and 2.5 volumes of ethanol.

The RNA remained in excess of the protein throughout the selection (~1 µM RNA). The protein concentration was 500 nM for the first 4 rounds, and then was dropped gradually over the successive rounds. Competitor tRNA was added to the binding reactions at 0.1 mg/mL starting at Round 2. A total of 11 rounds were completed, with binding assays performed at select rounds. Table 9 contains the selection details including pool RNA concentration, protein concentration, and tRNA concentration used for each round. Elution values (ratio of CPM values of protein-bound RNA versus total RNA flowing through the filter column) along with binding assays were used to monitor selection progress.

TABLE 9

Conditions used for PDGF-AA (human short form) selection sfh-PDGFAA

| Round # | RNA pool conc (uM) | protein type | protein conc (uM) | tRNA conc (mg/mL) | neg | % elution | PCR cycle # |
|---|---|---|---|---|---|---|---|
| 1 | 3.3 | sfhPDGFAA | 0.5 | 0 | none | 0.92 | 8 |
| 2 | ~1 | sfhPDGFAA | 0.5 | 0.1 | NC | 0.24 | 15 |
| 3 | ~1 | sfhPDGFAA | 0.5 | 0.1 | NC | 0.46 | 12 |
| 4 | ~1 | sfhPDGFAA | 0.5 | 0.1 | NC | 0.1 | 15 |
| 5 | 1 | sfhPDGFAA | 0.4 | 0.1 | NC | 1.39 | 10 |
| 6 | ~1 | sfhPDGFAA | 0.4 | 0.1 | NC | 0.5 | 8 |
| 7 | 1 | sfhPDGFAA | 0.3 | 0.1 | NC | 1.23 | 8 |
| 8 | ~1 | sfhPDGFAA | 0.3 | 0.1 | NC | 0.44 | 10 |
| 9 | 1 | sfhPDGFAA | 0.3 | 0.1 | NC | 5.05 | 8 |
| 10 | ~1 | sfhPDGFAA | 0.2 | 0.1 | NC | 0.83 | 10 |
| 11 | 1 | sfhPDGFAA | 0.2 | 0.1 | NC | 4.32 | 7 |

Protein Binding Analysis

Figure 23A:
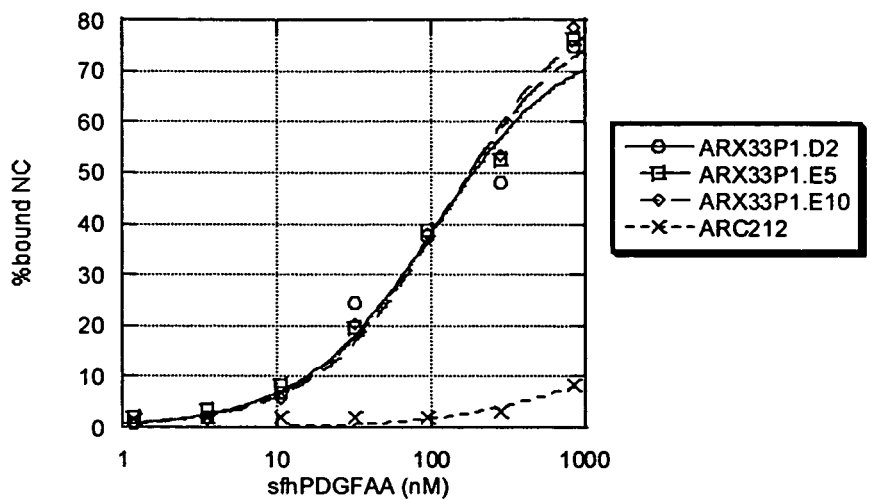
FIGS. 23A-23B are graphs depicting the dot blot binding analysis for clone RNA transcripts.
Figure 23B:
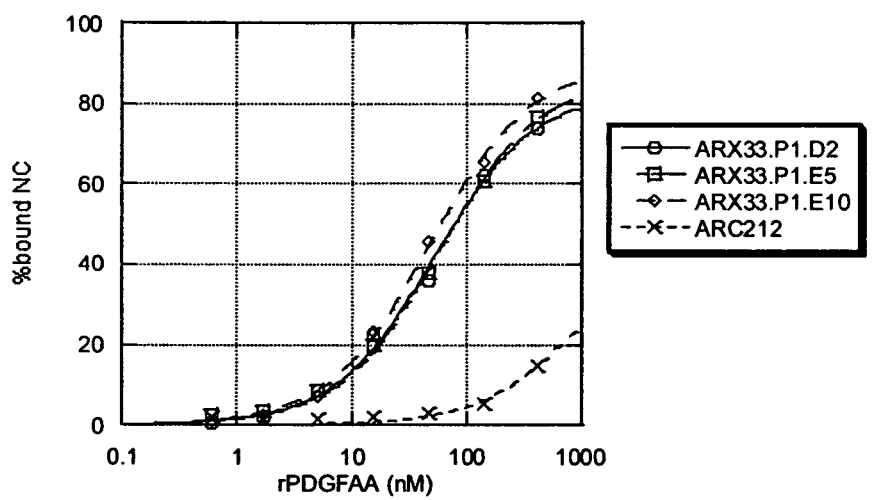

Dot blot binding assays were performed throughout the selection to monitor the protein binding affinity of the pool. Trace $^{32}$P-labeled RNA was combined with PDGF-AA and incubated at room temperature for 30 min in 1×SHMCK plus 0.1 mg/ml tRNA for a final volume of 20 µl. The reaction was added to a dot blot apparatus (Schleicher and Schuell Minifold-1 Dot Blot, Acrylic), assembled (from top to bottom) with nitrocellulose, nylon, and gel blot membranes. RNA that is bound to protein is captured on the nitrocellulose filter, whereas the non-protein bound RNA is captured on the nylon filter. When a significant positive ratio of binding of RNA in the presence of PDGF-AA versus in the absence of PDGF-AA was seen, the pool was cloned using the TOPO TA cloning kit (Invitrogen, Carlsbad, Calif.) according to the manufacturer's instructions. The Round 10 pool template was cloned, and 17 sequences were obtained. Only five different sequences were seen, with two major families and one unique sequence (not of the two families). For $K_d$ determination, the clone RNA transcripts were 5'end labeled with $\gamma$-$^{32}$P ATP. $K_d$ values were determined using the dot blot assay and fitting an equation describing a 1:1 RNA:protein complex to the resulting data (Kaleidagraph, FIGS. 23A and 23B). Results of protein binding characterization are tabulated in Table 10. Clones with high affinity to PDGF-AA were prepped and screened for functionality in cell-based assays.

TABLE 10

Clone binding activity*

R10

PDGF-AA Clones

| # | Clone Name | PDGF-AA (human short form) Kd (nM) | PDGF-AA (rat) Kd (nM) |
|---|---|---|---|
| 1 | ARX33P1.D1 | N.B. | N.B. |
| 2 | ARX33P1.D2 | 104.5 | 51.7 |
| 3 | ARX33P1.E5 | 117.0 | 57.4 |
| 4 | ARX33P1.E10 | 132.9 | 47.1 |
| 5 | ARX33P1.E11 | N.B. | N.B. |

N.B. = no significant binding observed

*All measurements were done in the presence of 0.1 mg/mL tRNA alongside the naïve pool ARC 212 (which showed no significant binding). When tRNA was not included in the reactions, measured $K_d$ values were approximately 2-3-fold lower (i.e. higher affinity).

PDGF-AA Aptamers

The sequences for PDGF-AA short form aptamers of the invention are presented in Table 11.

TABLE 11

Sequence Information for PDGF-AA (short form) aptamers

ARX33P1.D1 (SEQ ID NO: 94)
GGGAAAAGCGAATCATACACAAGATCGCCAGGAGCAAAGTCACGGAGGAGTGGGG

GTACGAATGCTCCGCCAGAGACCAACCGAGAA

ARX33P1.D2 (SEQ ID NO: 95)
GGGAAAAGCGAATCATACACAAGACCGGGAACTCGGATTCTTCGCATGTGGATGCG

ATCAGTATGCTCCGCCAGAGACCAACCGAGAA

ARX33P1.E5 (SEQ ID NO: 96)
GGGAAAAGCGAATCATACACAAGACCGGGAACTCGGATTCTTCACATGTGGATGTG

ATCAGTATGCTCCGCCAGAGACCAACCGAGAA

ARX33P1.E10 (SEQ ID NO: 97)
GGGAAAAGCGAATCATACACAAGACCGGGAAACTCGGATTCTTCGCATGTGGATGCG

ATCAGTATGCTCCGCCAGAGACCAACCGAGAA

ARX33P1.E11 (SEQ ID NO: 98)
GGGAAAAGCGAATCATACACAAGAGAGTGGAGGAGGTATGTATGGTTTGTGCGTCT

GGTGCGGTGCTCCGCCAGAGACCAACCGAGAA

Cell Based Assays with PDGF-AA Aptamers

The PDGF-AA aptamers that showed in vitro binding were tested in the 3T3 proliferation assay for their ability to inhibit PDGF-AA induced 3T3 cell proliferation. The assay was set up as previously described, using a titration of PDGF-AA aptamer (0-1 uM) against a constant concentration (50 ng/ml) of PDGF-AA protein (R&D Systems). The results in FIG. 24 show that the PDGF-AA aptamers ARX33P1.D2, ARX33P1.E5, and ARX33P1.E10 do inhibit PDGF-AA induced 3T3 cell proliferation, but are not very potent. FIG. 25 shows that PDGF-AA aptamers have no effect on PDGF-BB induced 3T3 cell proliferation, indicating that the PDGF-AA aptamers are highly specific for the PDGF-AA isoform.

The invention having now been described by way of written description and example, those of skill in the art will recognize that the invention can be practiced in a variety of embodiments and that the description and examples above are for purposes of illustration and not limitation of the following claims.

What is claimed is:

1. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is Tumor Necrosis Factor (TNF-α, and wherein the aptamer comprises the structural arrangement in a 5' to 3' direction: second nucleic acid sequence-first nucleic acid sequence-3'InvdT, where 3'InvdT represents a 3' inverted deoxythymidine.

2. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is selected from the group consisting of IgE and IgE Fcε R1, and wherein the aptamer comprises the structural arrangement in a 5' to 3' direction: second nucleic acid sequence-first nucleic acid sequence-3'InvdT, where 3'InvdT represents a 3' inverted deoxythymidine.

3. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is CD22, and wherein the aptamer comprises the structural arrangement in a 5' to 3' direction: second nucleic acid sequence-first nucleic acid sequence-3'InvdT, where 3'InvdT represents a 3' inverted deoxythymidine.

4. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is CTLA4, and wherein the aptamer comprises the structural arrangement in a 5' to 3' direction: second nucleic acid sequence-first nucleic acid sequence-3'InvdT, where 3'InvdT represents a 3' inverted deoxythymidine.

5. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is selected from the group consisting of PD-1, PD-L1, and PD-L2, and wherein the aptamer comprises the structural arrangement in a 5' to 3' direction: second nucleic acid sequence-first nucleic acid sequence-3'InvdT, where 3'InvdT represents a 3' inverted deoxythymidine.

6. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is FcRIIB, and wherein the aptamer comprises the structural arrangement in a 5' to 3' direction: second nucleic acid sequence-first nucleic acid sequence-3'InvdT, where 3'InvdT represents a 3' inverted deoxythymidine.

7. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is BTLA, and wherein the aptamer comprises the structural arrangement in a 5' to 3' direction: second nucleic acid sequence-first nucleic acid sequence-3'InvdT, where 3'InvdT represents a 3' inverted deoxythymidine.

8. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is transmembrane protein containing immunoglobulin and mucin-like domains (TIM-3), and wherein the aptamer comprises the structural arrangement in a 5' to 3' direction: second nucleic acid sequence-first nucleic acid sequence-3'InvdT, where 3'InvdT represents a 3' inverted deoxythymidine.

9. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is B lymphocyte activating factor (BAFF), and wherein the aptamer comprises the structural arrangement in a 5' to 3' direction: second nucleic acid sequence-first nucleic acid sequence-3'InvdT, where 3'InvdT represents a 3' inverted deoxythymidine.

10. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is B7-X, and wherein the aptamer comprises the structural arrangement in a 5' to 3' direction: second nucleic acid sequence-first nucleic acid sequence-3'InvdT, where 3'InvdT represents a 3' inverted deoxythymidine.

11. An aptamer comprising a first nucleic acid sequence that binds to a first target and a second nucleic acid sequence that binds to a second target, wherein the first sequence does not stimulate an immune response upon binding to the first target; and the second sequence is an immunostimulatory CpG motif that stimulates an immune response, wherein the CpG motif consists of an oligonucleotide sequence selected from the group consisting of (T/U)GAACG(T/U)(T/U)CGAGA(T/U) (SEQ ID NO: 13), AACG(T/U)(T/U)CGAGA(T/U) (SEQ ID NO: 14), AACG(T/U)(T/U)CGAG (SEQ ID NO: 15) and G(T/U)GAACG(T/U)(T/U)CGAG (SEQ ID NO: 16), wherein the first sequence binds to a first target, wherein the first target is CD25, and wherein the aptamer comprises the structural arrangement in a 5' to 3' direction: second nucleic acid sequence-first nucleic acid sequence-3'InvdT, where 3'InvdT represents a 3' inverted deoxythymidine.

12. A pharmaceutical composition comprising the aptamer of any one of claim 1 or 2-11, a cytotoxic agent and a pharmaceutically acceptable carrier.

13. The composition of claim 12, wherein the cytotoxic agent belongs to a class of cytotoxic agents selected from the group consisting of tubulin stabilizers, tubulin destabilizers, anti-metabolites, purine synthesis inhibitors, nucleoside analogs, DNA alkylating agents, DNA modifying agents and vascular disrupting agents.

14. The composition of claim 12, wherein the cytotoxic agent is selected from the group consisting of calicheamycin, doxorubicin, taxol, methotrexate, gemcitabine, cytarabine, vinblastin, daunorubicin, docetaxel, irinotecan, epothilone B, epothilone D, cisplatin, carboplatin and 5-fluoro-U.

* * * * *